US005830860A

United States Patent [19]

Gray et al.

[11] Patent Number: 5,830,860

[45] Date of Patent: *Nov. 3, 1998

[54] PEPTIDES WITH BACTERICIDAL ACTIVITY AND ENDOTOXIN NEUTRALIZING ACTIVITY FOR GRAM NEGATIVE BACTERIA AND METHODS FOR THEIR USE

[75] Inventors: Beulah H. Gray, St. Paul; Judith R. Haseman, Eagan; Kevin H. Mayo, Minnetonka, all of Minn.

[73] Assignee: Regents of the University of Minnesota, Minneapolis, Minn.

[ * ] Notice: The term of this patent shall not extend beyond the expiration date of Pat. No. 5,786,324.

[21] Appl. No.: 653,632

[22] Filed: May 24, 1996

Related U.S. Application Data

[63] Continuation-in-part of Ser. No. 218,026, Mar. 24, 1994.

[51] Int. Cl.[6] .......................... A61K 38/08; A61K 38/10; A61K 38/17

[52] U.S. Cl. ................................ 514/12; 514/13; 514/14; 514/15; 514/21; 435/69.7

[58] Field of Search ................................ 514/12, 13, 14, 514/15, 21; 435/69.7

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott | 514/12 |
| 5,198,541 | 3/1993 | Elsbach et al. | 435/69.1 |
| 5,334,584 | 8/1994 | Scott et al. | 514/12 |
| 5,348,942 | 9/1994 | Little et al. | 514/12 |

FOREIGN PATENT DOCUMENTS

| | | |
|---|---|---|
| WO 89/01486 | 2/1989 | WIPO . |
| WO 90/09183 | 8/1990 | WIPO . |
| WO 92/09621 | 6/1992 | WIPO . |
| WO 93/05797 | 4/1993 | WIPO . |
| WO 93/23434 | 11/1993 | WIPO . |
| WO 94/17819 | 8/1994 | WIPO . |
| WO 94/18323 | 8/1994 | WIPO . |
| WO 94/20532 | 9/1994 | WIPO . |
| WO 94/25476 | 11/1994 | WIPO . |
| WO 95/00641 | 1/1995 | WIPO . |
| WO 95/01428 | 1/1995 | WIPO . |
| WO 95/02414 | 1/1995 | WIPO . |

OTHER PUBLICATIONS

Bangalore, et al., "Identification of the Primary Antimicrobial Domains in Human Neutrophil Cathepsin G", *J. Biol. Chem.,* 265:13584–13588 (1990).

Bottone, et al., "Association of *Pseudomonas cepacia* with Chronic Granulomatous Disease", *J. Clin. Micro.,* 1:425–428 (1975).

Brown, et al., "Chemical Synthesis and Cloning of a Tyrosine tRNA Gene", *Methods in Enzymology,* 68:109–151 (1979).

Campanelli, et al., "Azurocidin and a Homologous Serine Protease from Neutrophils", *J. Clin. Invest.,* 85:904–915 (1990).

Capone, "Screening Recombinant Baculovirus Plaques In Situ with Antibody Probes", *Gene Anal. Techn.,* 6:62–66 (1989).

Casey, et al., "*Neisseria gonorrhoeae* Survive Intraleukocytic Oxygen–Independent Antimicrobial Capacities of Anaerobic and Aerobic Granulocytes in the Presence of Pyocin Lethal for Extracellular Gonococci", *Infect. Immun.,* 52:384–389 (1986).

Cody, et al., "Protective Anti–Lipopolysaccharide Monoclonal Antibodies Inhibit Tumor Necrosis Factor Production", *J. Surg. Res.,* 52:315–319 (1992).

Dintzis, et al., *Proteins* 16:306–308 (1993).

Dugas, et al., "Chemical Synthesis of Proteins", *Bioorganic Chemistry, Springer–Verlag,* NY at pp. 54–94 (1981).

Dunn, et al., "Efficacy of Type–Specific and Cross–Reactive Murine Monoclonal Antibodies Directed Against Endotoxin During Experimental Sepsis", *Surgery,* 98:283–290 (1985).

Elsbach, et al., "Bactericidal/permeability Increasing Protein and Host Defense Against Gram–negative Bacteria and Endotoxin", *Current Opinion in Immunology,* 5:103–107 (1993).

Farley, et al., "Lipopolysaccharide Structure Determines Tonic and Hydrophobic Binding of a Cationic Antimicrobial Neutrophil Granule Protein", *Infect. Immun.,* 56:1589–1592 (1988).

Gabay, et al., "Antibiotic Proteins of Human Polymorphonuclear Leukocytes", *Proc. Nat'l. Acad. Sci.,* 86:5610–5614 (1989).

Gallin, "Recent Advances in Chronic Granulomatous Disease", *Ann. Int. Med.,* 99:657–674 (1983).

Gazzano–Santoro, et al., "High–Affinity Binding of the Bactericidal/Permeability–Increasing Protein and a Recombinant Amino–Terminal Fragment to the Lipid A Region of Lipopolysaccharide", *Infect. Immun.,* 60:4754–4761 (1992).

Gray, et al., "Cloning of the cDNA of a Human Neutrophil Bactericidal Protein", *J. Biol. Chem.,* 264:9505–9509 (1989).

Hancock, "Alterations in Outer Membrane Permeability", *Ann. Rev. Microbiol.,* 38:237–264 (1984).

Hartree, "Determination of Protein: A Modification of the Lowry Method that Gives a Linear Photometric Response", *Anal. Biochem.,* 48:422–427 (1972).

(List continued on next page.)

*Primary Examiner*—Charles L. Patterson, Jr.

*Attorney, Agent, or Firm*—Merchant, Gould, Smith, Edell & Welter

[57] ABSTRACT

The invention provides biologically active peptides derived from or corresponding to regions of a bactericidal permeability increasing factor (B/PI). The peptides are preferably about 10 to 100 amino acids long and have bactericidal and/or endotoxin neutralizing activity. The peptides can be prepared by automated protein synthesis or by recombinant DNA methods. The peptides are useful in methods to treat and prevent bacterial infection in the body and on surfaces. The peptides are also useful to treat endotoxin shock and have endotoxin neutralizing activity.

17 Claims, 7 Drawing Sheets

OTHER PUBLICATIONS

Heumann, et al., "Competition between Bactericidal/Permeability–Increasing Protein and Lipopolysaccharide–Binding Protein for Lipopolysaccharide Binding to Monocytes", *J. Infect. Dis.,* 167:1351–1357 (1993).

Hoess, et al., "Crystal Structure of an Endotoxin–Neutralizing Protein from the Horseshoe Crab, Limulus Anti–LPS Factor, at 1.5 A Resolution", *EMBO Journal,* 12:3351–3356 (1993).

Holmes, et al., "Fatal Granulomatous Disease of Childhood", *Lancet,* 1:1225–1228 (1966).

Holmes, et al., "Studies of the Metabolic Activity of Leukocytes from Patients with a Genetic Abnormality of Phagocytic Function", *J. Clin. Invest.,* 46:1422–1432 (1967).

Holmes, "Metabolic Stimulation and Bactericidal Function to Polymorphonuclear Leukocytes", *Reticulo,. Soc.,* 22:87–88 (1978).

Homma, "A New Antigenic Schema and Live–cell Slide–agglutination Procedure for the Infrasubspecific, Serologic Classification of *Pseudomonas aeruginosa", Jpn. J. Exp. Med.,* 46:329–336 (1976).

Hovde, et al., "Physiological Effects of a Bactericidal Protein from Human Polymorphonuclear Leukocytes on *Pseudomonas aeruginosa", Infect. Immun.,* 52:90–95 (1986).

Hovde, et al., "Characterization of a Protein from Normal Human Polymorphonuclear Leukocytes with Bactericidal Activity Against *Pseudomonas aeruginosa", Infect. Immun.,* 54:142–148 (1986).

Jameson, et al., *Nature* 368:744–746 (1994).

Johnston, et al., "Chronic Granulomatous Disease", *Ped. Clin. of N. Amer.,* 24:3650376 (1977).

Johnston, "Molecular Science Sets Its Sights on Septic Shock", *J. NIH Res.,* 3:61–65 (1991).

Kambic, et al., "Biomaterials in Artificial Organs", *Chem & Eng. News* at pp. 31–48 (Apr. 14, 1986).

Kelly, et al., "Role of Bactericidal Permeability–Increasing Protein in the Treatment of Gram–Negative Pneumonia", *Surgery,* 114:140–146 (1993).

Kyte, et al., "A Simple Method for Displaying the Hydropathic Character of a Protein", *J. Mol. Biol.,* 157:105–132 (1982).

Larrick, et al., "Polymerase Chain Reaction Using Mixed Primers: Cloning of Human Monoclonal Antibody Variable Region Genes from Single Hybridoma Cells", *Bio/Tech,* 7:934–938 (1989).

Lasdun, et al., "Inhibition of Endopeptidase 24.15 Slows the In Vivo Degradation of Luteinizing Hormone–Releasing Hormone", *J. Pharm. Exp. Therap.,* 251:439–447 (1989).

Lehrer, et al., "Defensins: Antimicrobial and Cytotoxic Peptides of Mammalian Cells", *Ann. Rev. of Immunol.,* 11:105–128 (1993).

Little, et al., "Functional Domains of Recombinant Bactericidal/Permeability Increasing Protein ($rBPI_{23}$)", *J. Biol. Chem.,* 269:1865–1872 (1994).

Luckow, et al., "Trends in the Development of Baculovirus Expression Vectors", *Biotech,* 6:47–55 (1988).

Mandell, "Bactericidal Activity of Aerobic and Anaerobic Polymorphonuclear Neutrophils", *Infect. Immun.,* 9:337–341 (1974).

Mannion, et al., "Separation of Sublethal and Lethal Effects of the Bactericidal/Permeability Increasing Protein on *Escherichia coli", J. Clin. Invest.,* 85:853–860 (1990).

Marra, et al., "Bactericidal/Permeability–Increasing Protein has Endotoxin–Neutralizing Activity", *J. Immunol.,* 144:662–666 (1990).

Marra, et al., "The Role of Bactericidal/Permeability–Increasing Protein as a Natural Inhibitor of Bacterial Endotoxin", *J. Immunol.,* 148:532–537 (1992).

Mossman, et al., "Rapid Colorimetric Assay for Cellular Growth and Survival: Application to Proliferation and Cytotoxicity Assays", *Immunological Methods,* 65:55–63 (1983).

Okamura, et al., "Outer Membrane Mutants of *Salmonella typhimurium* LT2 Have Lipopolysaccharide–Dependent Resistance to the Bactericidal Activity of Anaerobic Human Neutrophils", *Infect. Immun.,* 36:1086–1095 (1982).

Ooi, et al., "A 25–kDa $NH_2$–terminal Fragment Carries all the Antibacterial Activities of the Human Neutrophil 60–kDa Bactericidal/Permeability–Increasing Protein", *J. Biol. Chem.,* 262:14891–14894 (1987).

Ooi, et al., "Endotoxin–neutralizing Properties of the 25 kD N–Terminal Fragment of the 55–60 kD Bacteridical/Permeability–Increasing Protein of Human Neutrophils", *J. Exp. Med.,,* 174:649–654 (1991).

Pereira, et al., "Synthetic Bactericidal Peptide Based on CAP37: A 37–kDa Human Neutrophil Granule–associated Cationic Antimicrobial Protein Chemotactic for Monocytes", *Proc. Nat'l. Acad. Sci. USA,* 90:4733–4737 (1993).

Quie, et al., "In vitro Bactericidal Capacity of Human Polymorphonuclear Leukocytes: Diminished Activity in Chronic Granulomatous Disease of Childhood", *J. Clin. Invest.,* 46:668–679 (1967).

Rest, "Killing of *Neisseria gonorrhoeae* by Human Polymorphonuclear Neutrophil Granule Extracts", *Infect. Immun.,* 25:574–579 (1979).

Rest, et al., "Interactions of *Neisseria gonorrhoeae* with Human Neutrophils: Effects of Serum and Gonococcal Opacity on Phagocyte Killing and Chemiluminescence", *Infect. Immun.,* 36:737–744 (1982).

Rustici, et al., "Molecular Mapping and Detoxification of the Lipid A Binding Site by Synthetic Peptides", *Science,* 259:361–365 (1993).

Shafer, et al., "Lipid A and Resistance of *Salmonella typhimurium* to Antimicrobial Granule Proteins of Human Neutrophil Granulocytes", *Infect. Immun.,* 43:834–838 (1984).

Shafer, et al., "Cationic Antimicrobial Proteins Isolated from Human Neutrophil Granulocytes in the Presence of Diisopropyl Fluorophosphate", *Infect. Immun.,* 45:29–35 (1984).

Shafer, et al., "Synthetic Peptides of Human Lysosomal Cathepsin G with Potent Antipseudomonal Activity", *Infection and Immunity,* 61:1900–1908 (1993).

Shinefield, et al., "Preliminary Observations on Artificial Colonization of Newborns", *Amer. J. Dis. Chil.,* 105:146–154 (1963).

Siefferman, et al., "*Pseudomonas aeruginosa* Variants Isolated from Patients with Cystic Fibrosis are Killed by a Bactericidal Protein from Human Polymorphonuclear Leukocytes", *Infect. Immun.,* 59:2152–2157 (1991).

Spitznagel, "Antibiotic Proteins of Human Neutrophils", *J. Clin. Invest.,* 86:1381–1386 (1990).

Su, et al., *Horm. Metab. Res.,* 22:15–21 (1991).

Wang, et al., "Direct Double–Stranded DNA Sequencing with Baculovirus Genomes", *J. Virol. Meth.,* 31:113–118 (1991).

Wasiluk, et al., "Comparison of Granule Proteins from Human Polymorphonuclear Leukocytes Which are Bactericidal Toward *Pseudomonas aeruginosa*", *Infect. Immun.,* 59:4193–4200 (1991).
Weiss, et al., "Purification and Characterization of a Potent Bactericidal and Membrane Active Protein from the Granules of Human Polymorphonuclear Leukocytes", *J. Biol. Chem.,* 253:2664–2672 (1978).
Weiss, et al., "Killing of Gram–Negative Bacteria by Polymorphonuclear Leukocytes", *J. Clin. Invest.,* 69:959–970 (1982).
Weiss, et al., "Environmental Modulation of Lipopolysaccharide Chain Length Alters the Sensitivity of *Escherichia coli* to the Neutrophil Bactericidal/Permeability–Increasing Protein", *Infect. Immun.,* 51:594–599 (1986).
Weiss, et al., "Human Bactericidal/Permeability–Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.,* 90:1122–1130 (1992).

1 21 41
ATG AGA GAG AAC ATG GCC AGG GGC CCT TGC AAC GCG CCG AGA TGG GTG TCC CTG ATG GTG
1: m r e n m a r g p c n a p r w v s l m v

GI
61 81 101
CTC GTC GCC ATA GGC ACC GCC GTG ACA GCG GCC GTC AAC CCT GGC GTC GTG GTC AGG ATC
1: l v a i g t a v t a a v n p g v v v r i 121 141 161
TCC CAG AAG GGC CTG GAC TAC GCC AGC CAG CAG GGG ACG GCC GCT CTG CAG AAG GAG CTG
1: s q k g l d y a s q q g t a a l q k e l 181 201 221
AAG AGG ATC AAG ATT CCT GAC TAC TCA GAC AGC TTT AAG ATC AAG CAT CTT GGG AAG GGG
1: k r i k i p d y s d s f k i k h l g k g

H A
241 261 281
CAT TAT AGC TTC TAC AGC ATG GAC ATC CGT GAA TTC CAG CTT CCC AGT TCC CAG ATA AGC
1: h y s f y s m d i r e f q l p s s q i s 301 321 341
ATG GTG CCC AAT GTG GGC CTT AAG TTC TCC ATC AGC AAC GCC AAT ATC AAG ATC AGC GGG
1: m v p n v g l k f s i s n a n i k i s g

B C
361 381 401
AAA TGG AAG GCA CAA AAG AGA TTC TTA AAA ATG AGC GGC AAT TTT GAC CTG AGC ATA GAA
1: k w k a q k r f l k m s g n f d l s i e 421 441 461
GGC ATG TCC ATT TCG GCT GAT CTG AAG CTG GGC AGT AAC CCC ACG TCA GGC AAG CCC ACC
1: g m s i s a d l k l g s n p t s g k p t

D E
481 501 521
ATC ACC TGC TCC AGC TGC AGC AGC CAC ATC AAC AGT GTC CAC GTG CAC ATC TCA AAG AGC
i t c s s c s s h i n s v h v h i s k s 541 561 581
AAA GTC GGG TGG CTG ATC CAA CTC TTC CAC AAA AAA ATT GAG TCT GCG CTT CGA AAC AAG
1: k v g w l i q l f h k k i e s a l r n k 601 621 641
ATG AAC AGC CAG GTC TGC GAG AAA GTG ACC AAT TCT GTA TCC TCC AAG CTG CAA CCT TAT
1: m n s q v c e k v t n s v s s k l q p y

F
661 681 701
TTC CAG ACT CTG CCA GTA ATG ACC AAA ATA GAT TCT GTG GCT GGA ATC AAC TAT GGT CTG
1: f q t l p v m t k i d s v a g i n y g l 721 741 761
GTG GCA CCT CCA GCA ACC ACG GCT GAG ACC CTG GAT GTA CAG ATG AAG GGG GAG TTT TAC
1: v a p p a t t a e t l d v q m k g e f y 781 801 821
AGT GAG AAC CAC CAC AAT CCA CCT CCC TTT GCT CCA CCA GTG ATG GAG TTT CCC GCT GCC
1: s e n h h n p p p f a p p v m e f p a a 841 861 881
CAT GAC CGC ATG GTA TAC CTG GGC CTC TCA GAC TAC TTC TTC AAC ACA GCC GGG CTT GTA
1: h d r m v y l g l s d y f f n t a g l v

FIG. 4

PEPTIDES WITH BACTERICIDAL ACTIVITY AND ENDOTOXIN NEUTRALIZING ACTIVITY FOR GRAM NEGATIVE BACTERIA AND METHODS FOR THEIR USE

This application is a continuation-in-part of U.S. patent application Ser. No. 08/218,026 filed Mar. 24, 1994.

This invention was made with support from The Cystic Fibrosis Foundation and with government support under 2R01-A1-26159 awarded by the National Institute of Health. The Government has certain rights in the invention.

BACKGROUND OF THE INVENTION

The microbicidal mechanisms of polymorphonuclear leukocytes (PMNL) depend on the products of phagocytosis-stimulated oxidative metabolism for killing of many bacteria. Oxygen-dependent intracellular killing of *Staphylococcus aureus, Serratia marcescens, Proteus mirabilis, Escherichia coli*, and *Pseudomonas cepacia* is indicated because these bacteria are not killed by PMNL in which the oxidative burst is rendered nonfunctional. PMNL from patients with Chronic Granulomatous Disease (CGD), an inherited deficiency of the oxidative response, are unable to kill the above bacteria and CGD patients have a corresponding susceptibility to infection by these same bacteria. Gallin, *Ann. Int. Med*., 99:657 (1983); Johnston et al., *Ped. Clin. of N. Amer*., 24:365 (1977); Holmes et al., *Lancet*, 1:1225 (1966); Quie et al., *J. Clin. Invest*., 46:668 (1967); Bottone et al., *J. Clin. Med*., 1:425 (1975); and Holmes et al., *J. Clin. Invest*., 46:1422 (1967). The bacteria listed above are also not killed by normal human PMNL incubated in an anaerobic environment. Mandell, *Infect. Immun*., 9:337 (1974).

Conversely, a significant contribution of oxygen-independent microbicidal mechanisms is invoked when the rate and extent of intracellular killing by anaerobic normal human PMNL, PMNL from CGD patients, or aerobically-incubated normal human PMNL are equal. *Salmonella typhimurium* are killed by CGD cells at a normal rate and at a near normal rate by control PMNL incubated anaerobically. Weiss et al., *J. Clin. Invest*., 69:959 (1982); Mandell, cited supra.; and Okamura et al., *Infect. Immun*., 36:1086 (1982). *Neisseria gonorrhoea* are killed by CGD cells as well as they are by normal PMNL and are killed at a normal rate by anaerobic normal PMNL. Rest et al., *Infect. Immun*., 36:737 (1982); and Casey et al., *Infect. Immun*., 52:384, (1986). It has been established that PMNL from patients with CGD retain a normal ability to kill *Pseudomonas aeruginosa* strains and, when incubated under anaerobic conditions, normal human PMNL kill *P. aeruginosa* as well as they do in an aerobic environment. Holmes, *Reticulo. Soc*., 22:87 (1978); and Mandell, cited supra. The evidence strongly suggests that intracellular killing of these bacteria by oxygen-independent mechanisms depends on the toxicity of the contents of cytoplasmic granules from PMNL. Weiss et al., *J. Clin. Invest*., 69:959 (1982); Holmes, *Reticulo. Soc*., 22:87 (1978); and Rest, *Infect. Immun*., 25:574 (1979). Bactericidal factors which are implicated in oxygen-independent mechanisms have been purified from the extracts of these cytoplasmic granules.

Weiss et al. have described a 58–60 kD bactericidal/permeability increasing protein (B/PI) active against *S. typhimurium* and *E. coli*. Weiss et al., *J. Biol. Chem*., 253:2664 (1978). Shafer et al. have described the purification of a 56 kD cationic antibacterial protein (CAP57) and a 37 kD protein (CAP37) with activity towards *S. typhimurium*. Shafer et al., *Infect. Immun*., 45:29 (1984). A 55 kD glycoprotein (BP55) having potent bactericidal activity towards *P. aeruginosa* has been purified. Hovde et al., *Infect. Immun*., 54:142 (1986). Intracellular killing of *N. gonorrhoea* has been traced to the nonenzymatic bactericidal activity of cathepsin G. Bangalore et al., *J. Biol. Chem*., 265:13584 (1990). The cationic peptide defensins are also strong candidates for the oxygen-independent microbicidal mechanisms of PMNL. Lehrer et al, *Ann. Rev. of Immunol*., 11:105 (1993). Two apparently novel microbicidal substances, azurocidin and p29b, have also been shown to have bactericidal activity. Gabay et al., *Proc. Natl. Acad. Sci*., 86:5610 (1989); and Campanelli et al., *J. Clin. Invest*., 85:904 (1990). Although azurocidin and cathepsin G kill *P. aeruginosa*, they are 80 to 140-fold less active than BP55. The evidence that azurocidin and CAP37 are the same protein has recently been reviewed. Wasiluk et al., *Infect. Immun*., 59:3193 (1991).

It is likely that BP55, B/PI and CAP57 are the same molecule based on comparison of N-terminal amino acid sequences. The identical amino-terminal amino acid sequences of BP55, B/PI and CAP57 correspond to the amino acid sequence deduced from the nucleotide sequence of a full length cDNA clone for B/PI. In addition, a monoclonal antibody to CAP57 was shown to cross react with B/PI. Spitznagel, *J. Clin, Invest*., 86:1381 (1990). B/PI are primarily bactericidal toward gram-negative bacteria. Studies of CAP57 and B/PI have concentrated on studies of *E. coli* and *S. typhimurium*. The studies of BP55 evolved from the demonstration that *P. aeruginosa* was killed by an oxygen-independent mechanism. Although there was no evidence of permeability increase in *P. aeruginosa*, the inner membrane functions of *P. aeruginosa*, such as amino acid transport, ceased immediately upon exposure to BP55. Hovde et al., *Infect. Immun*., 52:90 (1986). Studies of *E. coli* have recently confirmed the loss of amino acid transport function in the lethal effects of B/PI at pH 6.0. Mannion et al., *J. Clin. Invest*., 85:853 (1990). A reference to B/PI will be understood to also refer to BP55.

An important persistent difference of the studies f *P. aeruginosa* with BP55 is that, whether smooth or rough, serum-resistant or serum-sensitive, all strains of Pseudomonas thus far studied are equally sensitive to killing by BP55. Siefferman et al., *Infect. and Immun*., 59:2152 (1991). By contrast, studies of *S. typhimurium* and *E. coli* have consistently shown that resistance to CAP57 and B/PI increases dramatically with the length of the O polysaccharide chains on the LPS of the respective bacterial outer membranes. Gabay et al., cited supra.; Campanelli et al., cited supra; Wasiluk et al., cited supra.; Spitznagel, cited supra.; Elsbach et al., *Curr. Opinion in Imm*., 5:103 (1993); Ooi et al., *J. Biol. Chem*., 262:14891 (1987); Gray et al., *J. Biol. Chem*., 264:9505 (1989); Hovde et al., *Infect. Immun*., 52:90 (1986); Mannion et al., cited supra.; Siefferman et al., cited supra.; Farley et al., *Infect. Immun*., 56:1589 (1988); and Weiss et al., *Infect. Immun*., 51:594 (1986).

Recent studies of B/PI (BP55) have adjusted its molecular mass to 55 kD and turned to its ability to neutralize the endotoxin effects of *E. coli* LPS. The ability to neutralize endotoxin, as well as the bactericidal function, has been localized to the amino-terminal half of the B/PI molecule of 199 amino acids. The native B/PI molecule ($nBPI_{55}$) has been shown to neutralize the pyrogenicity of LPS for rabbits, the ability of LPS to initiate the coagulation pathway of the Limulus amoebocyte lysate, and the ability of LPS to cause tumor necrosis factor (TNF) release from human monocytes.

Marra et al., *J. Immunol.*, 148:532 (1992); and Marra et al., *J. Immunol.*, 144:662 (1990). The carboxyl-terminal half of $nBPI_{55}$ inhibits the ability of LPS to cause TNF release from whole blood and is active in the inhibition of effects of LPS on the Limulus amoebocyte lysate. Ooi et al., *J. Exp. Med.*, 174:649 (1991).

Neutralization of the ability of LPS to activate in the Limulus assay has also been demonstrated for a 25 kD amino-terminal proteolytic fragment of native B/PI ($nBPI_{25}$) and for a 23 kD recombinant form ($rBPI_{23}$) of the same region of B/PI. Ooi et al., *J. Exp. Med.*, 174:649 (1991); and Weiss et al., *J. Clin. Invest.*, 90:1122 (1992). The $nBPI_{25}$ fragment and the $rBPI_{23}$ product consist of the first 199 amino acids of the amino terminus of B/PI. Both are capable of killing *E. coli* and of binding to LPS or lipid A while neutralizing the ability of endotoxin to up regulate the expression of complement receptors on neutrophils and to cause TNF release from whole blood. Elsbach et al., cited supra.; and Weiss et al., *J. Clin. Invest.*, 90:1122 (1992). High affinity binding of LPS by $rBPI_{23}$ has been demonstrated. Gazzano-Santoro et al., *Infect. Immun.*, 60:4754 (1992); and Heumann et al., *J. Infect. Dis.*, 167:1351 (1993).

The accumulated evidence suggests that the binding site for BP55, CAP57, and B/PI is the lipid A moiety of the outer membrane lipopolysaccharide (LPS) of gram-negative bacteria. LPS is anchored in the outer membrane by noncovalent cross-bridging of adjacent LPS molecules with divalent cations ($MG^{++}$and $Ca^{++}$) which are tightly bound to anionic phosphate groups clustered at the base of the polysaccharide chain near the hydrophobic lipid A moiety. Hancock, *Ann. Rev. Microbiol.*, 38:237 (1984). B/PI and CAP57 appear to compete with $Mg^{++}$and $Ca^{++}$for these surface sites and binding is largely determined by the accessibility of these anionic groups. Binding of B/PI can be inhibited by the presence of 2.5 mM $Mg^{++}$and bound B/PI can be removed by the addition of 80 mM $Mg^{++}$. Weiss et al., *J. Biol. Chem.*, 253:2664 (1978); and Weiss et al., *J. Clin. Invest.*, 71:540 (1983). The presence of free LPS will inhibit binding of BP55, B/PI and CAP57. Wasiluk et al., cited supra.; Weiss et al., *J. Biol. Chem.*, 253:2664 (1978); and Shafer et al., *Infect. Immun.*, 43:834 (1984).

Studies of two strains of *S. typhimurium* which differed only in the degree of substitution of the 4'-phosphate of lipid A with 4-amino-L-arabinose provide the only direct evidence of the interaction of antibacterial protein with ionic groups of the lipid A and inner core region of LPS. A strain with 70% substitution of the 4' phosphate was significantly more resistant to killing by CAP57 than was the isogeneic strain. Shafer et al., *Infect. Immun.*, 43:834 (1984). Others have shown that the terminal phosphate group of lipid A is important for binding of $nBPI_{55}$. In vivo studies in mice of $nBPI_{55}$ and $rBPI_{23}$ have shown that both are effective in the treatment of gram-negative pneumonia. Kelly et al., *Surgery*, 114:140 (1993).

Thus, there is a need for compositions effective to treat and prevent gram-negative infections and endotoxin shock associated with gram-negative infection. There is a need to develop large amounts of therapeutically active peptides that can be used to treat gram-negative infections and endotoxin shock.

SUMMARY OF THE INVENTION

The invention provides biologically active peptides having an amino acid sequence derived from or corresponding to regions of B/PI. The biologically active peptides are preferably 10 to 100 amino acids long and have bactericidal activity and/or endotoxin neutralizing activity. The bactericidal peptides preferably kill strains of Pseudomonas but can also kill *S. aureus*. The peptides can be modified by the addition of cysteine residues and form dimers or cyclic peptides. Peptides can also be attached to carrier molecules such as serum albumin to form peptide conjugates useful to generate monoclonal antibodies and in pharmaceutical compositions.

The peptides are useful in methods of treating bacterial infection and endotoxin shock. The peptides demonstrate endotoxin neutralizing activity. The methods of the invention involve administering a pharmaceutical composition to an animal to inhibit the bacterial infection or decrease the symptoms of endotoxin shock. The pharmaceutical composition includes an amount of a bactericidal and/or endotoxin neutralizing peptide sufficient to inhibit infection or decrease the symptoms of endotoxin shock. The peptides are in admixture with a pharmaceutically acceptable carrier.

The peptides are also useful as a coating on a prosthetic or implantable device to inhibit bacterial infection associated with introduction of such devices into the body. The peptide is attached to the surface of the prosthetic device in an amount effective to inhibit growth of the bacteria, especially *Pseudomonas spp*. The peptide can optionally be coupled to a carrier molecule before attachment to the surface of the prosthetic device.

The biologically active peptides of the invention can be prepared by automated synthesis or recombinant DNA technology. Thus, the invention also provides for DNA sequences coding for the biologically active peptides of the invention.

Preferred peptides of this invention include peptides from amino acids 82–106 of B/PI. Internal cysteines incorporated into this region enhance activity of the peptide. Other modifications to peptides from this region include the use of reverse D-amino acids, reverse orientation peptides, hybrid peptides that include peptide sequence from amino acids 82–106 of B/PI and hybrid proteins with substitutions in the portion of the hybrid peptide derived from B/PI.

In one embodiment, the invention includes a hybrid peptide having bactericidal and endotoxin neutralizing activity comprising exogenous amino acids flanking an amino acid sequence from B/PI, wherein the amino acid sequence comprises at least the amino acid region KWKAQKRFLK. The exogenous amino acids can be positioned along one or along both sides of the peptide. In one aspect of this embodiment, the amino acid sequence from B/PI is in the reverse orientation and the peptide can include at least one and not more than 5 amino acid substitutions. In another aspect of this embodiment, the hybrid peptide has a sequence selected from the group consisting of

HIKELQVKWKAQKRFLKMSIIVKLNDGRELSLD (SEQ ID NO:63),

ANIKLSVKWKAQKRFLKMSIIVKLNDGRELSLD (SEQ ID NO:64),

SIQDLNVSMKLFRKQAKWKIIVKLNDGRELSLD (SEQ ID NO:65), and

ANIKLSVEMKLFKRHLKWKIIVKLNDGRELSLD (SEQ ID NO:66).

In another embodiment of this invention a peptide is disclosed having bactericidal or endotoxin neutralizing activity, wherein the peptide comprises an amino acid sequence KWKAQKRFLK, and wherein the peptide has at least two cysteine residues positioned within the peptide so that the amino acid sequence KWKAQKRFLK is positioned between at least two of the cysteine residues. In one aspect of this invention the amino acid sequence comprises at least the amino acid region KWKAQKRFLK and no more than the amino acid sequence ISNANIKISGKWKAQKRFLK-MSGNFDLSI from B/PI and in another aspect of this embodiment, the peptide is selected from a group consisting of:

ISNANCKISGKWKAQKRFLKMSGNFDCSI (SEQ ID NO:61) and

NANCKISGKWKAQKRFLKMSGNFDCSI (SEQ ID NO:62).

In yet another aspect of this invention the peptides, including SEQ ID NO:61 and SEQ ID NO:62 are synthesized in the reverse orientation and in another they are synthesized in reverse orientation using D-amino acids.

In another aspect of this invention a peptide having bactericidal or endotoxin neutralizing activity is claimed comprising an amino acid sequence KWKAQKRFLKA from B/PI in reverse orientation. In a preferred aspect of this invention the peptide is synthesized from D-amino acids.

In another preferred embodiment, a method is disclosed for treating a bacterial infection or endotoxic shock comprising administering an amount of a pharmaceutical composition effect to inhibit the bacterial infection or neutralize endotoxin to an animal, wherein the pharmaceutical composition comprises: (a) a peptide demonstrating gram negative bactericidal activity or endotoxic neutralizing activity selected from the group consisting of: a hybrid peptide comprising exogenous amino acids flanking at least one side of an amino acid sequence from B/PI, wherein the amino acid sequence comprises at least the amino acid region KWKAQKRFLK; a hybrid peptide comprising exogenous amino acids flanking at least one side of an amino acid sequence from B/PI, wherein the amino acid sequence comprises at least the amino acid region KWKAQKRFLK; a peptide having bactericidal or endotoxin neutralizing activity, wherein said peptide comprises an amino acid sequence KWKAQKRFLK, wherein the peptide has at least two cysteine residues positioned within the peptide so that the amino acid sequence KWKAQKRFLK is positioned between at least two of the cysteine residues; and a peptide having bactericidal or endotoxin neutralizing activity, wherein said peptide comprises an amino acid sequence KWKAQKRFLK, wherein the peptide has at least two cysteine residues positioned within the peptide so that the amino acid sequence KWKAQKRFLK is positioned between at least two of the cysteine residues, wherein the peptide is synthesized in the reverse orientation; and(b) a pharmaceutically acceptable carrier.

In one aspect of this method, the peptide comprises at least KWKAQRFLK and no more than the amino acid sequence ISNANIKISGKWKAQKRFLKMSGNFDLSI and in another aspect of this method, the peptide of step (a) comprises at least one and not more than 5 amino acid substitutions in the amino acid sequence KWKAQRFLK.

BRIEF DESCRIPTION OF THE FIGURES

FIG. 4 represents a nucleotide sequence (SEQ ID NO:1) coding for B/PI and the predicted amino acid sequence (SEQ ID NO:2).

DETAILED DESCRIPTION OF THE INVENTION

The invention provides for peptides derived from a neutrophil bacterial permeability protein (B/PI). The peptides are those that are biologically active for bacterial killing or endotoxin neutralization or both. Preferably, the peptides are about 10 to about 100 amino acids long and contain hydrophilic regions based upon the hydropathy plot of B/PI of Table 1. The peptides can be modified in many ways including by addition of N- and/or C-terminal cysteine residues. The peptides are useful in pharmaceutical compositions to treat and prevent bacterial infections and endotoxin shock. The peptides may also be useful to prevent the growth of bacteria on surfaces. The invention, therefore, also provides for methods of using the peptides to treat and prevent bacterial infection and endotoxin shock.

Figure 8:
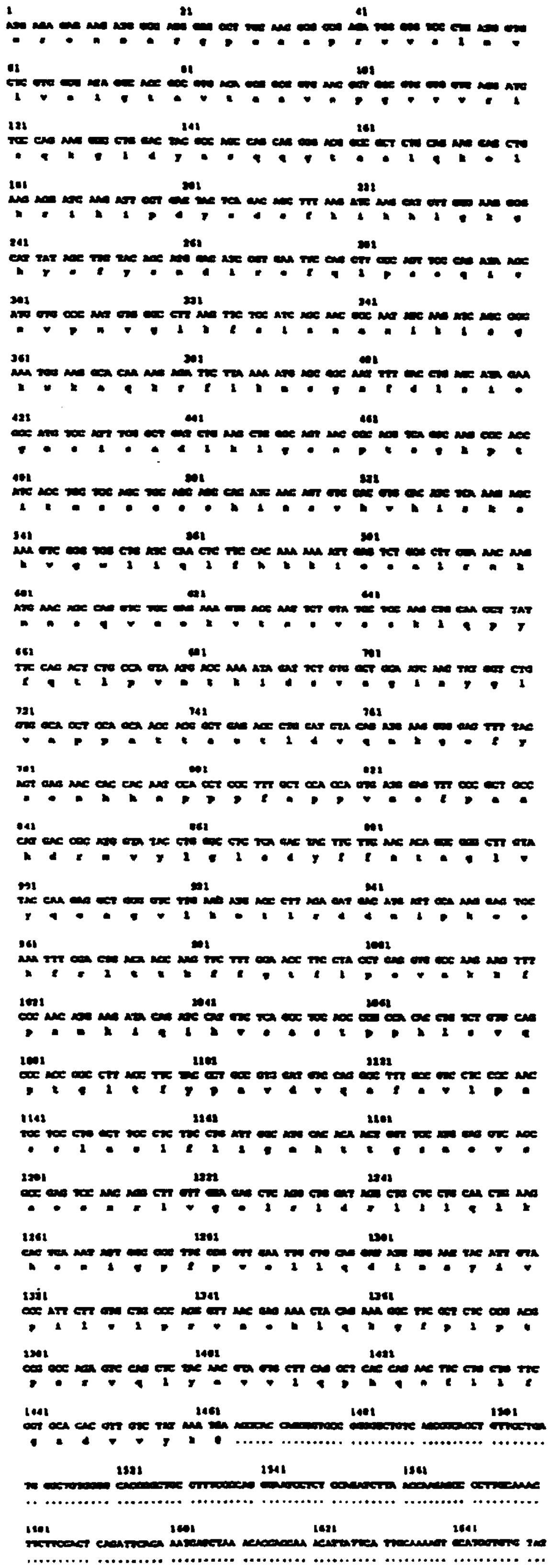
FIG. 8 is the entire sequence of a cDNA (SEQ ID NO:3) encoding a 55,000 dalton B/PI protein (SEQ ID NO:4).

A. Isolation of Bacteria Permeability Protein from Neutrophils and Selection of Biologically Active Peptides A bactericidal protein (B/PI) having a molecular weight of 55,000 daltons as determined by SDS-PAGE can be isolated from human neutrophils. Briefly, a granular extract from human neutrophils can be separated by Orange A (Amicon Corp., Beverly, Mass.) column chromatography. Fractions having bactericidal activity for *P. aeruginosa* can be pooled and separated by cation exchange chromatography. Fractions having bactericidal activity can be pooled and further separated by molecular-sieving chromatography. Fractions having bactericidal activity can be pooled and characterized by SDS-PAGE. The B/PI protein can be further characterized by its amino acid sequence. A cDNA sequence coding for B/PI generated by standard methods provides the predicted amino acid sequence for B/PI as shown in FIG. 4 and FIG. 8. Isolated native B/PI has the N-terminal amino acid sequence of:

VNPGVVVRISQKGLDYASQQG (SEQ ID NO:5)

which is in agreement with the predicted amino acid sequence for the N-terminal region of B/PI shown in FIG. 4 and FIG. 8.

Once the predicted amino acid sequence of B/PI is known, biologically active peptides having an amino acid sequence derived from or corresponding to that of B/PI can be selected and/or modified. A peptide sequence that is derived from or corresponding to a peptide from B/PI has about 90–100% sequence identity and has at least one functional activity in common with B/PI. The peptide sequence can be selected based on several criteria including the biological activity, hydrophilicity, and size. Biologically active peptides include those that are bactericidal, those that have endotoxin neutralizing activity, and those that have both activities.

Bactericidal activity can be evaluated against a variety of bacteria such as *Pseudomonas spp* including *aeruginosa* and *P. cepacia, E. coli B*, and *Staphylococcus aureus*. The preferred organism is *P. aeruginosa*. Bactericidal activity is determined by identifying the effective dose for killing as the molar concentration of the peptide which results in at least a 60% killing of the bacteria, as determined by standard methods. Preferably, the peptide has an effective dose at a concentration of about $1\times10^{-4}$M to about $1\times10^{-10}$M, and more preferably $1\times10^{-7}$M to $1\times10^{-9}$M. Peptides corresponding to and/or derived from B/PI that were considered not bactericidal did not kill *P. aeruginosa* at concentrations of $10^{-4}$M or less at a pH of 5.6. The effective dose for bactericidal activity of B/PI is seen at about $10^{-9}$ to $10^{-10}$M. Bactericidal activity can also be determined by calculating a lethal dose 50, ($LD_{50}$) using standard methods. The $LD_{50}$, is that amount of peptide or protein that kills 50% of the bacteria when measured using standard dose response methods. See FIG. 1. A bactericidal peptide preferably has an $LD_{50}$ of about $10^{-4}$M to about $10^{-9}$M, more preferably about $10^{-7}$ to $10^{-9}$M.

The peptide selected can also have endotoxin neutralizing activity. Endotoxin neutralizing activity can be measured by determining the molar concentration at which the peptide completely inhibits the action of lipopolysaccharide in an assay such as the Limulus amoebocyte lysate assay (LAL) (Sigma Chemicals, St. Louis, Mo.) or the chromogenic LAL 1000 test (Biowhittacker, Walkersville, Md.). Endotoxin neutralizing activity can also be measured by calculating an inhibitory does 50 ($LD_{50}$) using standard does response methods. An inhibitory dose 50 is that amount of peptide that can inhibit 50% of the activity of endotoxin. Endotoxin activity can also be measured by determining the amount of release of tumor necrosis factor alpha (TNFA) from a macrophage cell line or by evaluating the symptoms of shock in animals. Peptides preferably neutralized endotoxin at a molar concentration of about $1\times10^{-4}$M to about $10^{-8}$M, more preferably about $10^{-5}$M to about $10^{-6}$M. The native B/PI molecule has endotoxin neutralizing activity at about $10^{-8}$M. Peptides derived and/or modified from B/PI that were considered to not have endotoxin neutralizing activity did not neutralize endotoxin at a molar concentration of $10^{-4}$ or less.

Figure 6:
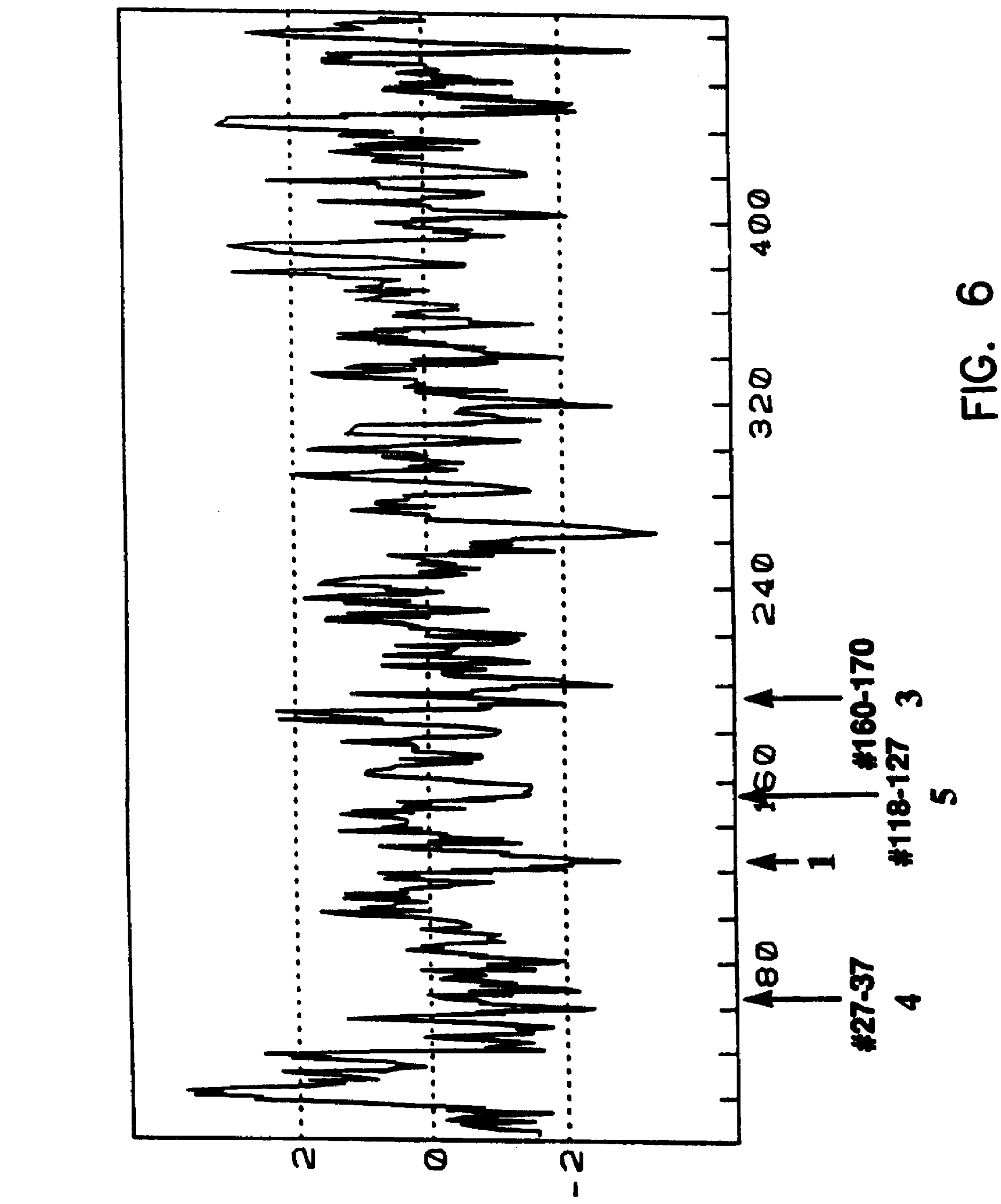
FIG. 6 is a hydropathy plot of B/PI based upon the average of 5 amino acid stretches.

Peptides selected can also have a hydrophilic character as determined by a hydropathy plot, according to the method of Kyte and Doolittle, *J. Mol. Biol.*, 157:105 (1982) see FIG. 6. Hydropathy plots can be used to calculate a hydropathy index for peptides and identify regions of polypeptides that are hydrophilic in character. Hydrophilic peptides of B/PI and the hydropathy index for those peptides are shown in Table 1.

TABLE I

HYDROPATHY INDICES OF PEPTIDES DERIVED FROM OR CORRESPONDING TO B/PI

| | Derived from B/PI | Net Hydropathy Index$_b$ |
|---|---|---|
| #90-99 | kwkaqkrflk (SEQ ID NO: 6) | −16.1 |
| C#90-99 | ckwkaqkrflk (SEQ ID NO: 7) | −13.6 |

TABLE I-continued

HYDROPATHY INDICES OF PEPTIDES DERIVED FROM OR CORRESPONDING TO B/PI

| | Derived from B/PI | Net Hydropathy Index$_b$ |
|---|---|---|
| #90-102 | kwkaqkrflkmsg (SEQ ID NO: 8) | −15.4 |
| #86-99 | kisgkwkaqkrflk (SEQ ID NO: 9) | −16.7 |
| C86-99 | ckisgkwkaqkrflk (SEQ ID NO: 10) | −14.2 |
| Hybrid | efysenhhnpkwkaqkrflk (SEQ ID NO: 11) | −31.7 |
| CHybrid | cefysenhhnpkwkaqkrflk (SEQ ID NO: 12) | −34.2 |
| Signal | mrenmargpc (SEQ ID NO: 13) | −9.9 |
| #27-37 | kelkrikipdy (SEQ ID NO: 14) | −13.3 |
| #118-127 | klgsnptsgk (SEQ ID NO: 15) | −12.2 |
| #160-170 | kkiesalrnkm (SEQ ID NO: 16) | −12.0 |
| C#227-236 | cefysenhhnp(g) (SEQ ID NO: 17) | −19.2 |
| C#418-427 | cneklqkgfpl (SEQ ID NO: 18) | −7.4 |

$_b$The summation of Kyte and Doolittle hydropathy indices for each amino acid of the sequence Hydrophilic peptides are those that have a net hydropathy index of at least about −1. Some of the hydrophilic peptides identified can also be biologically active for either bactericidal activity, endotoxin neutralizing activity, or both.

The peptides of the invention preferably have a size of about 10 amino acids to about 100 amino acids, more preferably about 10 to 40 amino acids. A peptide having about 10 amino acids is the minimum size peptide shown to have endotoxin neutralizing activity and/or bactericidal activity. Peptides with 20 to 40 amino acids include those peptides that have both endotoxin neutralizing and bactericidal activities.

Some of the peptides derived from B/PI only exhibit bactericidal activity. Other peptides have both bactericidal and endotoxin neutralizing activity. Peptides having a sequence corresponding to or derived from B/PI and that have bactericidal activity preferably include at least the amino acid sequence KWKAQKRFLK (SEQ ID NO:6). Suitable examples of peptides having bactericidal activity include:

KWKAQKRFLK (#90-99) (SEQ ID NO:6);

KISGKWKAQKRFLKMSGNF (SEQ ID NO:19) (86-104);

NANIKISGKWKAQKRFLKMSGNFDLSI (82-108) (SEQ ID NO:20); and

EFYSENHHNPKWKAQKRFLK (Hybrid) (SEQ ID NO:11)

The preferred bactericidal peptides are those that have bactericidal activity for *P. aeruginosa* at an effective dose of about $10^{-7}$M to about $10^{-9}$M, have about 10 to about 40 amino acids and include the amino acid sequence of KWKAQKRFLK. The especially preferred peptides are those including the amino acid sequence of residues 82–108 of B/PI.

Some of the peptides derived from B/PI only have endotoxin neutralizing activity. Other peptides have both bactericidal and endotoxin neutralizing activity. Suitable examples of peptides derived from or corresponding to sequences of B/PI and that have endotoxin neutralizing activity are:

VNPGVVVRISQKGLDYASQQGTAALQ (1-26) (SEQ ID NO:21);

KKIESALRNKM (160-170) (SEQ ID NO:16);

EFYSENHHNP(G) (227-236) (SEQ ID NO:22);

NEKLQKGFPL (418-427) (SEQ ID NO:23); and

NANIKISGKWKAQKRFLKMSGNFDLSI (SEQ ID NO: 20) (82-108).

The preferred endotoxin neutralizing peptides neutralize endotoxin at a concentration of about $10^{-5}$M to $10^{-8}$M and have about 10 to 40 amino acids. The especially preferred peptides are peptides including amino acids 1-26 or 82-108 of B/PI.

Some peptides have both endotoxin neutralizing activity and bactericidal activity. Suitable examples of peptides derived from or corresponding to B/PI that have both biological activities include:

CEFYSENHHNPKWKAQKRFLK (Hybrid) (SEQ ID NO:12);

KWKFKQRALK (random 90-99) (SEQ ID NO:24);

NANIKISGKWKAQKRFLKMSGNFDLSI (82-108) (SEQ ID NO:20); and

KISGKWKAQKRFLKMSGNF (#86-104) (SEQ ID NO:14).

The preferred peptide having both bactericidal and endotoxin neutralizing activity has about 10 to 40 amino acids and includes at least the amino acid sequence of residues 90–99 of B/PI. The especially preferred peptide having both biological activities is the peptide including amino acid residues 82–108. The preferred peptides are also soluble in water or DMSO and are not toxic to eukaryotic cells.

B. Modifications of the Biologically Active Peptides

The biologically active peptides derived from or corresponding to regions of B/PI can also be modified in a variety of ways to form biologically active derivatives or analogs of the peptides. These modifications include addition, substitution or deletion of amino acids. Addition of amino acids includes, for example, the formation of dimers, cyclic, or hybrid peptides as well as attachment of the peptides to carrier molecules. Substitution of amino acid residues include conservative amino acid substitutions.

Peptides derived from or corresponding to regions of B/PI can be modified by the addition of amino acids. For example, cysteine residues can be added preferably at the N- and/or C-terminal ends of the peptide. However, some peptides can have at least two cysteine residues, at least one of which is not located at the N- and/or C-terminal amino acid so that upon formation of an intra chain disulfide bond, a cyclic portion of the peptide is formed. The cysteine residues can be used to form a dimer or cyclic form of the peptide. Addition of cysteine residues at the N- and/or C-terminal end of the peptide can also result in enhanced bactericidal activity of peptides including amino acid sequence KWKAQKRFLK (SEQ ID NO:6). While not meant to limit the invention in any way, it is believed the enhancement of biological activity is not dependent on disulfide bond formation as elimination of a free reduced sulfhydryl group did not decrease biological activity.

Suitable examples of peptides that have biological activity and have N- and/or C-terminal cysteine residues and can form either dimers or cyclic compounds include:

CKWKAQKRFLK (C#90-99) (SEQ ID NO:7);

CKISGKWKAQKRFLK (C#86-99) (SEQ ID NO:10) or (dimer of C#86-99) (SEQ ID NO:10);

CKWKAQKRFLKC (C#90-99C) (SEQ ID NO:25);

Cyclic CKWKAQKRFLKC (cyclic C#90-99C) (SEQ ID NO:40);

KWKAQKRFLKC (#90-99C) (SEQ ID NO:26);

CKWKAQKRFLKMSG (C#90-102) (SEQ ID NO:27);

CEFYSENHHNPKWKAQKRFLK (Chybrid) (SEQ ID NO:12);

CEFYSENHHNP(G) (C#227-236) (SEQ ID NO:17);

CNEKLQKGFPL (C#418-427) (SEQ ID NO:18);

CNANIKISGKWKAQKRFLKMSGNFDLSIC (C#82-108C) (SEQ ID NO:28); and

CKISGKWKAQKRFLKMSGNFC (C#86-104C) (SEQ ID NO:29).

The especially preferred peptide modified with an N- and/or C-terminal cysteine is one that includes the amino acid sequence KWKAQKRFLK (SEQ ID NO:6), such as C#90-99C, C#82-108C or C#86-104C in linear or cyclic form.

Peptides including cysteine residues can form either dimers or cyclic compounds under conditions that favor formation of intrachain or interchain disulfide bonds. If the peptide contains at least one cysteine group either internally or at the N- and/or C-terminal amino acid, dimers can be formed under conditions that favor interchain disulfide bond formation. Interchain disulfide bonds are favored when peptide contains a single cysteine residue and is present in at a high enough concentration that dimers can readily be formed, preferably about 3 mM. Peptides having N- and C-terminal cysteines or one N- or C-terminal cysteine and one internal cysteine can form cyclic compounds under conditions that favor the formation of intrachain disulfide bonds. Intrachain disulfide bonds are favored when the peptide has at least 2 cysteine residues and is present at a dilute concentration preferably such as 0.1 mg/ml (1 uM or less) or less.

When the peptide has one N- or C-terminal cysteine and an internal cysteine residue, a peptide with cyclic portion can be formed, the cyclic portion preferably has about 10 amino acids to 40 amino acids and includes the amino acid sequence:

KWKAQKRFLK (SEQ ID NO:6).

When the cysteine residues are at the N- and C-terminals of the peptide, a cyclic peptide if formed, preferably having about 10 to 40 amino acids and the amino acid sequence:

KWKAQKRFLK (SEQ ID NO:6).

The especially preferred cyclic peptides have both bactericidal and endotoxin neutralizing activity and the sequence:

CKISGKWKAQKRFLKMSGNFC (C86-104C) (SEQ ID NO:29),

CKWKAQKRFLKC (C90-99C) (SEQ ID NO:25), or

CNANIKISGKWKAQKRFLKMSGNFDLSIC (C82-108C) (SEQ ID NO:28).

Addition of amino acid residues can also include coupling of the biologically active peptides to a larger molecular weight carrier protein to form a peptide conjugate. Coupling of the peptide can take place with addition of an amino acid, preferably cysteine or glycine, at the N- and/or C-terminus of the peptide to serve as a point of attachment to the carrier. Attachment of peptides to carrier molecules is conducted by standard methods known to those of skill in the art. Alternatively, the peptide can be attached directly to the carrier. The carrier molecule is a large molecular weight molecule, such as keyhole limpet hemocyanin (KLH) or bovine serum albumin (BSA). Attachment of the peptide can occur at multiple locations on the carrier molecule. These peptide conjugates can have biological activity similar to that of the corresponding unconjugated peptide and/or can be useful in pharmaceutical compositions or for formation of monoclonal antibodies to biologically active peptides derived from or corresponding to B/PI.

Additionally, amino acids or peptides can be combined with one another to form hybrid peptides. Hybrid peptides include those that have amino acid sequences from two different regions of the B/PI molecule as well as fusion proteins such as a peptide fused to another protein such as B-galactosidase. For example, a peptide having bactericidal activity can be combined with a peptide having endotoxin neutralizing activity to form a hybrid peptide. A hybrid peptide so formed has at least one biological activity and preferably has both bactericidal and endotoxin neutralizing activity. The hybrid peptide can be formed by the formation of disulfide bonds between peptides having two different amino acid sequences or by the formation of a peptide bond between the N-terminal amino acid of one peptide and the C-terminal amino acid of the other peptide. A hybrid peptide can also include a cyclic portion as described previously.

The hybrid peptide preferably includes an endotoxin neutralizing peptide having an amino acid sequence selected from the group consisting of:

CEFYSENHHNP (C#227-236) (SEQ ID NO:30);

VNPGVVVRISQKGLDYASQQGTAALQ (1-26) (SEQ ID NO:21);

CVNPGVVVRISQKGLDYASQQGTAALQ (C1-26) (SEQ ID NO:31); and

SDSFKIKHLGKGHYSFYSMDIREFQ (#38-62) (SEQ ID NO:32).

The hybrid peptide preferably also includes a bactericidal peptide having a sequence selected from the group consisting of:

KWKAQKRFLK (90-99) (SEQ ID NO:6);

CKWKAQKRFLKC (C90-99C) (SEQ ID NO:25);

NANIKISGKWKAQKRFLKMSGNFDLSI (82-108) (SEQ ID NO:20);

CNANIKISGKWKAQKRFLKMSGNFDLSIC (C82-108C) (SEQ ID NO:28);

CKISGKWKAQKRFLKMSGNFC (C86-104C) (SEQ ID NO:29); and

KISGKWKAQKRFLKMSGNF (86-104) (SEQ ID NO:19).

Hybrid peptides can be further modified by addition of amino acids such as cysteine at the N- and/or C-terminal ends or the formation of cyclic peptides or dimers.

Modifications can also include amino acid substitutions in the sequence of the biologically active peptide. Amino acid substitution can be made as long as the substitutions do not eliminate the biological activity of the peptide. Conservative amino acid substitutions typically can be made without affecting biological activity. Conservative amino acid substitutions include substitution of an amino acid for another amino acid of the same type. Types of amino acids include: (1) basic amino acids such as lysine, arginine, and histidine; (2) hydrophobic amino acids such as leucine, isoleucine, valine, phenylalanine, and tryptophan; (3) non-polar amino acids including alanine, valine, leucine, isoleucine, proline, and methionine; (4) polar amino acids such as serine, threonine, cysteine, tyrosine, asparagine, and glutamine; and (5) positively charged amino acids such as aspartic and glutamic acid. For example, the 93rd amino acid in a peptide having a sequence corresponding to amino acids 90–99 of B/PI can either be alanine, phenylalanine or tryptophan without effecting the bactericidal activity of the peptide.

The effect of other amino acid substitutions or deletions on biological activity can be determined by predicting the effect of the alteration in amino acid sequence on the confirmation or tertiary structure of the peptide using currently available molecular modeling methods or by X-ray crystallography. A peptide having bactericidal or bactericidal and endotoxin neutralizing activity preferably includes at least an amino acid sequence equivalent KWKAQKRFLK (SEQ ID NO:6). An equivalent amino acid sequence to residues 90–99 of B/PI means it is the same sequence or a sequence with a modifications such that the tertiary structure and/or functional activity of the peptide is maintained. For example, a peptide having amino acids corresponding to those of residues 90–99 of B/PI can obtained with the sequence of those residues in random order. For example, bactericidally active peptides having the following sequence:

WKKFKQRALK (SEQ ID NO:35)

KKKWFRLAKQ (SEQ ID NO:36) and

KWKFKKRALK (SEQ ID NO:37)

retain biological activity. In another example, a linear peptide including amino acid residues 90–99 of B/PI modified by N- and C-terminal cysteine residues was converted from a bactericidal peptide to one that has both bactericidal and endotoxin neutralization upon formation of a cyclic peptide.

While not meant to limit the invention in any way, it is believed that amino acid modifications (i.e., additions, substitutions or deletions) can be made to a peptide having bactericidal activity as long as those changes do not change formation of an amphipathic sequence including the amino acids KWKAQKRFLK (SEQ ID NO:6). An amphipathic sequence is one that has positively charged amino acids (+) alternating with one or more (i.e., about 2–3 amino acids) hydrophobic or non-charged amino acids(−). The sequence typically does not have any negatively charged amino acids and preferably includes about 3–6 positively charged amino acids, more preferably 4–5 positively charged amino acids. optionally, the amphipathic sequence includes at least two positively charged amino acids adjacent to one another to form a bend in the amphipathic sequence when in the conformation of a loop. Examples of peptides with amphipathic sequences including amino acids KWKAQKRFLK (SEQ ID NO:6) of B/PI and that have bactericidal activity include:

| |
|---|
| KWKAQKRFLK (#90-99) (SEQ ID NO: 6) |
| +0 +00++00+ |
| WKKFKQRALK (rand. #90-99) (SEQ ID NO: 35) |
| 0 ++0+0+00+ |
| KKKWFRLAKQ (rand. #90-99) (SEQ ID NO: 36) |
| +++0 0+00+0 |
| KWKFKQRALK (rand. #90-99) (SEQ ID NO: 24) |
| +0 +0+0+00+ |
| KKKFFRLAKQ (rand. #90-99) (SEQ ID NO: 38) |
| +++00+00+0 |
| KKKAFRLAKQ (rand. #90-99) (SEQ ID NO: 39) |
| +++00+00+0 |

Bactericidal peptides having these sequences can be combined with other amino acids to form cyclic compounds or hybrid compounds having both bactericidal and endotoxin neutralizing activities.

Biologically active peptides or derivatives or analogs derived from or corresponding to B/PI can be prepared by automated peptide synthesis or by recombinant DNA technology.

C. Preparation of Biologically Active Peptide Derived from or Corresponding to B/PI Given the amino acid sequence information disclosed herein for B/PI and the state of art in solid phase protein synthesis, essentially pure biologically active peptides can be obtained via chemical synthesis. The principles of solid phase chemical synthesis of peptides are well known in the art and may be found in general texts in the area such as Duchas H and Penny C., *Bioorganic Chemistry*, (1981) Springer-Verlag, NY at pages 54–92. For example, peptides may be synthesized by solid phase methodology utilizing fluorenylmethyoxycarbonyl chemistry on a Miligram/

Biosearch 9600 peptide synthesizer. Butoxycarbonyl (BOC) amino acids and other reagents are commercial available from Advanced Chemtech, Louisville, Ky. and Millipore Co., Marlboro, Mass. and other chemical supply houses. Sequential batch chemistry using double couple protocols can be applied to starting p-methylbenzyl hydroamine resins for the production of C-terminal carboxyamides. For the production of C-terminal acids, the corresponding PAM resin is used. Asparagine, glutamine and arginine are coupled using free formed hydroxybenzotriazyl esters. Side chain protecting groups may be used to form amino acids such as arginine, aspartic acid, glutamic acid, serine, threonine, and tyrosine. BOC de-protection may be accomplished with trifluoroacetic acid and methylene chloride. Following completion of synthesis, the peptides may be deprotected and cleaved from the resin with hydrogen fluoride (HF) containing 10% metacresol. Cleavage of the side chain protecting groups and of the peptide from the resin is carried out at 0° C. or below for 30 minutes, followed by 30 minutes at 0° C. After removal of the HF, the peptide/resin is washed with ether and the peptide extracted with glacial acetic acid and lyophilized.

Lyophilized crude peptide can be further isolated and purified using column chromatography methods, such as high pressure liquid chromatography. Isolation of the peptides can be accomplished using reverse phase HPLC on a C-18 column with an elution gradient of 0–60% acetylnitrile with 0.1% trifluoroacetic acid in water. Isolated peptides can also then be subjected to gel filtration using a column such as a Sephadex G-25 column. The purity of the peptides can be verified by reverse phase HPLC. Confirmation of the amino acid sequence of the peptides can be obtained standard amino acid analysis.

Once the peptides have been synthesized and isolated, they can be further modified by the formation of dimers, cyclic compounds and by conjugation to carrier molecules. Formation of dimers can be preferably accomplished when peptides having one cysteine residue are present at a concentration of about 3 mM and are stirred under oxidizing conditions. Formation of cyclic peptides can be accomplished using standard methods as described by Rustici et al., *Science* 259:361 (1993). Peptides having at least 2 cysteine residues can be cyclized by air oxidation with continuous stirring under conditions which favor the formation of intrachain disulfide bridges (i.e., concentration of 0.1 mg/ml (1 uM) or less). Cyclic peptides can also be purified by reverse phase HPLC with a linear methanol in water gradient of 20–80% and identified as a single peak that elutes earlier than the linear peptide. Dimers can also be isolated by HPLC and elute as a single peak later than the linear peptide. Oxidation of the thiol groups of cysteine residues can be ascertained by use of Ellman's reagent.

The peptides can also be conjugated to larger molecular weight carrier proteins such as keyhole limpet hemocyanin (KLH) or bovine serum albumin (BSA) or ovalbumin. Peptides can be conjugated to the carrier proteins using a standard method such as activation of the carrier molecule with a hetero bifunctional sulfosuccinimidyl 4-(n-maleimidomethyl) cyclohexane-1-carboxylate reagent. Crosslinking of activated carrier to a peptide can occur by reaction of the maleimide group of the carrier with the sulfhydryl group of a peptide containing a cysteine residue. Conjugates can be separated from free peptide through the use of gel filtration column chromatography.

For large scale preparation of the peptides derived from or corresponding to sequences of the B/PI, production by recombinant DNA technology methods may be desirable. Standard recombinant DNA technology methods are known to those of skill in the art and are described in texts such as *A Guide to Molecule Cloning: A Laboratory Manual* by Maniatis et al., Cold Spring Harbor, N.Y. (1989).

The general scheme for preparation of recombinant peptides derived from B/PI is as follows: (1) obtain a DNA sequence coding for the peptide either from a naturally occurring sequence, a cDNA sequence, or a synthetic or semi-synthetic sequence coding for B/PI; (2) modifying the DNA sequence to code for a modified peptide like, for example, including an N- and/or C-terminal cysteine; (3) amplifying the DNA sequence and combining the sequence with transcriptional and translational control regions functional in a host cell; and (4) transforming a host cell and isolating the recombinant peptide produced therein.

The DNA sequence coding for a peptide derived from or corresponding to amino acid sequences of B/PI can be wholly synthetic or the modification of a native DNA or cDNA sequence coding for B/PI. A DNA or cDNA sequence that encodes native B/PI is shown in FIG. 4 or FIG. 8 and can be used as starting material to obtain a DNA sequence coding for a biologically active peptide derived from B/PI.

A synthetic sequence coding for a biologically active peptide of B/PI can be constructed by techniques well known in the art and as described by Brown et al., *Methods in Enzymology*, 68:109–151 (1979). For example, DNA sequences encoding a peptide having the amino acid sequence of residues 82–108 of B/PI can be designed taking into account the known codon usage for a particular host cell and by reference to the DNA or cDNA sequence coding for B/PI at those amino acid residues. It will be understood by those of skill in the art that owing to the degeneracy of the genetic code, a sizeable yet definite number of DNA sequences can be constructed to code for peptides having an amino acid sequence derived from or corresponding to regions of B/PI. Once designed, the sequence can be synthesized using commercially available DNA synthetic technology.

Alternatively, a DNA sequence encoding a peptide derived from B/PI can be obtained from a DNA or cDNA sequence coding for B/PI by subcloning a restriction fragment including a DNA sequence coding for the desired peptide. The recognition sequences for restriction enzymes are known to those of skill in the art and based upon the DNA sequence of FIG. 4, one of skill in the art can select the restriction enzymes that will result in a fragment including a DNA sequence coding for the desired peptide.

In another method, a DNA sequence coding for a peptide derived from B/PI can be obtained by amplification of a selected sequence using polymerase chain reaction (PCR). Primers can be prepared which hybridize to the 5' and 3' ends of the region of the DNA sequence coding for the desired peptide. Primers can be designed using known principles and synthesized using automated synthesis. Examples of several primers are shown in FIG. 4. Amplification and isolation of the desired DNA sequence can be accomplished using standard PCR techniques.

Once a DNA sequence encoding the desired peptide is obtained, it can be modified by standard methods. For example, DNA sequences encoding various restriction sites can be added onto either or both the 5' and 3' ends of the sequence to provide for ease of cloning. Other modifications include adding DNA coding sequence for additional N-terminal or C-terminal amino acids such as a DNA sequence coding for cysteine or methionine or for stop codons. These modifications can be readily accomplished with PCR and appropriately designed primers. DNA sequences including changes such as amino acid substitution or deletions can be prepared either by automated synthesis, by site specific mutagenesis, or by combining a synthetic DNA sequence coding for the modified portion of the peptide with a cDNA or DNA sequence for the peptide.

Once the DNA sequence coding for the desired peptide is obtained, it can be inserted into any one of the many appropriate and commercially available DNA expression vectors through the use of appropriate restriction endonucleases. See generally Maniatis, cited supra. The particular endonucleases involved will be dictated by restriction endonuclease sites in the expression vector. The DNA sequences coding for the peptide are inserted in frame and operably linked to transcriptional and translational control regions which are present in the vector and are functional in the host cell. Appropriate transcriptional and translational control regions are known to those of skill in the art and are present in publicly available expression vectors. The DNA sequence coding for the peptide can be inserted into a system that results in expression of fusion protein including a protein such as B-galactosidase.

Figure 7:
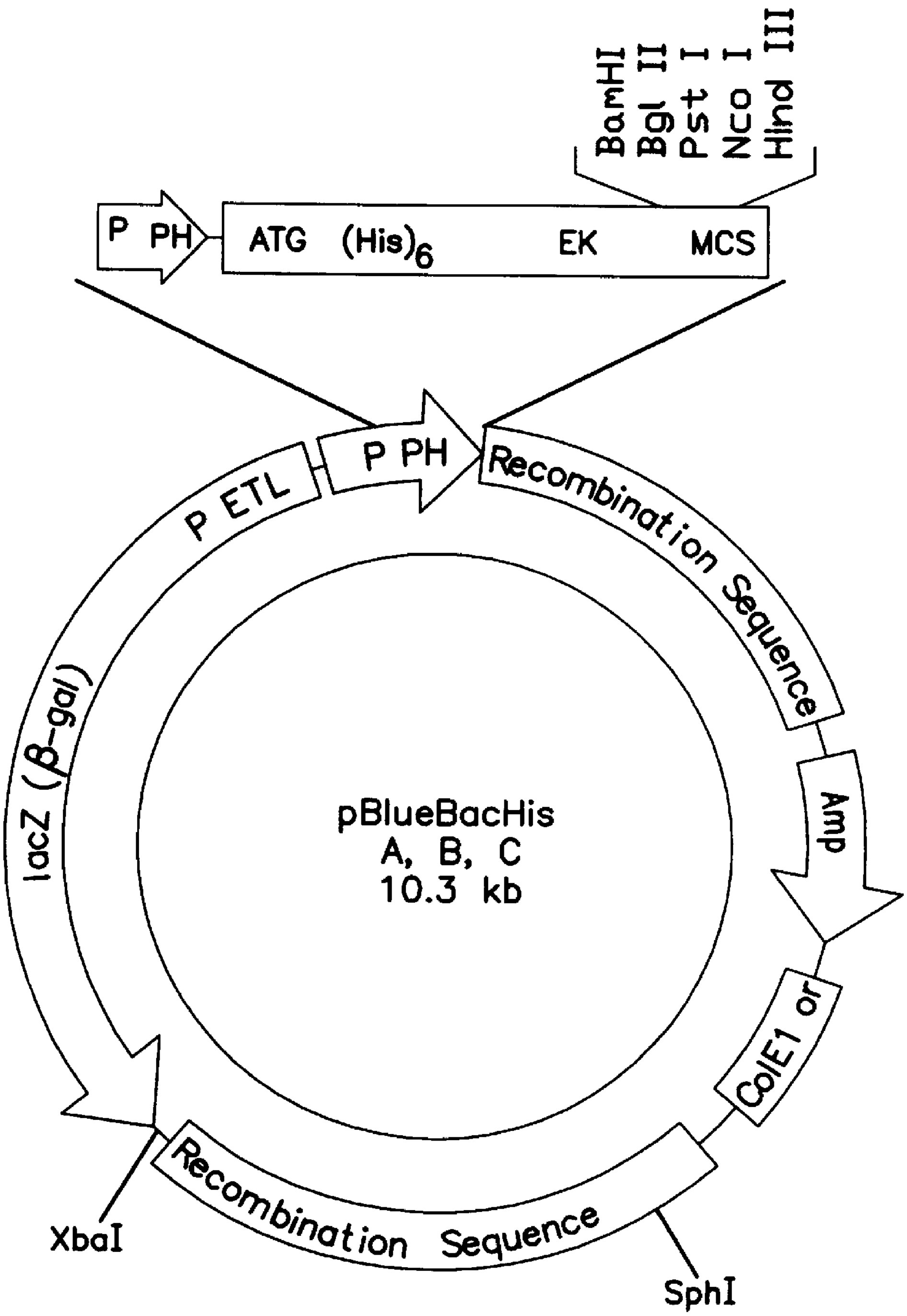
FIG. 7 is a restriction map of the Bluebac His III vector.

A variety of expression vectors useful for transforming prokaryotic and eukaryotic cells are well known in the art. See the *Promega Biological Research Products* catalog (1992). An expression system that is especially preferred is a baculovirus transfer vectors pVC1393 or Bluebac His III vector (Invitrogen Corp., San Diego, Calif.). Co-infection of insect cells with the recombinant transfer vector including a DNA sequence coding for a peptide derived from B/PI and the wild type baculovirus results in the expression of a recombinant product such as B/PI or peptides derived from B/PI under the control of the promoter of the polyhedron gene. A partial restriction map of the Bluebac His III vector is shown in FIG. 7.

Recombinant virus can be identified by formation of visibly different plaque morphology. Cells producing recombinant virus can also be detected by expression of a B-galactosidase fusion protein. Plaques with the highest level of expression of the peptide can also be detected immunologically or by hybridization to a probe that is specific for the DNA sequence coding for the desired peptide. Selected recombinant viruses can be plaque purified and can be amplified for large scale production of the peptide in SF9 insect cells. The recombinant peptides can be isolated from insect cell lysates, and peptides can be isolated by immunoaffinity chromatography and/or reverse phase HPLC.

D. Methods for Treating a Bacterial Infection

The invention also provides methods for treating a bacterial infection. The method involves a step of administering to an animal an amount of pharmaceutical composition effective to inhibit the bacterial infection. The pharmaceutical composition comprises a bactericidal peptide or an endotoxin neutralizing peptide having an amino acid sequence derived from or corresponding to a peptide from B/PI and preferably includes the amino acid sequence KWKAQKRFLK (SEQ ID NO:6). The peptide is in an admixture with a pharmaceutically acceptable carrier and can be administered in a variety of ways to effectively treat bacterial infections.

A bactericidal peptide is derived from or corresponds from a peptide from B/PI. The peptide can kill bacteria such as *Pseudomonas spp., E. coli B*, and Staphylococcus. The bactericidal peptide preferably is about 10–100 amino acids long, and more preferably about 10–40 amino acids long. The peptide preferably includes the amino acid sequence KWKAQKRFLK (SEQ ID NO:6)and can be linear cyclic, dimer or hybrid form of the peptide. The peptide also is preferably soluble in water or solvent such as DMSO has a half-life in vivo of about 0.5 hours to about 5 hours. The especially preferred peptides are those including the amino acid sequence:

CKWKAQKRFLKC (SEQ ID NO:25);

CNANIKISGKWKAQKRFLKMSGNFDLSIC (SEQ ID NO:28); and

CKISGKWKAQKRFLKMSGNFC (SEQ ID NO:29)

in linear or cyclic form.

Another particularly preferred peptide is an amino acid sequence from B/PI taken from residues 80–109 and residues 82 to 108 respectively:

ISNANCKISGKWKAQKRFLKMSGNFDCSI (SEQ ID NO:61)

NANCKISGKWKAQKRFLKMSGNFDCSI (SEQ ID NO:62)

These peptides and others encompassing these amino acids, incorporate a cysteine into the internal regions of the peptide sequence. In SEQ ID NO:61 and SEQ ID NO:62, the cysteine replaces an isoleucine at amino acid 85 and a second cysteine replaces leucine at amino acid 106. This peptide can be used in either a linear or a cyclic form and examples of both linear and cyclic peptides with internal cysteine residues are discussed in Example 8. Example 8 indicates that these peptides are useful for treating bacterial infection and to neutralize the effect of endotoxin.

The effective amount of a peptide for treating a bacterial infection will depend on the bacterial infection, the location of the infection and the peptide. An effective amount of the peptide is that amount that diminishes the number of bacteria in the animal and that diminishes the symptoms associated with bacterial infection such as fever and pain. The effective amount of a peptide can be determined by standard dose response methods in vitro and an amount of peptide that is effective to kill at least 50–100% of the bacteria ($LD_{50}$) and more preferably about 60–100% of the bacteria would be considered an effective amount.

Alternatively an effective amount of the peptide for treating a bacterial infection can be determined in an animal system such as a mouse. Acute peritonitis can be induced in mice such as outbred Swiss webster mice by intraperitoneal injection with bacteria such as *Pseudomonas aeruginosa* as described by Dunn et al., *Surgery*, 98:283 (1985); Cody et al., *Internal Surgical Research*, 52:315 (1992). Different amounts of the peptide can injected at one hour intravenously prior to the injection of the bacteria. The percentage of viable bacteria in blood, spleen and liver can be determined in the presence and absence of the peptide or other antibiotics. While not meant to limit the invention, it is believed that bactericidal peptide could also enhance the effectiveness of other antibiotics as erythromycin by increasing the uptake of the antibiotics by the bacteria.

The bactericidal peptide can be used to treat infections with *Pseudomonas spp., E. coli* strains, other gram-negative bacteria such as Salmonella, *Proteus mirabilis* and gram positive *S.aureus*. The bactericidal peptide is preferably used to treat infections with *Pseudomonas spp.*, both rough and smooth strains, mucoid and nonmucoid strains of Pseudomonas. The infection can be systemic or surface infection, such as on the skin or mucosal membranes.

The bactericidal peptide can be combined with a variety of physiological acceptable carriers, diluents or excipients known to those of skill in the art. For example, for parenteral administration, isotonic saline is preferred. For topical administration a cream, including a carrier such as dimethylsulfoxide (DMSO) is preferred. Other suitable carriers include alcohol, phosphate buffered saline and other balanced salt solutions.

The peptide can be administered in a variety of ways, including intravenously, topically, orally and intramuscularly to a variety of animals, including humans, mice and rabbits. The peptides can be administered as a single dose or in multiple doses. Preferably the dose is an effective amount as determined by the standard methods described herein and includes about 1 microgram to about 1,000 micrograms per treatment, more preferably about 50 to about 250 micrograms per treatment.

E. Method for Treating Endotoxin Shock

The invention also provides a method for treating endotoxin shock. The steps of the method involve administering a pharmaceutical composition to an animal in an amount sufficient to diminish the symptoms of endotoxin shock, including release of TNFα into the blood stream, fever, decrease in blood pressure and intravascular coagulation. The pharmaceutical composition includes a peptide derived from or corresponding to peptides from B/PI and can neutralize endotoxin. The endotoxin neutralizing peptide is in admixture with a pharmaceutically acceptable carrier and can be administered in a variety of ways.

An endotoxin neutralizing peptide derived from or corresponding to a peptide B/PI can neutralize endotoxin as determined by an in vitro test such as LAL or chromogenic LAL test, preferably at a concentration of about $10^{-5}$ to $10^{-8}$M. The endotoxin neutralizing peptide is about 10–100 amino acids long and preferably 10–40 amino acids long. The peptide preferably also is bactericidal and includes the amino acid sequence KWKAQKRFLK (SEQ ID NO:6) and can be a linear, cyclic, dimer or hybrid form of the peptide. The peptide is also preferably soluble in water and/or a solvent such as DMSO and has half-life in vivo of about 0.5 to 5 hours. The especially preferred peptides are those including the following amino acids sequence:

CNANIKISGKWKAQKRFLKMSGNFDLSIC (SEQ ID NO:28);

CKISGKWKAQKRFLKMSGNFC (SEQ ID NO:29); and

CKWKAQKRFLKC (SEQ ID NO:25)

in linear or cyclic form.

Another particularly preferred peptide is an amino acid sequence from B/PI taken from residues 80–109 and residues 82 to 108 respectively:

ISNANCKISGKWKAQKRFLKMSGNFDCSI (SEQ ID NO:61)

NANCKISGKWKAQKRFLKMSGNFDCSI (SEQ ID NO:62)

and other peptides having internal cysteines and including the amino acid sequence KWKAQKRFLK (SEQ ID NO:6).

The effective amount of a peptide for treating endotoxin shock can be determined by in vitro methods to determine the amount that will neutralize endotoxin. An effective amount of endotoxin neutralizing peptide is that amount that decreases the symptoms of endotoxin shock such as fever, shock and TNFA release. The amount of endotoxin neutralizing peptide that will neutralize about 50% ($ID_{50}$) of $10^{-6}$ to $10^{-9}$ gm of endotoxin can be determined using the LAL or the chromogenic LAL assay for endotoxin neutralization. The endotoxin neutralizing peptide preferably neutralizes about 50–100% of the endotoxin neutralizing activity and more preferably about 90–100%.

Alternatively, an effective amount of an endotoxin neutralizing peptide can be determined by measuring the effect of differing amounts of a endotoxin neutralizing peptide on the ability of lipopolysaccharide (LPS) to stimulate release of tumor necrosis factor alpha (TNF) from a macrophage cell line. A macrophage cell line can be incubated with LPS in the presence or absence of different amounts of endotoxin neutralizing peptide. Production of TNFα can be assayed as described by Mossman et al., *Immunological Methods*, 65:55 (1983). An inhibitory dose 50 ($ID_{50}$) can be calculated according to standard methods.

Another option for determining the effective amount of a endotoxin neutralizing peptide is to determine the amount of endotoxin neutralizing peptide that will inhibit endotoxin mediated pyrogenicity in rabbits. Samples of endotoxin and differing amounts of peptides can be mixed and incubated for about 30 minutes. The mixtures are then tested for the ability to stimulate pyrogenicity by intravenous injection into rabbits. Temperature of the rabbits is monitored over time. An inhibitory dose ($ID_{50}$) can also be calculated based upon these results by standard methods.

The endotoxin neutralizing peptide can be used to treat animals infected with gram-negative bacteria systemically and that exhibit symptoms of endotoxin shock such as fever, shock and TNFα release. The animals are typically infected with one or more gram-negative bacteria such as *Pseudomonas spp.* rough strains of *E. coli*, encapsulated *E. coli* and smooth strain *E. coli*. The endotoxin neutralizing peptide can be combined with other agents that are known and used by those skilled in the art to treat endotoxin shock.

The endotoxin neutralizing peptide can be combined with a variety of physiologically acceptable carriers, diluents or excipients known to those skilled in the art. For example, carriers, include isotonic saline, phosphate buffered saline, and other balanced salt solution that may include plasma expanders. The peptide can be administered in a variety of ways including intravenously, topically, orally and intramuscularly to a variety of animals including humans, mice and rabbits. The peptides can be administered in a single dose or multiple doses. Preferably the dose is an effective amount as determined by the methods described herein and includes about 1 ug to 1,000 ug per treatment and more preferably about 50 to 250 ugms per treatment.

F. Peptide modifications

There are a number of modifications to the peptides of this invention that can improve activity of the peptides in vivo. In a preferred example, the peptides of this invention are synthesized in their D-enantiomeric form. Biological activity of a peptide can be directly related to serum stability (Su, et al. (1991) *Horm. Metab. Res*. 22:15–21 and Leadun, et al. (1989) *J. Pharm. exp. Therapeutics* 281:439–447). To provide increased protection from serum degradation reverse D-amino acid analogues of the B/PI peptides were engineered. Most serum proteases recognize α-carbon centers and are specific for L-amino-acid enantiomers (Jameson, et al. Nature 368:744–746, 1994). D-amino acid containing peptides are more resistant to degradation. (Dintzis, et al. Proteins 16:306–308, 1993). Methods for synthesizing D-amino acids are known in the art and the D-amino acids used in this application were purchased from Advanced ChemTech(Louisville, Ky.). D-Peptides prepared from the D-amino acids were synthesized using standard peptide synthesis protocols.

Preferred reverse D-amino acid-containing peptides include a peptide corresponding to amino acids 82–108 of B/PI. Amino acids 82–108 have the following amino acid sequence:

NANIKISGKWKAQKRFLKMSGNFDLSI.

The reverse D-amino acid peptide has the sequence:

ISLDFNGSMKLFRKQAKWKGSIKINAN.

These peptides, and others, in both the L-enantiomer and the reverse D-enantiomer forms were tested for endotoxin neutralizing and bactericidal activity using the methods of Example 8.

Peptides from B/PI with internal cysteines were prepared in the reverse D-enantiomeric conformation as well. Preferred D-peptides with cysteines include SEQ ID NO:62, synthesized using D-amino acids. The reverse D-amino acid peptide (BG38D) having the reverse of SEQ ID NO:62 was tested in mice as disclosed in Example 9. The experiments demonstrated that the peptide efficiently neutralized LPS endotoxin and attenuated LPS induced cytokine secretion in vivo. The results of tests comparing peptides in the D- and L- enantiomer forms in bactericidal and endotoxin neutralizing assays is provided in the table below:

| Peptide | End. Neut. Act. at $5.0 \times 10^{-6}$M[a] Peptide | Bacteric. Act. at $1.2 \times 10^{-7}$M[b] Peptide |
|---|---|---|
| 82-108 (L) | 34.4 (n = 5) | 45.0 (n = 5) |
| 82-108 (reverse-D) | 10.0 (n = 1) | 50.9 (n = 7) |
| SEQ ID NO: 62 (L) | 39.9 (n = 8) | 54.7 (n = 9) |
| SEQ ID NO: 62 (rev.-D) | 22.0 (n = 1) | 38.8 (n = 7) |

[a]% neutralization of 0.02U (0.2 pg of endotoxin from *E. coli* O55:B5)
[b]% killing of $5 \times 10^5$ *P. aeruginosa*

This table indicates that use of D-amino acids did not significantly alter bactericidal and endotoxin neutralizing activity. These peptides have the advantage that they are resistant to protease degradation in vivo.

A second modification to the peptides is to prepare the peptides in a reverse orientation. For example, it is contemplated that peptides from the KWKAQKRFLKMS region of B/PI will be useful in reverse orientation. By reverse orientation it is meant that the peptides are synthesized following a reverse order. For example, the peptide KWKAQKRFLKMS has a reverse orientation of SMKLFRKQAKWK.

All or part of the amino acid sequence from B/PI amino acids 82–108 can be used in the reverse orientation and prepared as a peptide using standard peptide synthesis methods or recombinant methods to produce a peptide with the reverse sequence. The reverse sequence of 82-108 is NANCKISGKWKAQKRFLKMSGNFDCSI. A particularly preferred region from the amino acid sequence 82-108 corresponds to a peptide with the sequence KWKAQKRFLKMS and a preferred reverse orientation peptide from this region is SMKLFRKQAKWK. Reverse orientation peptides from B/PI are useful for inhibiting bacterial infection and endotoxin shock.

In another embodiment of this invention a variety of hybrid proteins are used to treat bacterial infections and endotoxic shock. Preferably the hybrid peptides are formed with an amino acid sequence comprising about at most amino acids 82–108 flanked by exogenous amino acid sequences, and preferably includes at least amino acids KWKAQKRFLK from B/PI and more preferably at least amino acids KWKAQKRFLKMS. By exogenous amino acid sequences it is meant that the amino acid sequences at the amino terminus, the carboxy terminus or both on the peptide are not peptide sequences natively found in the B/PI protein or are not natively found flanking the KWKAQKRFLK sequence. Two preferred peptides that include at least the peptide sequence KWKAQKRFLMS are:

HIKELQVKWKAQKRFLKMSIIVKLNDGRELSLD (SEQ ID NO:63)

ANIKLSVKWKAQKRFLKMSIIVKLNDGRELSLD (SEQ ID NO:64)

The region in bold identifies the portion of the hybrid peptide containing at least the amino acid sequence KWKAQKRFLK of peptide 82-108 of B/PI.

Hybrid peptides containing at least the amino acid sequence KWKAQKRFLK also include the peptide region in reverse orientation. An example of a preferred peptide with bactericidal and/or endotoxin neutralizing activity and having at least the amino acid sequence KWKAQKRFLK in reverse orientation category includes:

SIQDLNVSMKLFRKQAKWKIIVKLNDGRELSLD (SEQ ID NO:65)

This invention also contemplates substitutions within the hybrid peptide within the peptide sequence KWKAQKRFLK and substitutions to the peptide sequence within a hybrid peptide where the peptide sequence of at least KWKAQKRFLK is positioned in reverse orientation. A preferred peptide with these characteristics includes:

ANIKLSVEMKLFKRHLKWKIIVKLNDGRELSLD (SEQ ID NO:66)

In this peptide, the fragment from amino acids 82–108 of B/PI is configured in the reverse orientation as indicated by the peptide fragment within the hybrid highlighted in bold type. A four amino acid substitution was inserted into the middle of this peptide. The endotoxin neutralizing and bactericidal activities are provided below:

| Peptide | Endotoxin Neutral. Activity[a] $5.0 \times 10^{-6}$M | Bactericidal Activity[b] $1.2 \times 10^{-7}$M |
|---|---|---|
| SEQ ID NO: 63 | 81.3 (n = 5) | 24.9 (n = 3) |
| SEQ ID NO: 64 | 100 ED[c] | 0 ED[c] |
| | $1.2 \times 10^{-6}$ | $9.6 \times 10^{-7}$ |
| | (45.6) n = 1 | (83.5) n = 3 |
| SEQ ID NO: 65 | 42.8 (n = 3) | 32.0 (n = 3) |
| SEQ ID NO: 66 | 100 ED[c] | 0 ED[c] |
| | $1.2 \times 10^{-6}$ | $9.6 \times 10^{-7}$ |
| | (70.6) n = 4 | (28.1) n = 3 |

[a]% neutralization of 0.02U (0.2 pg of endotoxin from *E. coli* O55:B5)
[b]% killing of $5 \times 10^5$ *P. aeruginosa*
[c]Effective Molar dose (%)

The hybrid peptides demonstrated endotoxin neutralizing activity and bactericidal activity. The hybrid peptides were prepared using standard peptide synthesis methods but those skilled in the art will recognize that the peptides can also be produced by recombinant methods known to those skilled in the art using standard commercial expression vectors that are introduced into a suitable expression vector-matched host, such as *E. coli* or a eukaryotic expression vector system introduced into a suitable eukaryotic cell.

The flanking sequences of the hybrid proteins can be derived from random sequences or sequences from portions of proteins. The flanking sequences are believed to enhance the stability of the peptide.

Although hybrid peptides are disclosed above, it is also possible to create hybrid protein or polypeptide, meaning that a peptide having the sequence of 82-108 of B/PI can be linked, through chemical conjugation or as the product of recombinant fusion protein synthesis, with a larger exogenous protein. A preferred polypeptide is the constant domain of immunoglobulin, and preferably the constant domain of IgG, and in particular the constant domain of IgG2b.

The modified peptides can be used to treat bacterial infections or endotoxic shock with or without a carrier.

Peptides are preferably introduced as bactericidal agents or endotoxin-neutralizing agents with a carrier, such as KLH, serum albumin, or a carrier suitable for human use. The peptides can be used to treat a gram negative bacterial infection or endotoxic shock by administering an amount of a pharmaceutical composition effect to inhibit the bacterial infection or neutralize endotoxin to an animal where the pharmaceutical composition comprises a peptide demonstrating gram negative bactericidal activity or endotoxic neutralizing activity according to the limitations of this disclosure in a pharmaceutically acceptable carrier. Methods for coupling peptides to carriers such as KLH are discussed supra and in Example 1, below.

G. Prosthetic Devices

The invention also provides for prosthetic or implantable devices that are coated with or to which a bactericidal peptide is attached. The bactericidal peptide is attached or coated on a surface of the prosthetic or implantable device in an amount effective to inhibit growth of bacteria on the surface. The bactericidal peptide is derived from or corresponds to a peptide of B/PI and preferably includes the amino acid sequence KWKAQKRFLK. The bactericidal peptide can be attached to a linking compound such as a carrier protein and then attached to the surface of prosthetic or implantable device.

A bactericidal peptide for attachment to prosthetic devices is preferably about 10–100 amino acids long and has been modified by the addition of a cysteine or glycine residue that can serve as a site of attachment to the prosthetic device. The peptide also preferably also includes the peptide sequence KWKAQKRFLK (SEQ ID NO:6) and can be a linear, cyclic, dimer or hybrid form of the peptide. The especially preferred peptides are:

CKWKAQKRFLKC (SEQ ID NO:25);

CNANIKISGKWKAQKRFLKMSGNFDLSIC (SEQ ID NO:28); and

CKISGKWKAQKRFLKMSGNFC (SEQ ID NO:29) in a linear or cyclic form.

The amount of the bactericidal peptide effective to inhibit growth on the surface can be determined by coating a surface such as an agar plate with different amounts of a bacteria and overlaying the surface with a lawn of bacteria such as *Pseudomonas spp*. The amount of a bactericidal peptide that results in a 50–100% inhibition of the bacteria and more preferably 90–100% an inhibition of growth on the surface is an effective amount.

It is contemplated that prosthetic devices could be coated with any of the peptides of this invention that include bactericidal and/or endotoxin neutralizing activity.

Types of prosthetic or implantable devices include catheters, I.V. tubing, drug-delivery pumps, cardiac pacemakers, bone replacement prosthetics and shunts used in the brain. Hydrogels such as polymethylolmethacrylamide (PMMA) can also be used for implants in the body. Devices intended for cardiac insertion include heart valves and left ventricular assist devices formed from synthetic resins such as polyurethane elastomers or from vulcanized polyolefin rubbers. As the device remains in the body, the chance of developing infection with hospital related microorganisms such as *P. cepacia* increases. Coating implantable or prosthetic devices with a bactericidal peptide can drastically reduce the rate of infection associated with the introduction of devices into the body.

Attachment of the peptide can be proceed by standard methods and will depend on the nature of the surface of the prosthetic device. Attachment of the peptide may require the presence of linking agent that can link the peptide to the surface. For a review of synthetic resins and biomaterials in prosthetic devices, See Chem. & Eng. News (Apr. 14, 1986) at pages 30–48. Preferably the attachment to the surface is a covalent attachment and does not destroy the biological activity of the peptide. Preferably the attachment is through a cysteine residue at the N and/or C-terminal end of the peptide.

Once coated the prosthetic devices can be introduced into an animal such as human.

EXAMPLE 1

Generation of Peptides from Human Neutrophil Granule Bactericidal Protein

Some short (about 9 to 35 amino acids) hydrophilic peptides based on the structure of the 55 kD bactericidal protein B/PI from human neutrophil granules were identified from the hydropathy plot of predicted 456 amino acid sequence of B/PI (Table 1). The predicted amino acid sequence was obtained from the nucleotide sequence of a cDNA clone of B/PI, as shown in FIG. 4 or FIG. 8. These peptides and other related peptides were synthesized by automated methods. The peptides prepared by automated synthesis as described below were optionally coupled to keyhole limpet hemocyanin or ovalbumin protein carriers.

Peptide Preparation

Peptides were synthesized at the University of Minnesota Microchemical Facility using a Millgren/Biosearch 9600 peptide synthesizer. All peptides were solid-phase syntesized by use of fluorenylmethoxycarbonyl chemistry. The profile of cleaved peptide was obtained by analytical high performance liquid chromatography (HPLC) (Model HP1090 from Hewlett Packard). When necessary, lyophilized crude peptides were purified by preparative reverse-phase HPLC on a C18 column with an elution gradient of 0–60% acetonitrile whit 0.1% trifluoroacetic acid in water. Crude and pure peptides were subjected to gel filtration using a 1×9 cm sephadex G25 column and pyrogen-free saline buffered with 0.008M citrate phosphate buffer, pH 7.0, as elution buffer and used to confirm results obtained at every step of the study. The purity and composition of the peptides were verified by HPLC (Beckman Model 6300). Analysis of amino acid composition of the peptides were obtained from hydrolysates prepared by treating the peptides under argon in 6N HCl for 24 hours at 110° C. The thiol groups of all peptides containing a cysteine residue were fully reduced as ascertained with Ellman's reagent using reduced glutathione as a standard.

The peptides synthesized are shown in Table 2.

TABLE 2

| Peptide Number | Code | Sequence |
|---|---|---|
| 1 | Signal | mrenmargpc (SEQ ID NO:13) |
| 2 | C#90–99 | ckwkaqkrflk (SEQ ID NO:7) |
| 3 | C#227–236 | cefysenhhnp(g) (SEQ ID NO:17) |
| 4 | C#418–427 | cneklqkgfpl (SEQ ID NO:18) |
| 5 | #90–99 | kwkaqkrflk (SEQ ID NO:6) |
| 6a | #27–37 | kelkrikipdy (SEQ ID NO:14) |
| 6b | C#27–37 | ckelkrikipdy (SEQ ID NO:41) |
| 7a | #160–170 | kkiesalrnkm (SEQ ID NO:16) |
| 7b | C#160–170 | ckkiesalrnkm (SEQ ID NO:42) |
| 8a | #86–99 | kisgkwkaqkrflk (SEQ ID NO:9) |
| 8b | C#86–99 | ckisgkwkaqkrflk (SEQ ID NO:10) |

TABLE 2-continued

| Peptide Number | Code | Sequence |
|---|---|---|
| | dimer 8b | ckisgkwkaqkrflk<br>\|<br>ckisgkwkaqkrflk |
| 9a | #90–102 | kwkaqkrflkmsg (SEQ ID NO:8) |
| 9b | C#90–102 | ckwkaqkrflkmsg (SEQ ID NO:27) |
| 10a | #118–127 | klgsnptsgk (SEQ ID NO:15) |
| 10b | C#118–127 | cklgsnptsgk (SEQ ID NO:43) |
| 11 | F1 #1–26 | vnpgvvvrisqkgldyasqqgtaalq (SEQ ID NO:21) |
| 12 | F2 #38–62 | sdsfkikhlgkghysfysmdirefq (SEQ ID NO:32) |
| 13 | F3 #63–89 | lpssqismvpnvglkfsisnanikisg (SEQ ID NO:44) |
| 14 | F4 | msgnfdlsiegmsisadl (SEQ ID NO:45) |
| 15 | F5 | ptitcsscsshinsvhvhiskskvgwliqlfh (SEQ ID NO:46) |
| 16 | F6 | mnsqvcekvtnsvssklqpyfqtlpvmtki (SEQ ID NO:47) |
| 17 | CHybrid | cefysenhhnpkwkaqkrflk (SEQ ID NO: 12) |
| | dimer 17 | cefysenhhnpkwkaqkrflk<br>\|<br>cefysenhhnpkwkaqkrflk |
| 18 | Hybrid | efysenhhnpkwkaqkrflk (SEQ ID NO: 11) |
| 19 | rand.90–99 | wkkfkqralk (SEQ ID NO:35) |
| 20a | | ckwkaqkrflkc (SEQ ID NO:25) |
| | cyclic 20a | ckwkaqkrflkc<br>(SEQ ID NO:40) |
| 20b | #90–99C | kwkaqkrflkc (SEQ ID NO:26) |
| 21 | rand. 90–99 | kkkwfrlakq (SEQ ID NO:36) |
| 22 | #82–#108 | nanikisgkwkaqkrflkmsgnfdlsi (SEQ ID NO:20) |
| 23 | C#82–108C | cnanikisgkwkaqkrflkmsgnfdlsic (SEQ ID NO:28) |
| | cyclic 23 | cnanikisgkwkaqkrflkmsgnfdlsic<br>(SEQ ID NO:33) |
| 24 | Rustici#6 | iktkkflkkt (SEQ ID NO:48) |
| 25 | Rustici#2 | ktkckflkkc (SEQ ID NO:49) |
| | cyclic 25 | cktkckflkkc<br>(SEQ ID NO:50) |
| 26 | (peptide 19) wk→kw | kwkfkqralk (SEQ ID NO:24) |
| 27 | #93 (peptide 21) w→f | kkkffrlakq (SEQ ID NO:38) |
| 28 | #93 (peptide 21) w→a | kkkafrlakq (SEQ ID NO:39) |
| 29 | #100–109 | msgnfdlsie (SEQ ID NO:51) |
| 30 | #80–89 | isnanikisg (SEQ ID NO:52) |
| 31 | #83–92 | anikisgkwk (SEQ ID NO:53) |
| 32 | #86–95 | kisgkwkaqk (SEQ ID NO:54) |
| 33 | #94–103 | qkrflkmsgn (SEQ ID NO:55) |
| 34 | #97–106 | flkmsgnfdl (SEQ ID NO:56) |
| 34b | C#97–106C | cflkmsgnfdlc<br>(SEQ ID NO:57) |
| 35 | #86–104 | kisgkwkaqkrflkmsgnf (SEQ ID NO:19) |
| 36 | C#86–104C | ckisgkwkaqkrflkmsgnfc (SEQ ID NO:29) |
| | cyclic 36 | ckisgkwkaqkrflkmsgnfc<br>(SEQ ID NO:34) |
| 37 | 82–92 | nanikisgkwk (SEQ ID NO:58) |

Peptides corresponding to different portions of the amino terminal end of the B/PI molecule were synthesized and modified in various ways. Peptides synthesized containing an N-terminal cysteine are given the designation C before the amino acid numbers. Peptides synthesized with N- and C-terminal cysteines were designated with a C before and after the amino acid numbers. Peptides can be synthesized with an internal cysteine residue. Peptides with a C-terminal cysteine have a C after the amino acid numbers. Peptides with N- and C-terminal cysteines can be cyclized as described below. Some of the peptides were dimerized as described below. Peptides containing the same amino acids as peptide #90-99 were generated randomly. Those peptides are designated rand., as shown in peptides 19, 21, 26, 27, or 28. The randomly generated peptide 21 was modified by specific replacement of tryptophane (W) at residue 93 with phenylalanine (F) (peptide 27) or alanine (A) (peptide 28). The randomly generated peptide 19 was modified at amino acid residues #90 and #91 for WK to KW (peptide 26).

Once synthesized and purified, the peptides were assayed for biological activity.

Method for Preparing Cyclic Peptides

Peptides (0.1 mg/ml (1 uM) pH 7.0) were cyclized by air oxidation with continuous stirring for 72 hours, under conditions which favor intrachain disulfide bridges. Peptides were purified by reversed-phase HPLC with a linear methanol in water gradient of 20 to 80%. A cyclic peptide eluted as a single peak earlier than the corresponding linear peptide. Amino acid composition of the peptides was confirmed by Pico-Tag analysis (Waters). Quantitation of amino groups in the peptides was as described. Mannion et al., cited supra. Oxidation of the thiol groups of cysteine residues was ascertained by Ellman's reagent. Cyclic peptides were assayed for biological activity.

Method for preparing Peptide Dimers

For preparation a dimer, 3 mM of a peptide having one cysteine residue in pyrogen free saline was dimerized by air oxidation by continuous stirring for 72 hours. Dimers were isolated by reverse phase HPLC with a linear methanol in water gradient of 20–80%. Dimers eluted as a single peak at a time later than the corresponding monomers.

Conjugation of Peptides to Protein Carriers

Peptides were conjugated to Keyhole Limpet hemocyanin or ovalbumin carrier proteins which had been activated with the hetero bifunctional sulfosuccinimidyl 4-(N-maleimidomethyl)cyclohexane-1-carboxylate reagent. Cross-linking of activated carrier to peptide was due to the reaction of the maleimide group of the carrier with the sulfhydryl group of the peptide and according to the manufacturer's instructions (monograph #77108, Pierce Chemical Company, Rockford, Ill.). Conjugates were separated from free peptide with a 1×9 cm Sephadex G25 column, rather than the column provided by the manufacturer. Conjugates and unconjugated protein carriers were hydrolyzed and the amino acid composition determined as described above. Using the amino acid composition of carrier compared with conjugate, the stoichiometry of peptide to carrier and the molecular mass of each conjugate was determined. Assuming a molecular mass of 70 kD for KLH and of 45 kD for ovalbumin, the molar concentration of peptide in each conjugate was calculated by the difference. Peptides conjugated to protein carriers were also assayed for biological activity.

Purification of B/PI

B/PI was purified in three column chromatography steps as previously described. Wasiluk et al., *Infection and Immunology*, 9:4193 (1991). In the final step, the sample was applied to a 1×180 cm molecular sieving column of Toyopearl HW55S (TosoHaas, Philadelphia, Pa.) which had been equilibrated with 0.05M glycine buffer, containing 0.5M NaCl (pH 2.5). Protein concentration was determined according to Hartree, *Anal. Biochem.*, 48:422–427 (1972). Purity was confirmed by visualization of a SDS polyacrylamide gel following electrophoresis of 1 μg of purified B/PI protein and silver staining of the gel, also as previously described.

EXAMPLE 2

ASSAY OF THE SYNTHETICALLY PRODUCED PEPTIDES FOR BACTERICIDAL ACTIVITY

The synthetically produced peptides were assayed for bactericidal activity against *Pseudomonas aeruginosa*, type 1, *P. cepacia* ATCC 25608, *E. coli B*, and *Staphylococcus aureus* 502A by standard methods.

Bacteria

*Pseudomonas aeruginosa* type 1 is a clinical isolate maintained in the laboratory since 1972. The isolate remains a smooth strain and was serotyped by the scheme of Homma. Homma, *Jpn. J. Exp. Med.*, 46:329 (1976). A rough strain *E. coli B* and *S. aureus* 502A were obtained from Paul Quie, University of Minnesota. The characteristics of the *S. aureus* strain have been described in Shinefield et al., *Amer. J. Dis. Chil.*, 105:646 (1963). *Pseudomonas cepacia* ATCC 25608 was purchased from the American Type Culture Collection in 1980. *S. aureus* and *E. coli* were maintained on nutrient agar plates and the Pseudomonas strains were maintained on blood agar plates.

Bactericidal Assay

Pyrogen-free solutions were used throughout this assay and all methods which follow. Log phase bacteria were prepared from a culture in brain heart infusion broth as previously described except that bacteria were washed and resuspended in saline with adjustment to an optical density at 650 nm which would yield $3\times10^8$ CFU/ml. Bacteria were then diluted 1:10 in 0.08M citrate phosphate buffer, pH 5.6 or pH 7.0, for use in the assay. *S. aureus* rapidly lost viability in the pH 5.6 buffer and was studied only at pH 7.0. Bactericidal activity was determined by dose response and where an LD50 is indicated, it was determined by linear regression.

The bactericidal activity of three of the synthetic peptides against four different bacteria was compared with the 55 kD B/PI protein. The results are shown in Table 3.

TABLE 3

Bactericidal Activity of B/PI and of Synthetic Peptides Related to B/PI

| | % Killing of 5 × $10^6$ Bacteria | | | | | | | |
|---|---|---|---|---|---|---|---|---|
| | B/PI (4.1 × $10^{-9}$ M) | | C#90–99 (1.5 × $10^{-6}$ M) | | C#227–236 (1.2 × $10^{-4}$ M) | | C#418–427 (1.2 × $10^{-4}$ M) | |
| Bacteria | pH 5.6 | pH 7.0 | pH 5.6 | pH 7.0 | pH 5.6 | pH 7.0 | pH 5.6 | pH 7.0 |
| *P. aeruginosa* | 50 ± 5 | 35 ± 3 | 83 ± 13 | 83 ± 15 | 0 | 0 | 0 | 0 |
| *P. cepacia* | 0 | 0[b] | 0 | 0[c] | 0 | 0 | 0 | 0 |
| *E. coli* | 35 ± 4 | 25 ± 5 | 0 | 0[d] | 0 | 0 | 0 | 0 |
| *S. aureus* | — | 0[b] | — | 0[e] | — | 0 | — | 0 |

[a]Values shown are the mean ± one standard error for three experiments

[b]*P. cepacia* and *S. aureus* were not killed at a concentration 20-fold higher (approximately 5 μg protein/ml)

[c]78% of *P. cepacia* were killed at 1.5 × $10^{-5}$ M, pH 7.0, and 80% at pH 5.6

[d]90% of *E. coli* were killed at 1.5 × $10^{-5}$ M, pH 7.0, and 98% at pH 5.6

[e]95% of *S. aureus* were killed at 3 × $10^{-5}$ M, pH 7.0

The bactericidal activity of the C#90-99 peptide towards four different bacteria is compared in Table 3 with the activity of two other peptides, C#227-236 and C#418-427 of the mature B/PI molecule. The latter two peptides were synthesized with an amino-terminal cysteine for the comparison with C#90-99 and so that they could be coupled to protein carrier molecules through the thiol group. The C#227-236 sequence occurs at the halfway point of the molecule of B/PI. This peptide was synthesized with a carboxy-terminal glycine to facilitate cleavage from the resin after synthesis of the peptide.

The C#227-236 and C#418-427 peptides were not bactericidal for any of the four bacteria shown in Table 3. The highest dose of these peptides tested was $1.2\times10^{-4}$. As shown in Table 3, B/PI was equally bactericidal toward *P. aeruginosa* and a rough strain *E. coli* at $4.1\times10^{-9}$M (approximately 0.2 μg protein/ml). There was a small but reproducible loss of activity at pH 7.0, compared to pH 5.6. *P. cepacia* and *S. aureus* resisted bactericidal activity at $9.1\times10^{-8}$M of B/PI, or approximately a 20-fold higher protein concentration than that which killed *P. aeruginosa*. By comparison with B/PI, the C#90-99 peptide killed *P. aeruginosa* when tested at $1.5\times10^{-6}$M (2.1 μg of peptide/ml). *E. coli* and *P. cepacia* were killed at a peptide concentration of C#90-99 which was 10 times higher than the peptide concentration which killed *P. aeruginosa*. Killing of *S. aureus* by C#90-99 occurred at 20 times the concentration which killed *P. aeruginosa*.

The hydrophilic peptides #27-37, #118-127 and #160-170 shown in Table 2 were not bactericidal at $1.2\times10^{-4}$M for any of the bacteria of this study (data not shown). A peptide corresponding to the first 10 amino acids of the signal sequence for B/PI also was not bactericidal and data is not shown for studies of this peptide.

Figure 1:
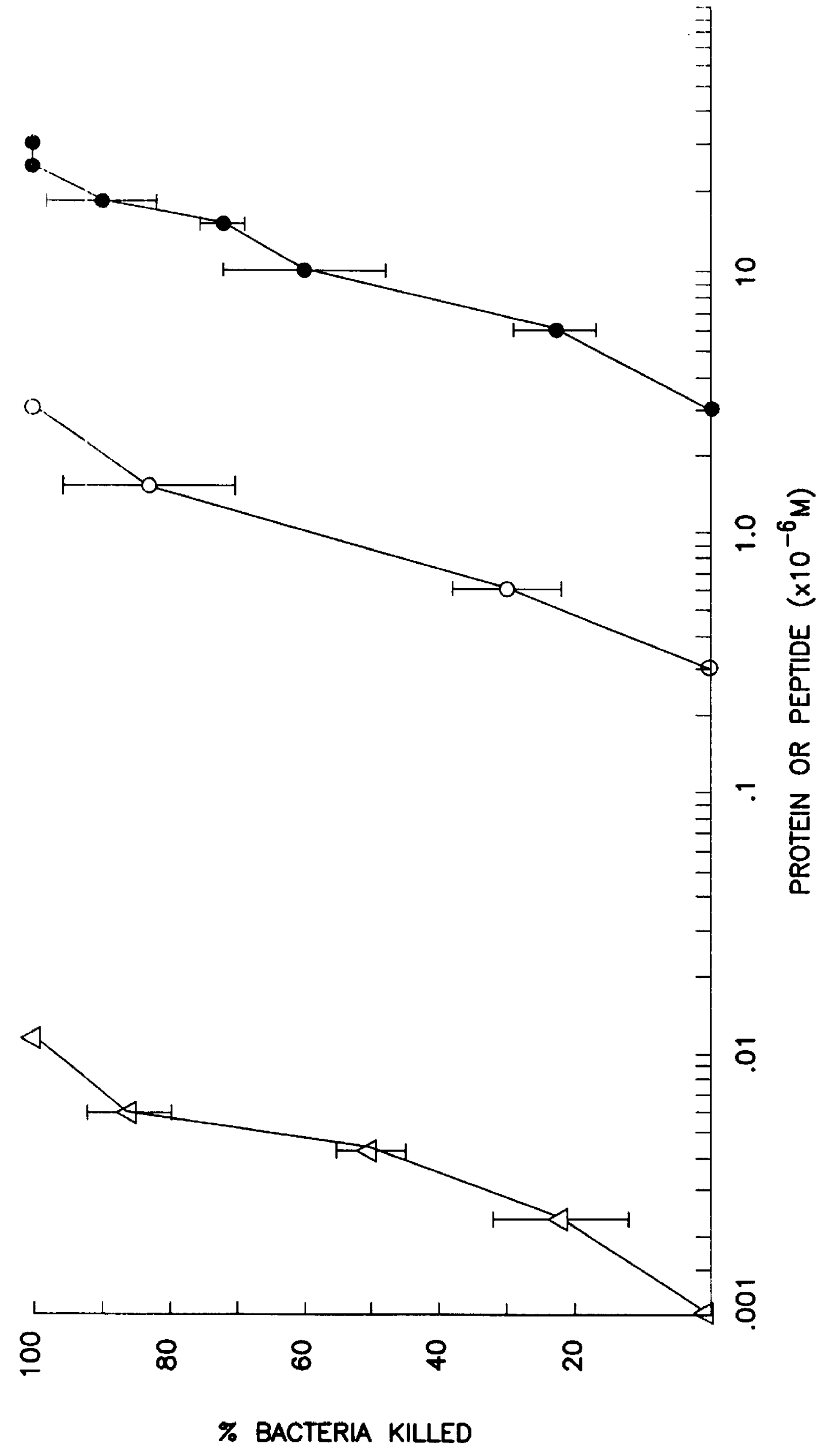
FIG. 1 shows the dose response for the bactericidal effects of peptides C#90-99 (○—○) and #90-99 (●—●) and B/PI (Δ—Δ) toward 5×10$^6$ CFU of *P. aeruginosa* type 1 incubated at pH 5.6. Values for C#90-99 are the mean of three experiments±one standard error of the mean.

The dose response of $5\times10^6$ CFU of *P. aeruginosa* to peptides C#90-99–#90-99, and B/PI was determined and the results are shown in FIG. 1. The bactericidal activity of the #90-99 peptide toward *P. aeruginosa* was linear with dose (FIG. 1) and is compared in the figure with the dose response of the most active of the bactericidal peptides, which was the #90-99 peptide with an added cysteine (C) at the amino terminus (C#90-99). The $LD_{50}$ of C#90-99 for *P. aeruginosa* was achieved at a 11.8 times lower peptide concentration than the $LD_{50}$ of peptide #90-99 ($8.2\times10^{-6}$M) and 37.7 times higher than the $LD_{50}$ for B/PI ($3.4\times10^{-9}$M). When compared to C#90-99, approximately 10 to 12-fold more of the peptide without the added cysteine (#90-99) was required for equal killing of *P. aeruginosa*. The #90-99 peptides were equally active towards two mucoid variants of *P. aeruginosa* and ATCC strain 27312 of *P. aeruginosa* (not shown).

Bactericidal activity of peptides was tested for killing of $5\times10^6$ bacteria at pH 5.6. Peptides containing the amino acid residues 90-99 of B/PI were tested as well as two hybrid peptides. The hybrid peptides have the sequence shown in Table 2 for peptide 18 (Hybrid) and peptide 17 (CHybrid). The Hybrid peptide (18) represents a combination of the amino acid sequence for peptide #90-99 and #227-236. The CHybrid (17) has the same sequence as the hybrid peptide except it has an N-terminal cysteine. The peptides were tested for bactericidal activity and the results are shown in Table 4. When rough strain *E. coli* were tested at pH 5.6 with $3\times10^{-5}$M of #90-99, 31% of $5\times10^6$ bacteria were killed (Table 4). The #90-99 peptide concentration required to kill *P. cepacia* at pH 5.6 and S. aureus at pH 7.0 was 5 times higher than the effective concentration of C#90-99 (not shown).

TABLE 4

| Bactericidal Activity of Synthetic Peptides at pH 5.6 | | |
|---|---|---|
| Synthetic | % Killing of 5 × $10^6$ Bacteria (Molar Concentration) | |
| Peptides | *P. aeruginosa* | *E. coli* B |
| C#90-99 | 83 ± 13 (1.5 × $10^{-6}$M) | 98 ± 3 (1.5 × $10^{-5}$M) |
| #90-99[a] | 75 ± 0 (1.5 × $10^{-5}$M) | 31 ± 3 (3.0 × $10^{-5}$M) |
| #86-99 | 79 ± 3 (6.0 × $10^{-6}$M) | 90 ± 1 (3.0 × $10^{-5}$M) |
| C#86-99 | 90 ± 5 (3.0 × $10^{-6}$M) | 91 (1.5 × $10^{-5}$M) |
| #90-102 | 67 ± 4 (6.0 × $10^{-6}$M) | 77 ± 6 (3.0 × $10^{-5}$M) |
| Hybrid | 79 ± 5 (3.0 × $10^{-5}$M) | 72 (6.0 × $10^{-5}$M) |
| CHybrid | 74 ± 3 (3.0 × $10^{-6}$M) | 71 (3.0 × $10^{-5}$M) |
| B/PI | 87 ± 8 (5.5 × $10^{-9}$M) | 71 (5.5 × $10^{-9}$M) |

[a]n = 6

The molar dose of peptides #86-99 and #90-102 required to kill *P. aeruginosa* was 2.5 times lower than the effective dose of the #90-99 peptide (Table 4, FIG. 1). At pH 5.6, neither the #90-102 nor the #86-99 peptide were substantially improved over the bactericidal activity of peptide #90-99 toward *E. coli* (Table 4).

At pH 5.6, the CHybrid molecule killed 74% of $5\times10^6$ *P. aeruginosa* cells at $3\times10^{-6}$M. This is a concentration of CHybrid 5-fold lower than the concentration of #90-99 required to kill 75% of the bacteria (Table 4, FIG. 1) and two times higher than the concentration of C#90-99 which killed 83% of the bacteria (Table 4, Table 3). The Hybrid molecule killed 79% of the *P. aeruginosa* cells at $3\times10^{-5}$M. At pH 5.6, 71% of *E. coli* were killed by Chybrid at $3\times10^{-5}$M. This is equal to the concentration of #90-99 required to kill *E. coli* and two times higher than the concentration of C#90-99 required to kill *E. coli* (Table 4).

These results show that peptides containing amino acids 90–99 of B/PI retain bactericidal activity for *P. aeruginosa* and *E. coli B*, but at a much higher concentration than the 55 kD B/PI. Addition of an N-terminal cysteine residue to #90-99 peptide increased its activity about 10-fold.

Although *P. cepacia* and *S. aureus* were resistant to killing by the parent B/PI protein, they were susceptible to the #90-99 and C#90-99 peptides in the same concentration range as *E. coli*. Two other hydrophilic peptides with an N-terminal cysteine were not bactericidal at 100 times the effective concentration of C#90-99.

Other peptides shown in Table 2 were tested for biological activity at pH 5.6 against *P. aeruginosa*. The results are shown in Table 5. The peptides with asterisks are #90-99 and C#90-99 which serve as reference peptides to compare the biological activity of the other peptides.

TABLE 5

| | | Effective Dose Bactericidal pH 5.6 *P. aeruginosa* | |
|---|---|---|---|
| Peptide Number | Code | Molar Concentration | Percent Killing |
| 1 | Signal | --- | |
| *2 | 1 C#90-99 | 1.5 × $10^{-6}$M | 83% |
| 3 | C#227-236 | --- | |
| 4 | C#418-427 | --- | |
| *5 | #90-99 | 1.5 × $10^{-5}$M | 75% |
| 6a | 4 #27-37 | --- | |
| 6b | C#27-37 | --- | |
| 7a | #160-170 | --- | |
| 7b | C#160-170 | --- | |
| 8a | #86-99 | 6.0 × $10^{-6}$M | 79% |
| *8b | C#86-99 | 1.5 × $10^{-6}$M | 88% |
| | dimer 8b | 1.5 × $10^{-6}$M | 52% |
| 9a | #90-102 | 6.0 × $10^{-6}$M | 67% |
| *9b | C#90-102 | 1.5 × $10^{-6}$M | 96% |
| 10a | 5 #118-127 | --- | |
| 10b | C#118-127 | --- | |
| 11 | F1 #1-26 | --- | |
| 12 | F2 #38-62 | 1.5 × $10^{-5}$M | 58% |
| 13 | F3 #63-99 | --- | |
| 14 | F4 | — | |
| 15 | F5 | — | |
| 16 | F6 | --- | |
| 17 | CHybrid | 3.0 × $10^{-6}$M | 74% |
| 18 | Hybrid | 3.0 × $10^{-5}$M | 79% |
| 19 | rand. 90-99 | 1.2 × $10^{-4}$M | 65% |
| 20a | C#90-99C | 3.0 × $10^{-6}$M | 76% |
| | cyclic 20a | 3.0 × $10^{-5}$M | 89% |
| 20b | #90-99C | 3.0 × $10^{-6}$M | 75% |
| 21 | rand. 90-99 | 1.5 × $10^{-5}$M | 71% |
| 22 | #82-#108 | 6.0 × $10^{-8}$M | 74% |
| 23 | C#82-#108C | 3 × $10^{-7}$M | 67% |
| 24 | Rustici#6 | 3.0 × $10^{-5}$M | 72% |
| 24 | pure | --- | |
| 25 | Rustici#2 | 6.0 × $10^{-6}$M | 56% |
| | cyclic | 1.5 × $10^{-5}$M | 73% |
| 26 | #91-92 wk→kw | 1.5 × $10^{-5}$M | 61% |
| 27 | #93 w→f | 3.0 × $10^{-5}$M | 49% |
| 28 | #93 w→a | 3.0 × $10^{-5}$M | 68% |
| 29 | #100-109 | --- | |
| 30 | #80-89 | --- | |
| 31 | #83-92 | 3.0 × $10^{-5}$M | 53% |
| 32 | #86-99 | 1.25 × $10^{-4}$M | 33% |
| 33 | #94-103 | --- | |
| 34 | #94-106 | --- | |
| 35 | #86-104 | 1.5 × $10^{-7}$M | 58% |
| 36 | C#86-104C | 1.2 × $10^{-4}$M | 39% |
| | cyclic | 1.5 × $10^{-7}$M | 76% |

--- = not active at concentrations of 1.2 × $10^{-4}$M or less

The results show that peptides containing the amino acid residues #90–99 and an N-terminal cysteine residues are the most active peptides for bactericidal activity against *P. aeruginosa*. The most active peptides are #82-108, C82-108C, 86-104 and C86-104C (cyclic). These peptides have activity close to that of native B/PI. A dimerized peptide of amino acid residues 86–99 has less biological activity (52% killing) as the undimerized peptide #C86-99 (88%) at the same concentration but it acquired endotoxin neutralizing activity. The cyclic peptide containing C#90-99C has about 10-fold less bactericidal activity as the linear peptide with N- and C-terminal cysteines but it acquired endotoxin neutralizing activity (20a).

As discussed previously, the hybrid peptides had an activity for killing of bacteria between that of the C#90-99 peptide and the 90-99 peptide.

Peptides were also formed by randomizing the amino acid sequence of the 90-99 peptide. The results show that the peptide kkkwfrlakq (SEQ ID NO:36) (21) retained biological activity, but the activity of the sequence wkkfkgralk (SEQ ID NO:35) (19) was reduced 8-fold. Replacement of the tryptophan (w) in peptide 21 with alanine (a) (27) or phenylalanine (f) (28) had little or no effect on bacterial killing activity indicating that the residue at position 93 can be substituted with another hydrophobic or aliphatic amino acid without dramatically affecting activity.

Bactericidal Activity of Peptide-Protein Conjugates

The bactericidal activity of C#90-99 coupled to KLH (KLH-C#90-99) was also tested with *P. aeruginosa*, as shown in Table 6 and compared there with KLH conjugates of the inactive peptides, C#227-236 and C#418-427.

TABLE 6

Bactericidal Activity of B/PI Peptides When Conjugated to a Protein Carrier

| Conjugate[a] | pH | % Killing of *Pseudomonas aeruginosa* | Peptide[b] Concentration |
|---|---|---|---|
| KLH-C#90-99 | 5.6 | 95 ± 3 | $1 \times 10^{-6}$M |
| $9 \times 10^{-8}$M | 7.0 | 90 ± 5 | 15:1[c] |
| KLH-C#227-236 | 5.6 | 0 | $5 \times 10^{-6}$M |
| $3 \times 10^{-7}$M | 7.0 | 0 | 16:1[c] |
| KLH-C#418-427 | 5.6 | 0 | $9 \times 10^{-6}$M |
| $5 \times 10^{-7}$M | 7.0 | 0 | 18:1[c] |

[a]$5 \times 10^6$ bacteria were incubated with a conjugate of peptide with Keyhole Limpet hemocyanin (KLH).
The final concentration of conjugate is shown and was based on quantitation by amino acid composition.
[b]The final concentration of peptide is calculated from the amino acid composition of each conjugate compared with unsubstituted KLH.
[c]The ratio of peptide to carrier is shown and was also derived from the amino acid composition.

From the results for the amino acid composition of each purified conjugate and unconjugated carrier protein, the ratio of peptide to carrier and the final concentration of peptide were calculated, as shown in the right hand column of Table 5. Approximately 90–95% of $5\times10^6$ *P. aeruginosa* cells were killed by the KLH-C#90-99 conjugate at a peptide concentration calculated at $1\times10^{-6}$M. The bactericidal molar concentration of conjugate was very close to the $1.5\times10^{-6}$M of free C#90-99 peptide which caused 83% killing of this microorganism (Table 3, FIG. 1). Neither KLH-C#227-236 nor KLH-C#418-427 were bactericidal for *P. aeruginosa* at 5 and 9 times higher concentrations of peptide, respectively (Table 6). Similar results were obtained with the ovalbumin (OVA) conjugates of these three peptides (not shown). For example, at pH 5.6, 70% of *P. aeruginosa* cells were killed by OVA-C#90-99 conjugate at $4.5\times10^{-8}$M. This represents a peptide concentration of approximately $6\times10^{-6}$M and a molar ratio of C#90-99 peptide to OVA carrier of 9:1, both determined by calculation from the amino acid composition of the conjugate compared with unconjugated carrier.

The cysteine of the unconjugated C#90-99 peptide was 100% reduced. The bactericidal activity was not diminished when the C#90-99 peptide was coupled to KLH or OVA protein carriers, thus eliminating the reactive reduced sulfhydryl group. The free sulfhydryl group is lost through bond formation with the N-maleimidomethyl group of the activated carrier and this suggests that retention of antibacterial activity is not dependent on a disulfide bond, as might be in the #20-44 peptide of CAP37 and as it is in the defensin molecules.

EXAMPLE 3

Assay of Peptides for Neutralization of Endotoxin

Synthetically produced peptides were assayed for the ability to neutralize endotoxin in the LAL.

Limulus Amoebocyte Lysate Assay

The ability of synthetic peptides to neutralize endotoxin was detected with the E-TOXATE kit manufactured by Sigma Chemicals, St. Louis, Mo. The concentration of peptide required to completely inhibit the coagulation of LAL driven by *E. coli* 055:B5 LPS was determined by dose response and as outlined in technical bulletin #210 of Sigma Chemicals. Peptide was incubated with LPS at room temperature for 10 minutes in 100 μl of a 1:2 dilution of pyrogen-free saline, pH 6.4. The reaction was started by addition of 100 μl of amoebocyte lysate and the final volume was 200 μl. The results for some of the peptides are shown in Table 7.

TABLE 7

Synthetic Peptides With Endotoxin-Neutralizing Capacity

| Peptide Number | | Synthetic Peptide | Effective Dose M ($\times 10^{-4}$) | Effective Dose (μg/0.2 ml)[a] |
|---|---|---|---|---|
| 7a | #160–170 | kkiesalrnkm (SEQ ID NO: 16) | 4.5 | 119 |
| 3 | C#227–236 | cefysenhhnp(g) (SEQ ID NO: 17) | 1.2 | 34 |
| 4 | C#418–427 | cneklqkgfpl (SEQ ID NO: 18) | 1.5 | 38 |
| 18 | Hybrid | efysenhhnpkwkaqkrflk (SEQ ID NO: 11) | 3.0 | 155 |
| 17 | CHybrid | cefysenhhnpkwkaqkrflk (SEQ ID NO: 12) | 1.2 | 81 |
| B/PI | | | 0.00015 | 0.165 |

[a]The dose of peptide required to inhibit clotting of LAL by 100%.
Each tube contained 0.04 endotoxin units of *E. coli* LPS.

Figure 2:
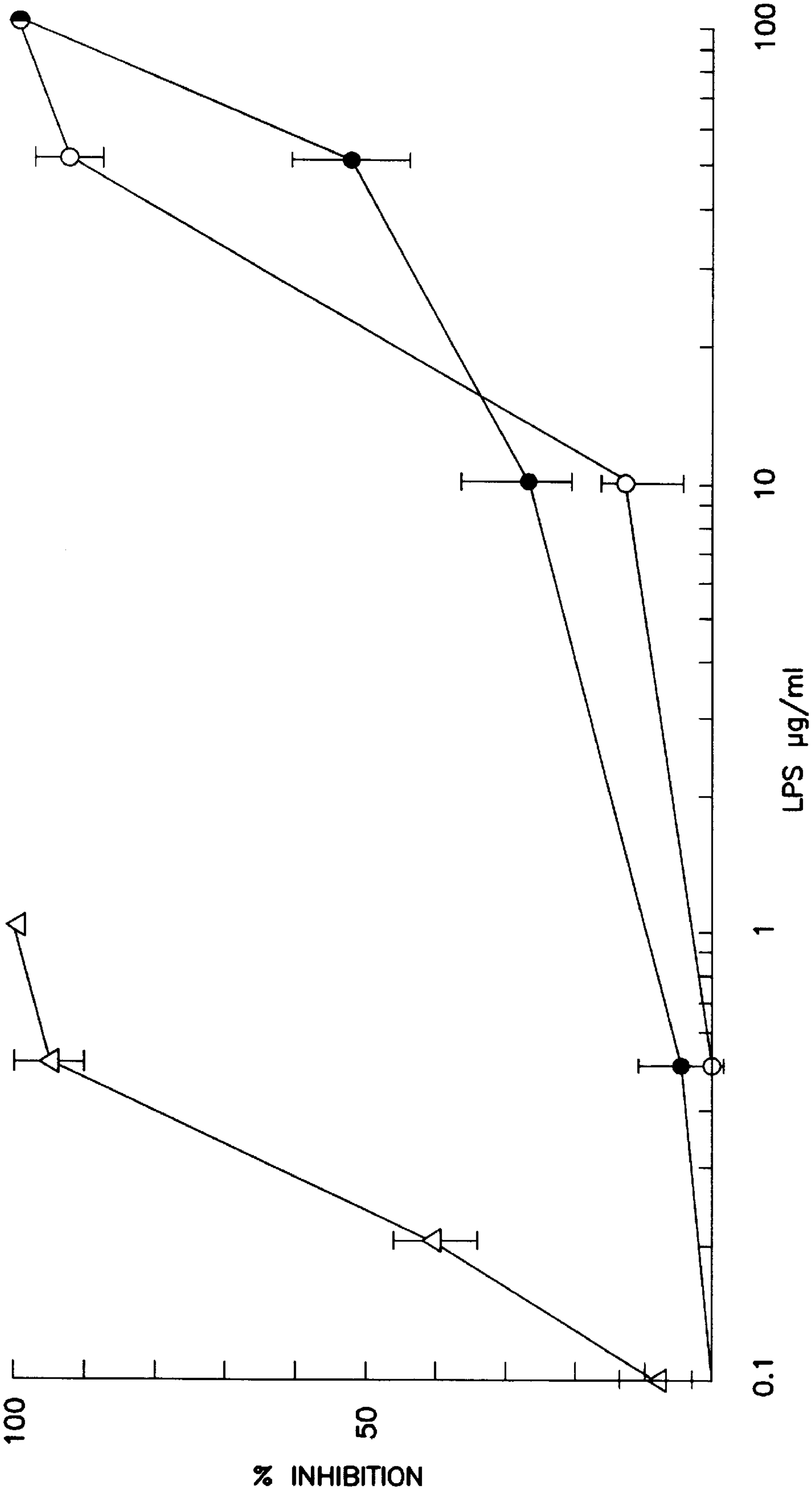
FIG. 2 shows the percent inhibition by purified LPS from *P. aeruginosa* 27312 (List Biological Laboratories, Campbell, Calif.) of the bactericidal activity of 2.3 μg/ml of C#90-99 (○—○;n=3) peptide or 23 μg/ml #90-99 (●—●) peptide or B/PI (Δ—Δ). Peptide was incubated at pH 5.6 with LPS for 15 minutes before the addition of 5×10$^6$ CFU of *P. aeruginosa* cells.

Although they were bactericidal for *E. coli*, linear peptides including amino acid sequence of #90-99 did not neutralize the procoagulant effects of *E. coli* endotoxin on LAL. The highest concentration of each peptide tested was $4.5\times10^{-4}$M. Linear peptides C#90-99, #90-99, C#89,90, #86-99, #86-104, and #90-102 did not neutralize endotoxin in the LAL. However as shown in FIG. 2, the C#90-99 and #90-99 peptides will bind to purified LPS from *P. aeruginosa* and that binding inhibits the bactericidal activity of the peptides. The $ID_{50}$ for C#90-99 was approximately 21 ug/ml and for #90-99 was approximately 42 ug/ml.

Three peptides with 11 amino acid residues were capable of neutralizing endotoxin in the Limulus assay. The concentration of peptide required for 100% inhibition of LPS-induced gelation of the amoebocyte lysate was determined by dose response. The endotoxin-neutralizing activity of the peptides was comparatively weak and is shown in Table 7. The most active endotoxin neutralizing peptide was C#227-236, which neutralized 0.04 endotoxin units of *E. coli* 055:B5 LPS when at a peptide concentration of $1.2\times10^{-4}$M. The C#418-427 peptide was closely similar and neutralized endotoxin at $1.5\times10^{-4}$M. The third peptide with neutralizing capacity (#160-170) was considerably less active than the aforementioned peptides and neutralized endotoxin at $4.5\times10^{-4}$M.

A hybrid peptide of the C#227-236 and #90-99 peptides (CHybrid, Table 2) was synthesized and tested for endotoxin neutralization (Table 7) and killing of *P. aeruginosa* and *E. coli* (Table 4). The CHybrid molecule completely neutralized endotoxin at the same concentration ($1.2\times10^{-4}$M) as did the original C#227-236 peptide. The Hybrid molecule without the N-terminal cysteine (Hybrid, Table 7) required two times more peptide for endotoxin neutralization than was required in the case of CHybrid. All results in Table 7 were reproduced without variation in at least two different experiments.

Other peptides were tested for endotoxin neutralizing activity as shown in Table 8. The asterisks identify reference peptides that have endotoxin neutralizing activity.

TABLE 8

| Peptide Number | Code | Effective Dose Endotoxin Neutralization (Molar Concentration) |
|---|---|---|
| 1 | Signal | — |
| 2 | 1 C#90–99 | — |
| *3 | C#227–236 | $1.2 \times 10^{-4}$ M |
| *4 | C#418–427 | $1.5 \times 10^{-4}$ M |
| 5 | #90–99 | — |
| 6a | 4 #27–37 | — |
| 6b | C#27–37 | — |
| *7a | #160–170 | $4.5 \times 10^{-4}$ M |
| 7b | C#160–170 | $4.5 \times 10^{-4}$ M |
| 8a | #86–99 | — |
| 8b | C#86–99 | — |
| | dimer 8b | $3.0 \times 10^{-4}$ M |
| 9a | #90–102 | — |
| 9b | C#90–102 | — |
| 10a | 5 #118–127 | — |
| 10b | C#118–127 | — |
| 11 | F1 #1–26 | $7.5 \times 10^{-5}$ M |
| 12 | F2 #38–62 | $7.5 \times 10^{-5}$ M |
| 16 | F6 | $1.5 \times 10^{-4}$ M |
| 17 | CHybrid | $1.2 \times 10^{-4}$ M |
| 18 | Hybrid | $3.0 \times 10^{-4}$ M |
| 19 | rand.90–99 | — |
| 20a | #C90–99C | — |
| | cyclic 20a | $4.5 \times 10^{-4}$ M |
| 20b | #90–99C | — |
| 21 | rand.90–99 | — |
| 22 | #82–108 | $3.0 \times 10^{-5}$ M |
| 23 | #C#82–108C | $3.0 \times 10^{-5}$ M |
| 24 | Rustici #6 | — |
| 24 | pure | $3.0 \times 10^{-4}$ M |
| 25 | Rustici #2 | — |
| | cyclic 25 | $4.5 \times 10^{-4}$ M |
| 26 | rand #90–99 | $3.0 \times 10^{-4}$ M |
| 27 | #93W→f | — |
| 28 | #93W→a | — |
| 29 | #100–109 | $2.2 \times 10^{-4}$ M |
| 30 | #80–89 | $4.5 \times 10^{-4}$ M |
| 31 | #83–92 | $2.2 \times 10^{-4}$ M |
| 32 | #86–95 | $4.5 \times 10^{-4}$ M |
| 33 | #95–104 | $4.5 \times 10^{-4}$ M |
| 34 | #97–106 | $7.5 \times 10^{-5}$ M |
| 35 | #86–104 | $4.5 \times 10^{-4}$ M |
| 36 | C#86–104C | $7.5 \times 10^{-5}$ M |
| | cyclic 36 | $2.25 \times 10^{-4}$ M |

— = not active at concentrations of $4.5 \times 10^{-4}$ M or less.

The results show that the reference peptides #160-170 (7a), C#227-236 (3), C#418-427 (4) demonstrated endotoxin neutralizing activity. Other active peptides include a peptide containing amino acids 1–26, the F6 peptide (16) and the pure Rustici peptide, peptide with amino acids 82–108 and a peptide with amino acids 86–104.

Linear peptides containing amino acids #90–99 did not have endotoxin neutralizing activity but a dimer of C#86-99 and cyclic compound of C#90-99C did acquire endotoxin neutralizing capability.

Several of the synthetic peptides have both bactericidal activity and endotoxin neutralizing activity. some of those peptides are as shown in Table 9.

TABLE 9

| | | Effective Dose (molar concentration) | |
|---|---|---|---|
| Peptide Number | Code | Bactericidal Activity for pH 5.6 *P. aeruginosa* | Endotoxin Neutralization |
| 8b dimer | (C#86–99) | $1.5 \times 10^{-6}$ M | $3.0 \times 10^{-4}$ M |
| 12 | f2 #38–62 | $1.5 \times 10^{-5}$ M | $7.5 \times 10^{-5}$ M |
| 17 | CHybrid | $3.0 \times 10^{-6}$ M | $1.2 \times 10^{-4}$ M |
| 18 | Hybrid | $3.0 \times 10^{-5}$ M | $3.0 \times 10^{-4}$ M |
| 20a Cyclic | (C#90–99) | $1.5 \times 10^{-6}$ M | $4.5 \times 10^{-4}$ M |
| 22 | #82–108 | $6.0 \times 10^{-8}$ M | $2.0 \times 10^{-5}$ M |
| 23 | C#82–108C | $3.0 \times 10^{-7}$ M | $3.0 \times 10^{-5}$ M |
| 25 | cyclic 25 | $1.5 \times 10^{-5}$ M | $4.5 \times 10^{-4}$ M |
| 26 | kwkfkqralk | $1.0 \times 10^{-5}$ M | $3.0 \times 10^{-4}$ M |
| 35 | #86–104 | $1.5 \times 10^{-7}$ M | $4.5 \times 10^{-4}$ M |
| 36 | C#86–104C | $1.2 \times 10^{-4}$ M | $7.5 \times 10^{-5}$ M |
| | cyclic 36 | $1.5 \times 10^{-7}$ M | $2.25 \times 10^{-4}$ M |

The hybrid molecules are synthetic peptides including the amino acid sequences for #90-99 and C#227-236. The hybrid peptides retained both bactericidal activity and endotoxin neutralizing activity comparable to either of those peptides alone. A dimer of C#86-99 and a cyclic peptide of C#90-99C retained bactericidal activity and acquired endotoxin neutralizing activity not present in the linear peptides (C#90-99C and C#86-99). A peptide including amino acids 90–99 can have both bactericidal and endotoxin neutralizing activity whether in linear or cyclic form such as peptides including amino acid sequences 82-108 and 86-104. Thus, bactericidal activity is associated with the peptides having amino acids 90–99 and endotoxin neutralizing activity can also be associated with a peptide having this sequence depending on its conformation.

EXAMPLE 4

Inhibition of Bactericidal Activity by Incubation with Endotoxin

Inhibition of bactericidal killing by LPS from *P. aeruginosa* ATCC 27312 (List Biological laboratories, Campbell, Calif.) was determined with LPS suspended in 0.1% triethylamine. LPS and peptide were incubated at pH 5.6 in 0.85 ml of buffer for 15 minutes at which time 0.15 ml of bacteria were added. Bactericidal effects were determined as described previously. Where an inhibitory dose $ID_{50}$ is indicated, it was determined by linear regression analysis after dose response experiments.

The results shown in FIG. 2 indicate that the #90–99 peptides will bind to purified LPS from *P. aeruginosa* and inhibit killing of *P. aeruginosa* by either of these peptides. The 50% inhibitory dose ($ID_{50}$) of LPS with C#90-99 was approximately 21 μg/ml, while the $ID_{50}$ of LPS with peptide #90-99 was approximately 45 μg/ml of LPS. Killing of *P. aeruginosa* was also inhibited by LPS from *E. coli* 0111:B4 (not shown), but inhibition of bacterial killing by both C#90-99 and #90-99 peptides required 40% more *E. coli* LPS (not shown) than was required with LPS from *P. aeruginosa* (FIG. 2).

These results indicate that the bactericidal function of B/PI can be located to a linear amino acid sequence including amino acid residues #90–99. An endotoxin neutralizing function can be assigned to the same location but appears conformation dependent.

EXAMPLE 5

Toxicity of Synthetic Peptides for Eukaryotic Cells

The synthetic peptides were assayed for toxicity to cultured eukaryotic cells. Human lung fibroblasts were grown in monolayers in Dulbecco's Modified Eagles' Medium (DMEM) with 10% fetal calf serum (FCS) and originated as primary cultures of lung mesenchymal cells. The cells were trypsinized, washed with either DMEM plus FCS or phosphate-buffered saline (PBS), pH 7.4, and incubated with peptide at a final cell concentration of $1\times10^7$/ml. Nine volumes of cell suspension were diluted with one volume of 0.4% trypan blue and the cells were counted with a hemocytometer, while also determining the fraction of cells which were increased in permeability to dye. There was no significant loss of cell number due to exposure of the fibroblasts to peptide.

The results are shown in Table 10.

TABLE 10

Effects of Synthetic Peptides on Viability of Human Lung Fibroblasts

| Peptide Number | Synthetic Peptide | Percent Viability[a] | |
|---|---|---|---|
| | | DMEM | PBS |
| Control | | 98.5 | 93.1 |
| #90–99 | kwkaqkrflk[b] (SEQ ID NO: 6) | 98.0 | 89.4 |
| C#90–99 | ckwkaqkrflk[c] (SEQ ID NO: 7) | 98.4 | 94.7 |
| Hybrid | efysenhhnpkwkaqkrflk[b] (SEQ ID NO: 11) | 98.8 | 95.6 |
| CHybrid | cefysenhhnpkwkaqkrflk[c] (SEQ ID NO: 12) | 99.2 | 92.3 |

[a]Viability was determined by trypan blue exclusion following incubation of cells with peptide for 30 minutes in DMEM plus 10% FCS or in PBS, pH 7.4.
[b]Final concentration of $1.5 \times 10^{-4}$ M.
[c]Final concentration of $1.5 \times 10^{-5}$ M.

The toxicity of four of the bactericidal peptides for mammalian cells was tested by incubation of human lung fibroblasts with 10 times the bactericidal peptide concentration effective with *P. aeruginosa*. There was no significant increase in permeability to trypan blue (Table 10) as a result of exposure to any of the peptides tested.

EXAMPLE 6

Formation of Monoclonal and Polyclonal Antibodies to Peptides

Peptides were conjugated to KLH or ovalbumin carrier proteins as described in Example 1. The following peptide-carrier conjugates were made:

#90-99
#227-236
#418-427
#27-37
#118-127
#160-169

These peptide carrier molecules were injected into rabbits using standard methods. Antibodies to B/PI were obtained in a similar manner or can be obtained from Chemicon Int'l, Inc. (Femecula, Calif.). Both monoclonal and polyclonal antibodies were obtained using standard methods as described in *Antibodies: A Laboratory Manual*, Harlow and Lane, Cold Spring Harbor Laboratory (1988).

Polyclonal antisera and monoclonal antibodies specific for peptides were analyzed by Western blot. The results are shown in FIG. 3.

Figure 3:
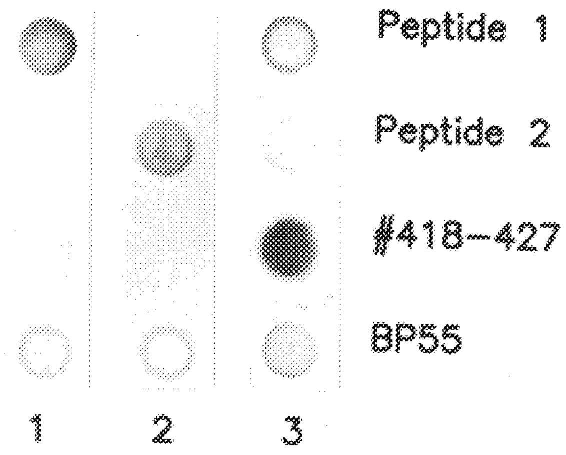
FIG. 3 shows Western dot blot of peptides derived from BP55 using rabbit polyclonal sera. Lane 1 peptide #90-99, Line 2 peptide #227-236, Lane 3 peptide #418-427. Each lane also contained BP55. The lanes were probed with antisera from rabbits immunized with #90-99, #227-236, #418-427, respectively.

Dot blots of peptide-OVA conjugates on nitrocellulose strips are shown in FIG. 3 and were stained by Western blot method. Strips were blocked with 1.5% gelatin and incubated at room temperature with a 1:2000 dilution of rabbit anti-peptide antibody followed by a 1:1000 dilution of goat anti-rabbit IgG coupled to alkaline phosphatase. Color was developed by incubation with substrate for the enzyme as described by the manufacturer. Rabbit antibody to peptide 1 (#90-99; lane 1), reacted only with peptide 1 and weakly with B/PI. Antibody to peptide 2 (#227-236, lane 2) reacted strongly with peptide 2 and B/PI and cross-reacted weakly with other peptides. Antibody to peptide #418-427 (lane 3) reacted strongly with the homologous peptide but weakly with B/PI. Monoclonal antibody designated ANH13 specific for B/PI (Wasiluk et al., cited supra.) also reacted strongly with peptide 2 (not shown). The antibody to peptides #227-236 and #418-427 will be cross-absorbed with heterologous peptide-OVA conjugates to improve specificity.

EXAMPLE 7

Preparation of cDNA clone encoding B/PI (1-496)

A cDNA encoding a portion of B/PI has been isolated. The cDNA clone has been subcloned into a baculovirus vector for expression in insect cell culture. The cDNA clone was obtained by standard methods as described by Maniatis et al., *A Guide to Molecular Cloning* (1989). A full length cDNA library coding for B/PI was obtained from a cDNA library obtained from ClonTech Laboratories, Inc., Palo Alto, Calif. The cDNA library was screened using monoclonal antibodies for B/PI and positive plaques were amplified and sequenced using standard methods. The sequence of the full length cDNA is shown in FIG. 8.

The cDNA for B/PI was subcloned in the transfer vector pVC1393 or the Bluebac His III vector (Invitrogen Corp., San Diego, Calif.) using restriction enzymes. The cDNA was inserted into the correct orientation at EcoRI site for pV139 or a BamHI site for Bluebac His III vector. Co-infection of insect cells with the recombinant transfer vector and the wild type baculovirus led to the isolation of a recombinant B/PI as detected by Western blot using monoclonal antibodies to B/PI.

Primers were selected to amplify portions of the cDNA sequence for B/PI and are shown in FIG. 4 in the boxed regions and with letter designations. Primers were selected to amplify fragments encoding amino acids 1–110. Primer pairs shown in FIG. 4 that can be utilized to amplify cDNA coding for amino acids 1–110 include primer GI and C. The primers are designed to be complementary to the coding sequence at these regions of the cDNA sequence and preferably are about 1–30 nucleotides long. Primer sequences can be selected based on well established principles known to those of skill in the art and can include noncomplementary sequences such as restriction enzyme recognition sequences and sequences coding for amino acids such as cysteine or methionine. For example the 5' to 3' primers have a BamHI restriction site and the 3' to 5' primers have a BglII restriction site and a stop codon.

Figure 5:
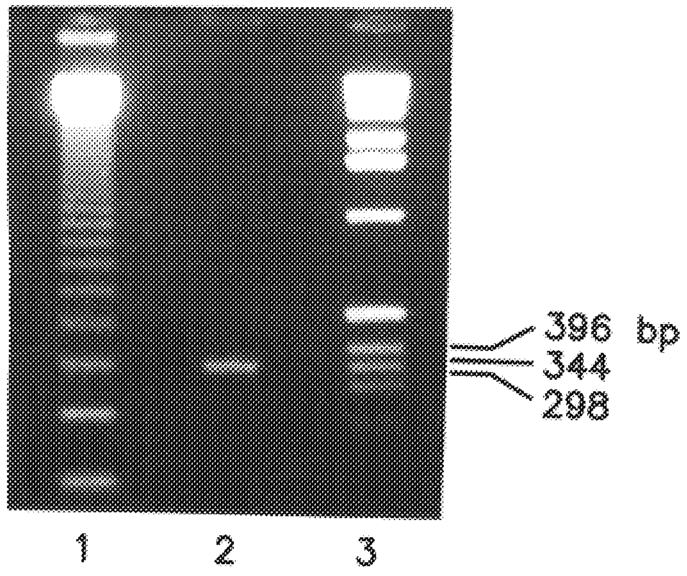
FIG. 5 represents agarose gel electrophoresis of a PCR product generated with primers GI and C as shown in FIG. 4. Lane 1 is a 0.1 Kb standard ladder; Lane 2 is the PCR product; and Lane 3 is a standard 1 Kb ladder. Bands were visualized with ethidium bromide.

A fragment of the cDNA sequence encoding amino acids 1–110 was amplified using primers GI and C. The reverse primer C is the inverse complement of the sequence shown under primer C followed by a stop codon and an extended BgIII restriction site. The PCR product of this primer was estimated to be 353 base pairs and was isolated by agarose gel electrophoresis. See FIG. 5 (Lane 2). This fragment codes for amino acids 1–110 of the mature B/PI protein.

The PCR reaction was carried out by incubation of primers (as shown in FIG. 4) and the cDNA insert for B/PI with PCR buffer, dNTPs and Taq polymerase as described in Larrick et al., *Bio/Tech*, 7:934 (1989). Each PCR contains 100pg-10ng of template oligonucleotide, 10–40 nmole each of appropriate combination of primers, 20 mM Tris-HCl, pH 8.3 at 20° C., 1.5 nM $MgCl_2$, 25 mM KCl, 50 $\mu$M of each dNTP and 2.5 units of Taq polymerase. The PCRs were carried out for 25–40 cycles on thermal cycler using the following conditions: 94° C., 1 minute; 42°–55° C., 2 minutes; 72° C., 3 minutes. PCR fragments were purified by agarose gel electrophoresis, digested with restriction enzymes and ligated into the baculovirus transfer vector. Sequencing of the PCR product insert in the transfer vector was by the dideoxynucleotide chain termination method with Sequenase (U.S. Biochemicals) and by direct sequencing of the double-stranded DNA of baculovirus. Wang et al., *J. Virol Meth*., 31:113 (1991).

Plasmid pVL1393 is a vector that contains the polyhedron gene and all known translational regulatory sequences upstream and downstream of the ATG start site of the polyhedron gene. The natural ATG has been removed through site directed mutagenesis so that translation begins with the ATG of the foreign cDNA inserted at any of a number of cloning sites within the polyhedron gene of the transfer vector. The Bluebac His III vector is a vector that contains a B-galactosidase gene under control of the polyhedron gene promoter. When a recombinant fragment is inserted into a BamHI site it forms a DNA sequence coding for a B-gal fusion protein. A restriction map is shown in FIG. 7. The transfer vector wild type baculovirus, AcMNPv and *Spodoptera frugiperda* Sf9 host cells have been purchased from Invitrogen Corp., San Diego, Calif. A full-length cDNA for B/PI has been subcloned by ligation into the EcoRI site of the pVL1393 baculovirus transfer vector. A subclone of the correct orientation was established by restriction mapping.

Expression of B/PI in insect cells infected with a recombinant baculovirus. Baculoviruses have been developed for high-level expression of foreign genes in insect cells. Luckow et al, *Biotech*, 6:47 (1988). Glycosylations are more fully accomplished in this system than in other expression systems and the abundant expression of many mammalian proteins which are appropriately folded, processed and functionally active has been achieved. In this system, the cDNA of the foreign gene is ligated into a plasmid transfer vector such as pVL1393 containing a strong promoter of the baculovirus polyhedron gene. Under the control of this promoter, the inserted cDNA should be overexpressed after recombination of the polyhedron gene (with its insert) and the infectious wild-type baculovirus (AcMNPV). This occurs during coinfection of permissive *Spodoptera frugiperda* (Sf9) cells with AcMNPV and the transfer vector.

Recombinant virus form a visibly different plaque morphology which provides a convenient means of selecting for recombinant virus. In addition, inserts in the Bluebac His III vector can be detected by expression of B-gal fusion proteins. Insect cell culture plaques expressing the fusion protein turn blue when supplied with a labelled substrate. Alternatively, plaques can be detected by an antibody method. Plaques with highest level expression of the foreign gene can be identified immunologically and the purified recombinant virus used for large scale production of foreign protein after infection of Sf9 insect cells.

Cells and transfections. Recombination of transfer vector with wild-type baculovirus AcMNPV can be performed by cotransfection of Sf9 cells. The Sf9 cells are maintained as ‘monolayer’ cultures at 28° C. in Grace’s medium (Invitrogen) supplemented with 10% heat-inactivated fetal calf serum and 50 $\mu$g/ml gentamicin. For large scale virus preparations and production of recombinant protein, cells can be grown in suspension in the same medium. Transfections and plaque assays can be performed essentially as described by Summers et al., *A Manual for Baculovirus Express System, Tex. Agric. Exp. Stn:Bull*, 1555 (1987), but with some modification. Viral plaques with an altered plaque morphology can not only be picked, but infected cells can also be assayed for the presence of B/PI and with rabbit antibodies to synthetic peptides based on the structure of B/PI.

Screening for expression by recombinants can be as described by Capone, *J. Gen. Anal Techn*., 6:62 (1989). The agar overlay can be carefully removed from plates containing plaques and placed plaque side up in a sterile culture dish. A disk of nitro-cellulose filter can be placed on the agar for 5 minutes, peeled off and placed in blocking solution (10% calf serum in TBST). A 30-minute blocking step can be followed by incubation with antibody to B/PI, then with a second antibody to mouse immunoglobulin which is coupled with alkaline phosphatase. Finally, the disk can be stained with substrate for the enzyme, and plaques with strong expression are identified. Selected recombinant virus can be plaque-purified four times and the purified virus can be expanded and used in large scale infections of Sf9 cells.

Sf9 cells have been maintained and transferred in culture without difficulty for the past two years. Wild-type and recombinant plaques have been recognized using a Bluebac His III transfer vector with cDNA insert and gene for beta-galactosidase. About 200 plaques/plates were detected that expressed the full length B/PI (data not shown).

Preparation of cell extracts. Foreign proteins are rarely secreted by Sf9 cells infected with recombinant baculovirus and recombinant proteins are usually isolated from lysates of infected cells. Culture supernatants are checked for secretion of truncated B/PI, but in the event it is not there B/PI fragments are isolated from cell lysates. Infected cells are harvested and washed twice in ice-cold PBS, pH 6.2. Subsequent manipulations are carried out at 4° C. Cells are collected by centrifugation at 500×g for 10 minutes, then resuspended in lysis buffer (20mM HEPES, pH 7.5, 5 mM KCl, 0.5 mM DTT, 1 mM PMSF) and maintained on ice for 10 minutes. Cells are then disrupted by homogenization. Nuclei are removed by sedimentation and the supernatant clarified by centrifugation at 26,000×g for 20 minutes. Samples of culture supernatant and cell lysate supernatant are subjected to SDS PAGE, electrotransfer of proteins and Western blot analysis.

Purification of truncated recombinant fragments of B/PI. Recombinant products can be purified from infected cells by immunoaffinity chromatography with the appropriate immobilized rabbit anti-peptide antibody or a mouse monoclonal antibody to B/PI. B/PI was reproducibly purified by application of partially purified samples of 2 mg protein to a 1.5×180 cm Toyopearl HW55S (Toso Haas) column or 200 mg protein to a TSX2000 HPLC (Beckman) column. The elution buffer for both columns is 0.05M glycine buffer, pH 2.5, with 0.5M NaCl. Recovery of B/PI protein was excellent and 100% of bactericidal activity is retained. The bactericidal activity of B/PI in this buffer was stable at 40°C. and at −700C for prolonged periods. The columns resolve protein standards over the range of 2–70 kD and can be used for all steps separation of fragments of B/PI by molecular weight. Reverse phase HPLC can be used if necessary.

EXAMPLE 8

B/PI peptides with bactericidal and endotoxin neutralizing peptides

This work identified a preferred peptide having an amino acid sequence from B/PI from amino acids 82–108. In this peptide isoleucine 85 and leucine 106 were replaced with cysteines, as described above. This region is believed to fold into an amphipathic B-sheet with a hydrophilic surface that presents a potential bioactive domain. A series of decapeptides were synthesized that "walk-through" the B/PI sequence 80-109, shifting by three or four residues each. Quantitative bactericidal and endotoxin activities for these peptides were measured by bactericidal assay and by Limulus amoebocyte lysate assay for endotoxin neutralizing activity.

Bacteria: *P. aeruginosa* type 1 is a clinical isolate maintained in the laboratory. The isolate remains a smooth strain and was serotyped by the scheme of Homma. The Pseudomonas strain was maintained by monthly transfer on blood agar plates.

Bactericidal assay: Pyrogen-free solutions were used throughout this assay and all methods which follow. Log phase bacteria were prepared from a culture in brain heart infusion broth as described (Hovde, et al. (1986) *Infect. Immun.* 54:142–148) except that bacteria were washed and resuspended in saline with adjustment to an optical absorbance at 650 nm which would yield $3\times10^8$ CFU/ml. Bacteria were then diluted 1:10 in 0.08M citrate phosphate buffer, pH 5.6 or pH 7.0 (prepared by mixing 0.08M citric acid with 0.08M dibasic sodium phosphate). Bactericidal activity was determined by dose response where an LD50 was indicated it was determine by linear regression. Bacteria (0.15 ml) were incubated with peptide or B/PI protein in a final volume of 1.0 ml of buffer for 30 min in optically matched tubes in a reciprocal water-bath shaker at 37° C. Nutrient broth medium was then added and growth was followed by optical absorbance at 650 nm. Data were collected when bacterial cultures were at mid-log phase.

Purification of B/PI: B/PI was purified in three column-chromatography steps. In the final step, the sample was applied to a 1×180 cm molecular sieving column of Toyopearl HW55S (TosoHaas, Philadelphia Pa.) which had been equilibrated with 0.05M glycine buffer (pH 2.5) containing 0.5M NaCl. Protein concentration was determined according to Hartree (Hartree (1976) *Jpn. J. Exp. Med* 46:329–336). Purity was confirmed by visualization of a SDS polyacrylamide gel following electrophoresis of 1 μg of purified BP55 protein and silver staining of the gel using techniques well known in the art.

Peptide Preparation: Peptides were synthesized at the University of Minnesota Microchemical Facility using a Milligen/Biosearch 9600 peptide synthesizer. All peptides were solid-phase synthesized by use of fluorenylmethoxycarbonyl chemistry. The profile of cleaved peptide was obtained by analytical high performance liquid chromatography (HPLC). Lyophilized crude peptides were purified by preparative reversed-phase HPLC on a C18 column with an elution gradient of 0–60% acetonitrile with 0.1% trifluoroacetic acid in water. Pure peptides were subjected to gel filtration using a 1×9 cm Sephadex G25 column and pyrogen-free saline buffered with 0.008M citrate phosphate buffer (pH 7.0), as elution buffer and used to confirm results obtained at every step of the study. The purity and composition of the peptides were verified by HPLC analysis of amino acid composition of hydrolysates prepared by treating the peptides under argon in 6M HCl for 24 H at 110° C. The amino acid sequence of peptide 90-99 was confirmed by gas-phase Edman degradation, using an Applied Biosystems 470A gas-phase sequenator with a reverse phase C18 column (2.1×250 mm). The thio groups of all peptides containing a cysteine residue were fully reduced. This was ascertained with Ellman's reagent using reduced glutathione as a standard. Peptide 82-108 with cysteine replacing isoleucine at residue 85 and leucine at residue 106, was cyclized by air oxidation in sterile pyrogen-free 0.1M citrate phosphate buffer (pH 7.0) as described by Rustici, et al. (*Science* 259: 361–365, 1993). Following lyophilization, the cyclic peptide was purified by preparative HPLC as described above. The purified cyclic peptide was reduced with a 50-fold molar excess of dithiothreitol and was shown to return to the elution time for the linear cysteine modified 82-108 peptide. The cyclic peptide was shown to be monomeric by mass spectrometry.

Limulus amoebocyte lysate assay: The ability of synthetic peptides to neutralize endotoxin was detected with the E-TOXATE kit manufactured by Sigma Chemicals (St. Louis, Mo.). The concentration of peptide required to completely inhibit the coagulation of Limulus amoebocyte lysate driven by 0.04 unit (or 0.01 ng) of *E. coli* 055:B5 LPS was determined by dose response and as outlined in technical bulletin No. 210 of Sigma Chemicals. Peptide or B/PI was incubated with LPS at room temperature for 5 min in 100 ul of a 1:2 dilution of pyrogen-free saline (pH 6.4). The reaction was started by addition of 100 ul of amoebocyte lysate and the final volume was 200 ul. Assuming a 10,000 molecular weight for LPS, the approximate molar ration of B/PI:LPS at neutralization was 3000 to 1.

The peptides tested and bactericidal and endotoxin neutralizing data is provided in Table 11 and 11a. Data are shown for bactericidal activity assayed at pH 5.6 (Table 11), the pH optimum for B/PI and at a more physiologic pH of 7.0 (Table 11a). Trends at either pH are similar and their is no apparent effect of pH on peptide activity. Peptide 90-99 was seen as the most effective bactericidal agent. In terms of percent bacteria killed, the activity first appeared within peptide 83-92. Greatest activity resided within a ten residue sequence 90-99 and the tripeptide KWK was important for maximal activity. Peptide 90-99 had no endotoxin neutralizing activity (Table 11) at a concentration of 4.5 $10(^{-4})$ M. This was the only peptide in the region without endotoxin neutralizing activity. When the sequence was extended to include residues 86–104, endotoxin neutralizing activity was acquired and bactericidal activity was increased 16-fold over peptide 90-99. When the LD50 of peptides and native B/PI are compared at pH 7.0 (Table 12) peptide 90-99 is about 833-fold less potent than native B/PI. Peptides 80-89, 83-92. 94-103 and 97-106 neutralized endotoxin but were not bactericidal. Peptide 97-106 was most effective at endotoxin neutralization and some activity resided within 83-92 over that of the N-terminal and C-terminal peptides. The B/PI sequence 86-104 had a high probability for sequence alignment and therefore for structural conservation with the LALF-like beta sheet (Hoess, et al. (1993) EMBO J. 12:3351–3356). The 86-104 sequence was 16-times more active in bactericidal reactions with *P. aeruginosa* than was the 90-99 sequence.

TABLE 11

| Bactericidal and endotoxin neutralization activities in B/PI-derived synthetic peptides | | | | | |
|---|---|---|---|---|---|
| | Bactericidal Activity Towards 5 $-10^6$ Bacteria[a] pH 5.6 | | | Endotoxin | |
| | Concn. | | | neutralization | |
| Peptide | n | effective dose (M) | % bacteria killed[b] | n | Concn.[c] (M) |
| 80–89 | 5 | $1.2 \cdot 10^{-4}$ | 0 | 3 | $4.5 \cdot 10^{-4}$ |
| 83–92 | 6 | $3.0 \cdot 10^{-5}$ | 61 ± 7 | 3 | $2.2 \cdot 10^{-4}$ |
| 86–95 | 5 | $6.0 \cdot 10^{-5}$ | 44 ± 3 | 3 | $3.0 \cdot 10^{-4}$ |
| 90–99 | 6 | $1.5 \cdot 10^{-5}$ | 83 ± 13 | 5 | no inhibition[c] |
| 94–103 | 4 | $1.2 \cdot 10^{-4}$ | 15 ± 9 | 3 | $4.5 \cdot 10^{-4}$ |
| 97–106 | 5 | $1.2 \cdot 10^{-4}$ | 0 | 4 | $7.5 \cdot 10^{-5}$ |
| 100–109 | 4 | $1.2 \cdot 10^{-4}$ | 0 | 3 | $2.2 \cdot 10^{-4}$ |
| 82–108 | 8 | $6.0 \cdot 10^{-8}$ | 75 ± 5 | 4 | $3.0 \cdot 10^{-5}$ |
| Linear M82–108 | 3 | $1.2 \cdot 10^{-7}$ | 86 ± 4 | 5 | $3.0 \cdot 10^{-5}$ |
| Cyclic M82–108 | 3 | $1.2 \cdot 10^{-7}$ | 66 ± 6 | 3 | $3.0 \cdot 10^{-4}$ |
| 86–104 | 5 | $6.0 \cdot 10^{-7}$ | 61 ± 5 | 3 | $4.5 \cdot 10^{-4}$ |
| 86–99 | 3 | $6.0 \cdot 10^{-6}$ | 81 ± 3 | 3 | no inhibition |
| B/PI | 3 | $5.5 \cdot 10^{-9}$ | 87 ± 8 | 3 | $1.5 \cdot 10^{-8}$ |

[a]Bactericidal activity toward *P. aeruginosa*; the highest concentration tested was $1.2 \cdot 10^{-4}$ M.
[b]The mean ± one standard error of the mean.
[c]Gelation of amoebocyte lysate was inhibited at the molar concentration shown; the highest concentration tested was $4.5 \cdot 10^{-4}$ M.

TABLE 11A

| | Bactericidal Activity Towards 5 $-10^6$ Bacteria[a] pH 7.0 | | | Endotoxin | |
|---|---|---|---|---|---|
| | Concn. | | | neutralization | |
| Peptide | n | effective dose (M) | % bacteria killed[b] | n | Concn.[c] (M) |
| 80–89 | 3 | $1.2 \cdot 10^{-4}$ | 0 | 3 | $4.5 \cdot 10^{-4}$ |
| 83–92 | 3 | $3.0 \cdot 10^{-5}$ | 72 ± 10 | 3 | $2.2 \cdot 10^{-4}$ |
| 86–95 | 5 | $6.0 \cdot 10^{-5}$ | 64 ± 8 | 3 | $3.0 \cdot 10^{-4}$ |
| 90–99 | 6 | $1.5 \cdot 10^{-5}$ | 83 ± 15 | 5 | no inhibition[c] |
| 94–103 | 4 | $1.2 \cdot 10^{-4}$ | 35 ± 11 | 3 | $4.5 \cdot 10^{-4}$ |
| 97–106 | 3 | $1.2 \cdot 10^{-4}$ | 0 | 4 | $7.5 \cdot 10^{-5}$ |
| 100–109 | 3 | $1.2 \cdot 10^{-4}$ | 0 | 3 | $2.2 \cdot 10^{-4}$ |
| 82–108 | 10 | $1.2 \cdot 10^{-7}$ | 75 ± 5 | 4 | $3.0 \cdot 10^{-5}$ |
| Linear M82-108 | 4 | $1.2 \cdot 10^{-7}$ | 45 ± 7 | 5 | $3.0 \cdot 10^{-5}$ |
| Cyclic M82-108 | 4 | $1.2 \cdot 10^{-7}$ | 50 ± 12 | 3 | $3.0 \cdot 10^{-4}$ |
| 86–104 | 4 | $6.0 \cdot 10^{-7}$ | 62 ± 9 | 3 | $4.5 \cdot 10^{-4}$ |
| 86–99 | 3 | $6.0 \cdot 10^{-6}$ | 79 ± 3 | 3 | no inhibition |
| B/PI | 3 | $1.1 \cdot 10^{-8}$ | 80 ± 3 | 3 | $1.5 \cdot 10^{-8}$ |

[a]Bactericidal activity toward *P. aeruginosa*; the highest concentration tested was $1.2 \cdot 10^{-4}$ M.
[b]The mean ± one standard error of the mean.
[c]Gelation of amoebocyte lysate was inhibited at the molar concentration shown; the highest concentration tested was $4.5 \cdot 10^{-4}$ M.

TABLE 12

| Comparative biologic activities of peptides | | | |
|---|---|---|---|
| Peptide | $LD_{50}$ pH 7.0 | Relative bactericidal activity | Relative endotoxin-neutralizing activity |
| 90–99 | $8.2 \cdot 10^{-6}$ M | 1 | 0 |
| 86–104 | $5.1 \cdot 10^{-7}$ M | 16 | 1 |
| 82–108 | $6.0 \cdot 10^{-8}$ M | 137 | 7[a] |
| B/PI | $1.0 \cdot 10^{-8}$ M | 833 | 3333 |

[a]If the 97–106 peptide is compared, tethering has amplified the activity 2.5-fold.

Since some endotoxin neutralization activity was found on both ends of the B/PI sequence 80-109, a longer peptide 82-108 was synthesized which incorporated most of the C- and N-terminal peptides and corresponded in length to strand 2 and 2 of LALF (Hoess, et al. supra) . Peptide 82-108 was considerably more effective both as a bactericidal agent and at endotoxin neutralization. Tethering by overlap of endotoxin-neutralizing peptides from the N- and C-terminal ends of B/PI sequence 80-109 with the central bactericidal peptides, as naturally occurs in parent B/PI, increased both activities simultaneously (Table 12). For each activity taken separately, effects from increasing the peptide length were synergistically modulated. Bactericidal activity of peptide 82-108 was considerably greater than the sum of activities from any shorter peptides derived from this sequence. Bactericidal activity of 82-108 was also 8.5-fold more active than peptide 86-104 and 137-fold more active than peptide 90-99. Endotoxin neutralizing activity was increased approximately 3-fold. This observation indicates that some spatial relationship between residues at both termini of peptide 82-108 modulates the bactericidal activity at its center. Thus, the activity of 86-104 was amplified considerably by extending the synthetic sequence to 82-108, especially with regard to bactericidal activity and endotoxin neutralization.

A modified peptide 82-108 (M82-108) was synthesized with two cysteines in place of residues 85 and 106. Sulfhydryl oxidation placed a disulfide bond in a site spanning the two cysteines residues. This covalent constraint tied the two ends of the modified peptide M82-108 together in an anti-parallel B-sheet fashion. Tables 11 and 11a show that bactericidal efficacy at pH 7.0 was unchanged as compared to linear peptide 82-108 of B/PI. Endotoxin neutralization was less in the cyclic peptide but the linear modified peptide with two free sulfhydryls retained endotoxin neutralizing activity.

EXAMPLE 9

Endotoxin Neutralizing Activity of BG38

Short peptides based on amino acids 82–108 of B/PI neutralize LPS toxicity in vitro (supra). The ability of one of the B/PI peptides (SEQ ID NO:62, BG38) to antagonize the toxic effects of LPS in an in vivo model of gram negative bacterial infection was tested. Mice were challenged intravenously with *P. aeruginosa* LPS and treated with BG38 or a 27 amino acid control peptide. Serum endotoxin and tumor necrosis factor alpha (TNF) levels were measured using the Limulus amebocyte lysate assay (supra).

Peptide BG38 demonstrated potent LPS antagonism in vivo. Endotoxin levels were two log orders lower in the BG38 treated group than in the control animals. BG38 also decreased the peak serum TNF level that occurred after LPS challenge. This data demonstrated that anti-endotoxin peptide BF38 efficiently neutralized LPS and attenuated LPS induced cytokine secretion in vivo. Therefore, this domain is useful in recombinant or synthetic constructs as endotoxin antagonists that neutralize LPS and demonstrate effector functions conferred by other protein domains. These compounds are useful as adjuncts to antibiotics or to other antimicrobial therapies for gram negative bacterial infections.

All publications and patent applications in this specification are indicative of the level of ordinary skill in the art to which this invention pertains. All publications and patent applications are herein incorporated by reference to the same extent as if each individual publication or patent application was specifically and individually indicated by reference.

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

What is claimed is:

1. A hybrid peptide having bactericidal and endotoxin neutralizing activity comprising exogenous amino acids flanking an amino acid sequence derived from bactericidal/permeability increasing protein, wherein the amino acid sequence comprises at least the amino acid region KWKAQKRFLK in forward or reverse order and with up to four amino acid substitutions.

2. The hybrid peptide of claim 1, wherein the exogenous amino acids flank both sides of the amino acid sequence from B/PI.

3. The hybrid peptide of claim 1, wherein the exogenous amino acids are on one side of the amino acid sequence from B/PI.

4. The hybrid peptide of claim 1, wherein the amino acid sequence from B/PI is in the reverse orientation.

5. The hybrid peptide of claim 2, wherein the amino acid sequence comprises at least one and up to four amino acid substitutions.

6. The hybrid peptide of claim 4, wherein the amino acid sequence comprises at least one and up to four amino acid substitutions.

7. The hybrid peptide of claim 1, wherein the hybrid peptide has a sequence selected from the group consisting of:

HIKELQVKWKAQKRFLKMSIIVKLNDGRELSLD (SEQ ID NO:63),

ANIKLSVKWKAQKRFLKMSIIVKLNDGRELSLD (SEQ ID NO:64),

SIQDLNVSMKLFRKQAKWKIIVKLNDGRELSLD (SEQ ID NO:65), and

ANIKLSVEMKLFKRHLKWKIIVKLNDGRELSLD (SEQ ID NO:66).

8. A peptide having bactericidal or endotoxin neutralizing activity, wherein said peptide comprises an amino acid sequence KWKAQKRFLK, wherein the peptide has at least two cysteine residues positioned within the peptide so that the amino acid sequence KWKAQKRFLK is positioned between at least two of the cysteine residues.

9. The peptide of claim 8, wherein the amino acid sequence comprises at least the amino acid region KWKAQKRFLK and no more than the amino acid sequence ISNANIKISGKWKAQKRFLKMSGNFDLSI from B/PI.

10. The peptide of claim 8, wherein the peptide is selected from a group consisting of:

ISNANCKISGKWKAQKRFLKMSGNFDCSI (SEQ ID NO:61) and

NANCKISGKWKAQKRFLKMSGNFDCSI (SEQ ID NO:62).

11. The peptide of claim 10, wherein the peptide is synthesized in the reverse orientation.

12. The peptide of claim 11, wherein the peptide is synthesized from D-amino acids.

13. A peptide having bactericidal or endotoxin neutralizing activity, comprising an amino acid sequence KWKAQKRFLKA from B/PI in reverse orientation.

14. The peptide of claim 13, wherein the peptide is synthesized from D-amino acids.

15. A method of treating a bacterial infection or endotoxic shock comprising administering an amount of a composition effective to inhibit the bacterial infection or neutralize endotoxin in an animal, wherein the composition comprises the hybrid peptide of claim 1.

16. The method of claim 15, wherein the peptide comprises at least KWKAQKRFLK and no more than the amino acid sequence ISNANIKISGKWKAQKRFLKMSGN-FDLSI.

17. The method of claim 15, wherein the peptide comprises at least one and up to four amino acid substitutions in the amino acid sequence KWKAQKRFLK.

* * * * *

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
( A ) LENGTH: 900 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
( A ) NAME/KEY: Coding Sequence
( B ) LOCATION: 1...900
( D ) OTHER INFORMATION:

( x i ) SEQUENCE DESCRIPTION: SEQ ID NO:1:

```
ATG AGA GAG AAC ATG GCC AGG GGC CCT TGC AAC GCG CCG AGA TGG GTG    48
Met Arg Glu Asn Met Ala Arg Gly Pro Cys Asn Ala Pro Arg Trp Val
 1               5                  10                  15

TCC CTG ATG GTG CTC GTC GCC ATA GGC ACC GCC GTG ACA GCG GCC GTC    96
Ser Leu Met Val Leu Val Ala Ile Gly Thr Ala Val Thr Ala Ala Val
            20                  25                  30

AAC CCT GGC GTC GTG GTC AGG ATC TCC CAG AAG GGC CTG GAC TAC GCC   144
Asn Pro Gly Val Val Val Arg Ile Ser Gln Lys Gly Leu Asp Tyr Ala
        35                  40                  45

AGC CAG CAG GGG ACG GCC GCT CTG CAG AAG GAG CTG AAG AGG ATC AAG   192
Ser Gln Gln Gly Thr Ala Ala Leu Gln Lys Glu Leu Lys Arg Ile Lys
    50                  55                  60

ATT CCT GAC TAC TCA GAC AGC TTT AAG ATC AAG CAT CTT GGG AAG GGG   240
Ile Pro Asp Tyr Ser Asp Ser Phe Lys Ile Lys His Leu Gly Lys Gly
65                  70                  75                  80

CAT TAT AGC TTC TAC AGC ATG GAC ATC CGT GAA TTC CAG CTT CCC AGT   288
His Tyr Ser Phe Tyr Ser Met Asp Ile Arg Glu Phe Gln Leu Pro Ser
                85                  90                  95

TCC CAG ATA AGC ATG GTG CCC AAT GTG GGC CTT AAG TTC TCC ATC AGC   336
Ser Gln Ile Ser Met Val Pro Asn Val Gly Leu Lys Phe Ser Ile Ser
            100                 105                 110

AAC GCC AAT ATC AAG ATC AGC GGG AAA TGG AAG GCA CAA AAG AGA TTC   384
Asn Ala Asn Ile Lys Ile Ser Gly Lys Trp Lys Ala Gln Lys Arg Phe
        115                 120                 125

TTA AAA ATG AGC GGC AAT TTT GAC CTG AGC ATA GAA GGC ATG TCC ATT   432
```

-continued

```
Leu  Lys  Met  Ser  Gly  Asn  Phe  Asp  Leu  Ser  Ile  Glu  Gly  Met  Ser  Ile
     130                      135                      140

TCG  GCT  GAT  CTG  AAG  CTG  GGC  AGT  AAC  CCC  ACG  TCA  GGC  AAG  CCC  ACC     480
Ser  Ala  Asp  Leu  Lys  Leu  Gly  Ser  Asn  Pro  Thr  Ser  Gly  Lys  Pro  Thr
145                      150                      155                      160

ATC  ACC  TGC  TCC  AGC  TGC  AGC  AGC  CAC  ATC  AAC  AGT  GTC  CAC  GTG  CAC     528
Ile  Thr  Cys  Ser  Ser  Cys  Ser  Ser  His  Ile  Asn  Ser  Val  His  Val  His
                    165                      170                      175

ATC  TCA  AAG  AGC  AAA  GTC  GGG  TGG  CTG  ATC  CAA  CTC  TTC  CAC  AAA  AAA     576
Ile  Ser  Lys  Ser  Lys  Val  Gly  Trp  Leu  Ile  Gln  Leu  Phe  His  Lys  Lys
               180                      185                      190

ATT  GAG  TCT  GCG  CTT  CGA  AAC  AAG  ATG  AAC  AGC  CAG  GTC  TGC  GAG  AAA     624
Ile  Glu  Ser  Ala  Leu  Arg  Asn  Lys  Met  Asn  Ser  Gln  Val  Cys  Glu  Lys
          195                      200                      205

GTG  ACC  AAT  TCT  GTA  TCC  TCC  AAG  CTG  CAA  CCT  TAT  TTC  CAG  ACT  CTG     672
Val  Thr  Asn  Ser  Val  Ser  Ser  Lys  Leu  Gln  Pro  Tyr  Phe  Gln  Thr  Leu
     210                      215                      220

CCA  GTA  ATG  ACC  AAA  ATA  GAT  TCT  GTG  GCT  GGA  ATC  AAC  TAT  GGT  CTG     720
Pro  Val  Met  Thr  Lys  Ile  Asp  Ser  Val  Ala  Gly  Ile  Asn  Tyr  Gly  Leu
225                      230                      235                      240

GTG  GCA  CCT  CCA  GCA  ACC  ACG  GCT  GAG  ACC  CTG  GAT  GTA  CAG  ATG  AAG     768
Val  Ala  Pro  Pro  Ala  Thr  Thr  Ala  Glu  Thr  Leu  Asp  Val  Gln  Met  Lys
                    245                      250                      255

GGG  GAG  TTT  TAC  AGT  GAG  AAC  CAC  CAC  AAT  CCA  CCT  CCC  TTT  GCT  CCA     816
Gly  Glu  Phe  Tyr  Ser  Glu  Asn  His  His  Asn  Pro  Pro  Pro  Phe  Ala  Pro
               260                      265                      270

CCA  GTG  ATG  GAG  TTT  CCC  GCT  GCC  CAT  GAC  CGC  ATG  GTA  TAC  CTG  GGC     864
Pro  Val  Met  Glu  Phe  Pro  Ala  Ala  His  Asp  Arg  Met  Val  Tyr  Leu  Gly
          275                      280                      285

CTC  TCA  GAC  TAC  TTC  TTC  AAC  ACA  GCC  GGG  CTT  GTA                         900
Leu  Ser  Asp  Tyr  Phe  Phe  Asn  Thr  Ala  Gly  Leu  Val
     290                      295                      300
```

( 2 ) INFORMATION FOR SEQ ID NO:2:

( i ) SEQUENCE CHARACTERISTICS:
( A ) LENGTH: 300 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

```
Met  Arg  Glu  Asn  Met  Ala  Arg  Gly  Pro  Cys  Asn  Ala  Pro  Arg  Trp  Val
 1                   5                        10                       15

Ser  Leu  Met  Val  Leu  Val  Ala  Ile  Gly  Thr  Ala  Val  Thr  Ala  Ala  Val
               20                       25                       30

Asn  Pro  Gly  Val  Val  Val  Arg  Ile  Ser  Gln  Lys  Gly  Leu  Asp  Tyr  Ala
          35                       40                       45

Ser  Gln  Gln  Gly  Thr  Ala  Ala  Leu  Gln  Lys  Glu  Leu  Lys  Arg  Ile  Lys
     50                       55                       60

Ile  Pro  Asp  Tyr  Ser  Asp  Ser  Phe  Lys  Ile  Lys  His  Leu  Gly  Lys  Gly
65                       70                       75                       80

His  Tyr  Ser  Phe  Tyr  Ser  Met  Asp  Ile  Arg  Glu  Phe  Gln  Leu  Pro  Ser
```

-continued

```
                    85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
    130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Lys Leu Gln Pro Tyr Phe Gln Thr Leu
    210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Pro Phe Ala Pro
            260                 265                 270

Pro Val Met Glu Phe Pro Ala Ala His Asp Arg Met Val Tyr Leu Gly
        275                 280                 285

Leu Ser Asp Tyr Phe Phe Asn Thr Ala Gly Leu Val
    290                 295                 300
```

( 2 ) INFORMATION FOR SEQ ID NO:3:

( i ) SEQUENCE CHARACTERISTICS:
( A ) LENGTH: 1653 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
( A ) NAME/KEY: Coding Sequence
( B ) LOCATION: 1...1461
( D ) OTHER INFORMATION:

( x i ) SEQUENCE DESCRIPTION: SEQ ID NO:3:

```
ATG AGA GAG AAC ATG GCC AGG GGC CCT TGC AAC GCG CCG AGA TGG GTG    48
Met Arg Glu Asn Met Ala Arg Gly Pro Cys Asn Ala Pro Arg Trp Val
  1               5                  10                  15

TCC CTG ATG GTG CTC GTC GCC ATA GGC ACC GCC GTG ACA GCG GCC GTC    96
Ser Leu Met Val Leu Val Ala Ile Gly Thr Ala Val Thr Ala Ala Val
             20                  25                  30

AAC CCT GGC GTC GTG GTC AGG ATC TCC CAG AAG GGC CTG GAC TAC GCC   144
Asn Pro Gly Val Val Val Arg Ile Ser Gln Lys Gly Leu Asp Tyr Ala
         35                  40                  45

AGC CAG CAG GGG ACG GCC GCT CTG CAG AAG GAG CTG AAG AGG ATC AAG   192
```

-continued

```
Ser Gln Gln Gly Thr Ala Ala Leu Gln Lys Glu Leu Lys Arg Ile Lys
     50                  55                  60

ATT CCT GAC TAC TCA GAC AGC TTT AAG ATC AAG CAT CTT GGG AAG GGG      240
Ile Pro Asp Tyr Ser Asp Ser Phe Lys Ile Lys His Leu Gly Lys Gly
65                  70                  75                  80

CAT TAT AGC TTC TAC AGC ATG GAC ATC CGT GAA TTC CAG CTT CCC AGT      288
His Tyr Ser Phe Tyr Ser Met Asp Ile Arg Glu Phe Gln Leu Pro Ser
                85                  90                  95

TCC CAG ATA AGC ATG GTG CCC AAT GTG GGC CTT AAG TTC TCC ATC AGC      336
Ser Gln Ile Ser Met Val Pro Asn Val Gly Leu Lys Phe Ser Ile Ser
            100                 105                 110

AAC GCC AAT ATC AAG ATC AGC GGG AAA TGG AAG GCA CAA AAG AGA TTC      384
Asn Ala Asn Ile Lys Ile Ser Gly Lys Trp Lys Ala Gln Lys Arg Phe
        115                 120                 125

TTA AAA ATG AGC GGC AAT TTT GAC CTG AGC ATA GAA GGC ATG TCC ATT      432
Leu Lys Met Ser Gly Asn Phe Asp Leu Ser Ile Glu Gly Met Ser Ile
    130                 135                 140

TCG GCT GAT CTG AAG CTG GGC AGT AAC CCC ACG TCA GGC AAG CCC ACC      480
Ser Ala Asp Leu Lys Leu Gly Ser Asn Pro Thr Ser Gly Lys Pro Thr
145                 150                 155                 160

ATC ACC TGC TCC AGC TGC AGC AGC CAC ATC AAC AGT GTC CAC GTG CAC      528
Ile Thr Cys Ser Ser Cys Ser Ser His Ile Asn Ser Val His Val His
                165                 170                 175

ATC TCA AAG AGC AAA GTC GGG TGG CTG ATC CAA CTC TTC CAC AAA AAA      576
Ile Ser Lys Ser Lys Val Gly Trp Leu Ile Gln Leu Phe His Lys Lys
            180                 185                 190

ATT GAG TCT GCG CTT CGA AAC AAG ATG AAC AGC CAG GTC TGC GAG AAA      624
Ile Glu Ser Ala Leu Arg Asn Lys Met Asn Ser Gln Val Cys Glu Lys
        195                 200                 205

GTG ACC AAT TCT GTA TCC TCC AAG CTG CAA CCT TAT TTC CAG ACT CTG      672
Val Thr Asn Ser Val Ser Ser Lys Leu Gln Pro Tyr Phe Gln Thr Leu
    210                 215                 220

CCA GTA ATG ACC AAA ATA GAT TCT GTG GCT GGA ATC AAC TAT GGT CTG      720
Pro Val Met Thr Lys Ile Asp Ser Val Ala Gly Ile Asn Tyr Gly Leu
225                 230                 235                 240

GTG GCA CCT CCA GCA ACC ACG GCT GAG ACC CTG GAT GTA CAG ATG AAG      768
Val Ala Pro Pro Ala Thr Thr Ala Glu Thr Leu Asp Val Gln Met Lys
                245                 250                 255

GGG GAG TTT TAC AGT GAG AAC CAC CAC AAT CCA CCT CCC TTT GCT CCA      816
Gly Glu Phe Tyr Ser Glu Asn His His Asn Pro Pro Pro Phe Ala Pro
            260                 265                 270

CCA GTG ATG GAG TTT CCC GCT GCC CAT GAC CGC ATG GTA TAC CTG GGC      864
Pro Val Met Glu Phe Pro Ala Ala His Asp Arg Met Val Tyr Leu Gly
        275                 280                 285

CTC TCA GAC TAC TTC TTC AAC ACA GCC GGG CTT GTA TAC CAA GAG GCT      912
Leu Ser Asp Tyr Phe Phe Asn Thr Ala Gly Leu Val Tyr Gln Glu Ala
    290                 295                 300

GGG GTC TTG AAG ATG ACC CTT AGA GAT GAC ATG ATT CCA AAG GAG TCC      960
Gly Val Leu Lys Met Thr Leu Arg Asp Asp Met Ile Pro Lys Glu Ser
305                 310                 315                 320

AAA TTT CGA CTG ACA ACC AAG TTC TTT GGA ACC TTC CTA CCT GAG GTG     1008
Lys Phe Arg Leu Thr Thr Lys Phe Phe Gly Thr Phe Leu Pro Glu Val
                325                 330                 335

GCC AAG AAG TTT CCC AAC ATG AAG ATA CAG ATC CAT GTC TCA GCC TCC     1056
Ala Lys Lys Phe Pro Asn Met Lys Ile Gln Ile His Val Ser Ala Ser
            340                 345                 350

ACC CCG CCA CAC CTG TCT GTG CAG CCC ACC GGC CTT ACC TTC TAC CCT     1104
Thr Pro Pro His Leu Ser Val Gln Pro Thr Gly Leu Thr Phe Tyr Pro
        355                 360                 365

GCC GTG GAT GTC CAG GCC TTT GCC GTC CTC CCC AAC TCC TCC CTG GCT     1152
```

-continued

```
Ala Val Asp Val Gln Ala Phe Ala Val Leu Pro Asn Ser Ser Leu Ala
    370                 375                 380

TCC CTC TTC CTG ATT GGC ATG CAC ACA ACT GGT TCC ATG GAG GTC AGC      1200
Ser Leu Phe Leu Ile Gly Met His Thr Thr Gly Ser Met Glu Val Ser
385                 390                 395                 400

GCC GAG TCC AAC AGG CTT GTT GGA GAG CTC AGG CTG GAT AGG CTG CTC      1248
Ala Glu Ser Asn Arg Leu Val Gly Glu Leu Arg Leu Asp Arg Leu Leu
                405                 410                 415

CTG CAA CTG AAG CAC TCA AAT ATT GGC CCC TTC CCG GTT GAA TTG CTG      1296
Leu Gln Leu Lys His Ser Asn Ile Gly Pro Phe Pro Val Glu Leu Leu
            420                 425                 430

CAG GAT ATC ATG AAC TAC ATT GTA CCC ATT CTT GTG CTG CCC AGG GTT      1344
Gln Asp Ile Met Asn Tyr Ile Val Pro Ile Leu Val Leu Pro Arg Val
        435                 440                 445

AAC GAG AAA CTA CAG AAA GGC TTC CCT CTC CCG ACG CCG GCC AGA GTC      1392
Asn Glu Lys Leu Gln Lys Gly Phe Pro Leu Pro Thr Pro Ala Arg Val
    450                 455                 460

CAG CTC TAC AAC GTA GTG CTT CAG CCT CAC CAG AAC TTC CTG CTG TTC      1440
Gln Leu Tyr Asn Val Val Leu Gln Pro His Gln Asn Phe Leu Leu Phe
465                 470                 475                 480

GGT GCA GAC GTT GTC TAT AAA TGAAGGCACC AGGGGTGCCG GGGGCTGTCA GCCGC 1496
Gly Ala Asp Val Val Tyr Lys
                485

ACCTGTTCCT GATGGGCTGT GGGGCACCGG CTGCCTTTCC CCAGGGAATC CTCTCCAGAT    1556

CTTAACCAAG AGCCCCTTGC AAACTTCTTC GACTCAGATT CAGAAATGAT CTAAACACGA    1616

GGAAACATTA TTCATTGGAA AAGTGCATGG TGTGTAT                             1653
```

( 2 ) INFORMATION FOR SEQ ID NO:4:

( i ) SEQUENCE CHARACTERISTICS:
( A ) LENGTH: 487 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:4:

```
Met Arg Glu Asn Met Ala Arg Gly Pro Cys Asn Ala Pro Arg Trp Val
  1               5                  10                  15

Ser Leu Met Val Leu Val Ala Ile Gly Thr Ala Val Thr Ala Ala Val
            20                  25                  30

Asn Pro Gly Val Val Val Arg Ile Ser Gln Lys Gly Leu Asp Tyr Ala
        35                  40                  45

Ser Gln Gln Gly Thr Ala Ala Leu Gln Lys Glu Leu Lys Arg Ile Lys
    50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
```

-continued 115 120 125

Leu Lys Met Ser Gly Asn Phe Asp Leu Ser Ile Glu Gly Met Ser Ile
130 135 140

Ser Ala Asp Leu Lys Leu Gly Ser Asn Pro Thr Ser Gly Lys Pro Thr
145 150 155 160

Ile Thr Cys Ser Ser Cys Ser Ser His Ile Asn Ser Val His Val His
165 170 175

Ile Ser Lys Ser Lys Val Gly Trp Leu Ile Gln Leu Phe His Lys Lys
180 185 190

Ile Glu Ser Ala Leu Arg Asn Lys Met Asn Ser Gln Val Cys Glu Lys
195 200 205

Val Thr Asn Ser Val Ser Ser Lys Leu Gln Pro Tyr Phe Gln Thr Leu
210 215 220

Pro Val Met Thr Lys Ile Asp Ser Val Ala Gly Ile Asn Tyr Gly Leu
225 230 235 240

Val Ala Pro Pro Ala Thr Thr Ala Glu Thr Leu Asp Val Gln Met Lys
245 250 255

Gly Glu Phe Tyr Ser Glu Asn His His Asn Pro Pro Pro Phe Ala Pro
260 265 270

Pro Val Met Glu Phe Pro Ala Ala His Asp Arg Met Val Tyr Leu Gly
275 280 285

Leu Ser Asp Tyr Phe Phe Asn Thr Ala Gly Leu Val Tyr Gln Glu Ala
290 295 300

Gly Val Leu Lys Met Thr Leu Arg Asp Asp Met Ile Pro Lys Glu Ser
305 310 315 320

Lys Phe Arg Leu Thr Thr Lys Phe Phe Gly Thr Phe Leu Pro Glu Val
325 330 335

Ala Lys Lys Phe Pro Asn Met Lys Ile Gln Ile His Val Ser Ala Ser
340 345 350

Thr Pro Pro His Leu Ser Val Gln Pro Thr Gly Leu Thr Phe Tyr Pro
355 360 365

Ala Val Asp Val Gln Ala Phe Ala Val Leu Pro Asn Ser Ser Leu Ala
370 375 380

Ser Leu Phe Leu Ile Gly Met His Thr Thr Gly Ser Met Glu Val Ser
385 390 395 400

Ala Glu Ser Asn Arg Leu Val Gly Glu Leu Arg Leu Asp Arg Leu Leu
405 410 415

Leu Gln Leu Lys His Ser Asn Ile Gly Pro Phe Pro Val Glu Leu Leu
420 425 430

Gln Asp Ile Met Asn Tyr Ile Val Pro Ile Leu Val Leu Pro Arg Val
435 440 445

Asn Glu Lys Leu Gln Lys Gly Phe Pro Leu Pro Thr Pro Ala Arg Val
450 455 460

Gln Leu Tyr Asn Val Val Leu Gln Pro His Gln Asn Phe Leu Leu Phe
465 470 475 480

Gly Ala Asp Val Val Tyr Lys
485

( 2 ) INFORMATION FOR SEQ ID NO:5:

( i ) SEQUENCE CHARACTERISTICS:
( A ) LENGTH: 21 amino acids
( B ) TYPE: amino acid
( C ) STRANDEDNESS: single
( D ) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

```
Val Asn Pro Gly Val Val Val Arg Ile Ser Gln Lys Gly Leu Asp Tyr
1               5                   10                  15

Ala Ser Gln Gln Gly
            20
```

(2) INFORMATION FOR SEQ ID NO:6:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

```
Lys Trp Lys Ala Gln Lys Arg Phe Leu Lys
1               5                   10
```

(2) INFORMATION FOR SEQ ID NO:7:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

```
Cys Lys Trp Lys Ala Gln Lys Arg Phe Leu Lys
1               5                   10
```

(2) INFORMATION FOR SEQ ID NO:8:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO ( v ) FRAGMENT TYPE: internal ( v i ) ORIGINAL SOURCE:

( x i ) SEQUENCE DESCRIPTION: SEQ ID NO:8:

Lys Trp Lys Ala Gln Lys Arg Phe Leu Lys Met Ser Gly
1 5 10

( 2 ) INFORMATION FOR SEQ ID NO:9:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:9:

Lys Ile Ser Gly Lys Trp Lys Ala Gln Lys Arg Phe Leu Lys
1 5 10

( 2 ) INFORMATION FOR SEQ ID NO:10:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:10:

Cys Lys Ile Ser Gly Lys Trp Lys Ala Gln Lys Arg Phe Leu Lys
1 5 10 15

( 2 ) INFORMATION FOR SEQ ID NO:11:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:11:

Glu Phe Tyr Ser Glu Asn His His Asn Pro Lys Trp Lys Ala Gln Lys

-continued 1 5 10 15

Arg Phe Leu Lys
20

( 2 ) INFORMATION FOR SEQ ID NO:12:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:12:

Cys Glu Phe Tyr Ser Glu Asn His His Asn Pro Lys Trp Lys Ala Gln
1 5 10 15

Lys Arg Phe Leu Lys
20

( 2 ) INFORMATION FOR SEQ ID NO:13:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:13:

Met Arg Glu Asn Met Ala Arg Gly Pro Cys
1 5 10

( 2 ) INFORMATION FOR SEQ ID NO:14:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:14:

Lys Glu Leu Lys Arg Ile Lys Ile Pro Asp Tyr
1 5 10

( 2 ) INFORMATION FOR SEQ ID NO:15:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:15:

Lys Leu Gly Ser Asn Pro Thr Ser Gly Lys
1 5 10

( 2 ) INFORMATION FOR SEQ ID NO:16:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:16:

Lys Lys Ile Glu Ser Ala Leu Arg Asn Lys Met
1 5 10

( 2 ) INFORMATION FOR SEQ ID NO:17:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:17:

Cys Glu Phe Tyr Ser Glu Asn His His Asn Pro Gly
1 5 10

( 2 ) INFORMATION FOR SEQ ID NO:18:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:18:

```
Cys Asn Glu Lys Leu Gln Lys Gly Phe Pro Leu
 1               5                  10
```

( 2 ) INFORMATION FOR SEQ ID NO:19:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:19:

```
Lys Ile Ser Gly Lys Trp Lys Ala Gln Lys Arg Phe Leu Lys Met Ser
 1               5                  10                  15

Gly Asn Phe
```

( 2 ) INFORMATION FOR SEQ ID NO:20:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:20:

```
Asn Ala Asn Ile Lys Ile Ser Gly Lys Trp Lys Ala Gln Lys Arg Phe
 1               5                  10                  15

Leu Lys Met Ser Gly Asn Phe Asp Leu Ser Ile
            20                  25
```

( 2 ) INFORMATION FOR SEQ ID NO:21:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:21:

Val Asn Pro Gly Val Val Val Arg Ile Ser Gln Lys Gly Leu Asp Tyr
1 5 10 15

Ala Ser Gln Gln Gly Thr Ala Ala Leu Gln
20 25

(2) INFORMATION FOR SEQ ID NO:22:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:22:

Glu Phe Tyr Ser Glu Asn His His Asn Pro Gly
1 5 10

(2) INFORMATION FOR SEQ ID NO:23:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:23:

Asn Glu Lys Leu Gln Lys Gly Phe Pro Leu
1 5 10

(2) INFORMATION FOR SEQ ID NO:24:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:24:

Lys Trp Lys Phe Lys Gln Arg Ala Leu Lys
1 5 10

(2) INFORMATION FOR SEQ ID NO:25:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:25:

Cys Lys Trp Lys Ala Gln Lys Arg Phe Leu Lys Cys
1 5 10

(2) INFORMATION FOR SEQ ID NO:26:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:26:

Lys Trp Lys Ala Gln Lys Arg Phe Leu Lys Cys
1 5 10

(2) INFORMATION FOR SEQ ID NO:27:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:27:

Cys Lys Trp Lys Ala Gln Lys Arg Phe Leu Lys Met Ser Gly
1 5 10

( 2 ) INFORMATION FOR SEQ ID NO:28:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:28:

Cys Asn Ala Asn Ile Lys Ile Ser Gly Lys Trp Lys Ala Gln Lys Arg
1 5 10 15

Phe Leu Lys Met Ser Gly Asn Phe Asp Leu Ser Ile Cys
20 25

( 2 ) INFORMATION FOR SEQ ID NO:29:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:29:

Cys Lys Ile Ser Gly Lys Trp Lys Ala Gln Lys Arg Phe Leu Lys Met
1 5 10 15

Ser Gly Asn Phe Cys
20

( 2 ) INFORMATION FOR SEQ ID NO:30:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:30:

Cys Glu Phe Tyr Ser Glu Asn His His Asn Pro
1 5 10

( 2 ) INFORMATION FOR SEQ ID NO:31:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:31:

Cys Val Asn Pro Gly Val Val Val Arg Ile Ser Gln Lys Gly Leu Asp
1 5 10 15

Tyr Ala Ser Gln Gln Gly Thr Ala Ala Leu Gln
20 25

( 2 ) INFORMATION FOR SEQ ID NO:32:

( i ) SEQUENCE CHARACTERISTICS:
( A ) LENGTH: 25 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:32:

Ser Asp Ser Phe Lys Ile Lys His Leu Gly Lys Gly His Tyr Ser Phe
1 5 10 15

Tyr Ser Met Asp Ile Arg Glu Phe Gln
20 25

( 2 ) INFORMATION FOR SEQ ID NO:33:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:33:

Cys Asn Ala Asn Ile Lys Ile Ser Gly Lys Trp Lys Ala Gln Lys Arg
1 5 10 15

Phe Leu Lys Met Ser Gly Asn Phe Asp Leu Ser Ile Cys
20 25

( 2 ) INFORMATION FOR SEQ ID NO:34:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:34:

Cys Lys Ile Ser Gly Lys Trp Lys Ala Gln Lys Arg Phe Leu Lys Met
1 5 10 15

Ser Gly Asn Phe Cys
20

( 2 ) INFORMATION FOR SEQ ID NO:35:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:35:

Trp Lys Lys Phe Lys Gln Arg Ala Leu Lys
1 5 10

( 2 ) INFORMATION FOR SEQ ID NO:36:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:36:

Lys Lys Lys Trp Phe Arg Leu Ala Lys Gln
1 5 10

( 2 ) INFORMATION FOR SEQ ID NO:37:

( i ) SEQUENCE CHARACTERISTICS:
( A ) LENGTH: 10 amino acids
( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:37:

Lys Trp Lys Phe Lys Lys Arg Ala Leu Lys
1 5 10

( 2 ) INFORMATION FOR SEQ ID NO:38:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:38:

Lys Lys Lys Phe Phe Arg Leu Ala Lys Gln
1 5 10

( 2 ) INFORMATION FOR SEQ ID NO:39:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:39:

Lys Lys Lys Ala Phe Arg Leu Ala Lys Gln
1 5 10

( 2 ) INFORMATION FOR SEQ ID NO:40:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( vi ) ORIGINAL SOURCE:

( xi ) SEQUENCE DESCRIPTION: SEQ ID NO:40:

Cys Lys Trp Lys Ala Gln Lys Arg Phe Leu Lys Cys
1 5 10

( 2 ) INFORMATION FOR SEQ ID NO:41:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( ii ) MOLECULE TYPE: peptide ( iii ) HYPOTHETICAL: NO ( iv ) ANTI-SENSE: NO ( v ) FRAGMENT TYPE: internal ( vi ) ORIGINAL SOURCE:

( xi ) SEQUENCE DESCRIPTION: SEQ ID NO:41:

Cys Lys Glu Leu Lys Arg Ile Lys Ile Pro Asp Tyr
1 5 10

( 2 ) INFORMATION FOR SEQ ID NO:42:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( ii ) MOLECULE TYPE: peptide ( iii ) HYPOTHETICAL: NO ( iv ) ANTI-SENSE: NO ( v ) FRAGMENT TYPE: internal ( vi ) ORIGINAL SOURCE:

( xi ) SEQUENCE DESCRIPTION: SEQ ID NO:42:

Cys Lys Lys Ile Glu Ser Ala Leu Arg Asn Lys Met
1 5 10

( 2 ) INFORMATION FOR SEQ ID NO:43:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( ii ) MOLECULE TYPE: peptide ( iii ) HYPOTHETICAL: NO ( iv ) ANTI-SENSE: NO ( v ) FRAGMENT TYPE: internal ( vi ) ORIGINAL SOURCE:

( xi ) SEQUENCE DESCRIPTION: SEQ ID NO:43:

Cys Lys Leu Gly Ser Asn Pro Thr Ser Gly Lys 1 5 10

( 2 ) INFORMATION FOR SEQ ID NO:44:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:44:

Leu Pro Ser Ser Gln Ile Ser Met Val Pro Asn Val Gly Leu Lys Phe
1 5 10 15

Ser Ile Ser Asn Ala Asn Ile Lys Ile Ser Gly
20 25

( 2 ) INFORMATION FOR SEQ ID NO:45:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:45:

Met Ser Gly Asn Phe Asp Leu Ser Ile Glu Gly Met Ser Ile Ser Ala
1 5 10 15

Asp Leu ( 2 ) INFORMATION FOR SEQ ID NO:46:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:46:

Pro Thr Ile Thr Cys Ser Ser Cys Ser Ser His Ile Asn Ser Val His
1 5 10 15

Val His Ile Ser Lys Ser Lys Val Gly Trp Leu Ile Gln Leu Phe His

-continued 20 25 30

(2) INFORMATION FOR SEQ ID NO:47:

(i) SEQUENCE CHARACTERISTICS:
(A) LENGTH: 30 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:47:

Met Asn Ser Gln Val Cys Glu Lys Val Thr Asn Ser Val Ser Ser Lys
1 5 10 15

Leu Gln Pro Tyr Phe Gln Thr Leu Pro Val Met Thr Lys Ile
20 25 30

(2) INFORMATION FOR SEQ ID NO:48:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:48:

Ile Lys Thr Lys Lys Phe Leu Lys Lys Thr
1 5 10

(2) INFORMATION FOR SEQ ID NO:49:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:49:

Lys Thr Lys Cys Lys Phe Leu Lys Lys Cys
1 5 10

(2) INFORMATION FOR SEQ ID NO:50:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:50:

Cys Lys Thr Lys Cys Lys Phe Leu Lys Lys Cys
1 5 10

(2) INFORMATION FOR SEQ ID NO:51:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:51:

Met Ser Gly Asn Phe Asp Leu Ser Ile Glu
1 5 10

(2) INFORMATION FOR SEQ ID NO:52:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:52:

Ile Ser Asn Ala Asn Ile Lys Ile Ser Gly
1 5 10

(2) INFORMATION FOR SEQ ID NO:53:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:53:

Ala Asn Ile Lys Ile Ser Gly Lys Trp Lys
1 5 10

( 2 ) INFORMATION FOR SEQ ID NO:54:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:54:

Lys Ile Ser Gly Lys Trp Lys Ala Gln Lys
1 5 10

( 2 ) INFORMATION FOR SEQ ID NO:55:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:55:

Gln Lys Arg Phe Leu Lys Met Ser Gly Asn
1 5 10

( 2 ) INFORMATION FOR SEQ ID NO:56:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:56:

Phe Leu Lys Met Ser Gly Asn Phe Asp Leu
1 5 10

( 2 ) INFORMATION FOR SEQ ID NO:57:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:57:

Cys Phe Leu Lys Met Ser Gly Asn Phe Asp Leu Cys
1 5 10

( 2 ) INFORMATION FOR SEQ ID NO:58:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:58:

Asn Ala Asn Ile Lys Ile Ser Gly Lys Trp Lys
1 5 10

( 2 ) INFORMATION FOR SEQ ID NO:59:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:59:

Cys Glu Phe Tyr Ser Glu Asn His His Asn Pro Lys Trp Lys Ala Gln
1 5 10 15

Lys Arg Phe Leu Lys Cys
20

( 2 ) INFORMATION FOR SEQ ID NO:60:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:60:

Cys Lys Ile Ser Gly Lys Trp Lys Ala Gln Lys Arg Phe Leu Lys Cys
1 5 10 15

( 2 ) INFORMATION FOR SEQ ID NO:61:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:61:

Ile Ser Asn Ala Asn Cys Lys Ile Ser Gly Lys Trp Lys Ala Gln Lys
1 5 10 15

Arg Phe Leu Lys Met Ser Gly Asn Phe Asp Cys Ser Ile
20 25

( 2 ) INFORMATION FOR SEQ ID NO:62:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:62:

Asn Ala Asn Cys Lys Ile Ser Gly Lys Trp Lys Ala Gln Lys Arg Phe
1 5 10 15

Leu Lys Met Ser Gly Asn Phe Asp Cys Ser Ile
20 25

( 2 ) INFORMATION FOR SEQ ID NO:63:

(i) SEQUENCE CHARACTERISTICS:
(A) LENGTH: 33 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:63:

His Ile Lys Glu Leu Gln Val Lys Trp Lys Ala Gln Lys Arg Phe Leu
1 5 10 15

Lys Met Ser Ile Ile Val Lys Leu Asn Asp Gly Arg Glu Leu Ser Leu
20 25 30

Asp (2) INFORMATION FOR SEQ ID NO:64:

(i) SEQUENCE CHARACTERISTICS:
(A) LENGTH: 33 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:64:

Ala Asn Ile Lys Leu Ser Val Lys Trp Lys Ala Gln Lys Arg Phe Leu
1 5 10 15

Lys Met Ser Ile Ile Val Lys Leu Asn Asp Gly Arg Glu Leu Ser Leu
20 25 30

Asp (2) INFORMATION FOR SEQ ID NO:65:

(i) SEQUENCE CHARACTERISTICS:
(A) LENGTH: 33 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:65:

Ser Ile Gln Asp Leu Asn Val Ser Met Lys Leu Phe Arg Lys Gln Ala
1 5 10 15

-continued

| | | | | | | | | | | | | | | | |
|---|---|---|---|---|---|---|---|---|---|---|---|---|---|---|---|
| Lys | Trp | Lys | Ile<br>20 | Ile | Val | Lys | Leu | Asn<br>25 | Asp | Gly | Arg | Glu | Leu<br>30 | Ser | Leu |
| Asp | | | | | | | | | | | | | | | |

( 2 ) INFORMATION FOR SEQ ID NO:66:

( i ) SEQUENCE CHARACTERISTICS:
( A ) LENGTH: 33 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:66:

| | | | | | | | | | | | | | | | |
|---|---|---|---|---|---|---|---|---|---|---|---|---|---|---|---|
| Ala<br>1 | Asn | Ile | Lys | Leu<br>5 | Ser | Val | Glu | Met | Lys<br>10 | Leu | Phe | Lys | Arg | His<br>15 | Leu |
| Lys | Trp | Lys | Ile<br>20 | Ile | Val | Lys | Leu | Asn<br>25 | Asp | Gly | Arg | Glu | Leu<br>30 | Ser | Leu |
| Asp | | | | | | | | | | | | | | | |